US008119805B2

(12) United States Patent
Reich et al.

(10) Patent No.: US 8,119,805 B2
(45) Date of Patent: Feb. 21, 2012

(54) SUBSTITUTED DISULFONAMIDE COMPOUNDS

(75) Inventors: Melanie Reich, Aachen (DE); Stefan Schunk, Aachen (DE); Ruth Jostock, Stolberg (DE); Sabine Hees, Aachen (DE); Tieno Germann, Aachen (DE); Michael Franz-Martin Engels, Turnhout (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 12/613,974

(22) Filed: Nov. 6, 2009

(65) Prior Publication Data

US 2010/0152158 A1 Jun. 17, 2010

Related U.S. Application Data

(60) Provisional application No. 61/111,900, filed on Nov. 6, 2008.

(30) Foreign Application Priority Data

Nov. 6, 2008 (EP) ..................... 08019454

(51) Int. Cl.
| C07D 221/02 | (2006.01) |
| C07D 221/20 | (2006.01) |
| C07D 401/14 | (2006.01) |
| C07D 417/14 | (2006.01) |
| C07D 409/14 | (2006.01) |
| C07D 403/14 | (2006.01) |
| A61K 31/496 | (2006.01) |
| A61K 31/497 | (2006.01) |
| A61K 31/445 | (2006.01) |

(52) U.S. Cl. ......... 546/112; 546/16; 546/202; 546/187; 546/208; 544/364; 514/210.2; 514/253.09; 514/278; 514/318

(58) Field of Classification Search .......... None
See application file for complete search history.

(56) References Cited

U.S. PATENT DOCUMENTS

| 6,967,196 B1 * | 11/2005 | Smith et al. ............ 514/210.1 |
| 2008/0153843 A1 | 6/2008 | Oberboersch et al. |
| 2008/0249128 A1 | 10/2008 | Oberboersch et al. |
| 2009/0215828 A1 * | 8/2009 | Schunk et al. ............ 514/336 |

FOREIGN PATENT DOCUMENTS

| WO | WO 2006/071775 A2 | 7/2006 |
| WO | WO 2007/101007 A2 | 9/2007 |
| WO | WO 2007/140383 A2 | 12/2007 |
| WO | WO 2008/040492 A1 | 4/2008 |
| WO | WO 2008/046573 A1 | 4/2008 |

OTHER PUBLICATIONS

Fila-Hromadko, et al., Croatica Chemica Acta (1967) 39, 207-213 (abstract only).*

Sara H. Bengtson, et al, "Kinin Receptor Expression during *Staphylococcus aureus* Infection", Blood, Sep. 15, 2006, pp. 2055-2063, vol. 108, No. 6, The American Society of Hematology, Washington, DC, USA.
Joao B. Calixto, et al., "Kinin $B_1$ Receptors: Key G-Protein-Coupled Receptors and their Role in Inflammatory and Painful Processes", British Journal of Pharmacology, 2004, pp. 803-818, vol. 143, Nature Publishing Group.
R. Hayashi et al., "Bradykinin Stimulates IL-6 and IL-8 Production by Human Lung Fibroblasts through ERK- and p38 MAPK-dependent Mechanisms", European Respiratory Journal, 2000, pp. 452-458, vol. 16, ERS Journals Ltd.
L.M. Fredrik Leeb-Lundberg et al., "International Union of Pharmacology. XLV. Classification of the Kinin Receptor Family: from Molecular Mechanisms to Pathophysiological Consequences", Pharmacological Reviews, 2005, pp. 27-77, vol. 57, No. 1, The American Society for Pharmacology and Experimental Therapeutics, USA.
Giselle F. Passos et al., "Kinin $B_1$ Receptor Up-Regulation after Lipopolysaccharide Adminstration: Role of Proinflammatory Cytokines and Neutrophil Influx[1]", The Journal of Immunology, 2004, pp. 1839-1847, vol. 172, The American Association of Immunologists, Inc.
Joao B. Pesquero et al., "Genetically Altered Animal Models in the Kallikrein-Kinin System", Biol. Chem., Feb. 2006, pp. 119-126, vol. 387.
Joao B. Pesquero et al., "Hypoalgesia and Altered Inflammatory Responses in Mice Lacking Kinin B1 Receptors", PNAS, Jul. 5, 2000, pp. 8140-8145, vol. 97, No. 14.
A. Prat et al, "Bradykinin $B_1$ Receptor Expression and Function on T Lymphocytes in Active Multiple Sclerosis", Neurology, Dec. 10, 1999, pp. 2087-2092, vol. 53, No. 9, 1999 American Academy of Neurology.
Antoni Stadnicki et al., "Immunolocalization and Expression of Kinin $B_1R$ and $B_2R$ Receptors in Human Inflammatory Bowel Disease", Am. J. Physiol. Gastrointest. Liver Physiol., Mar. 31, 2005, pp. G361-G366, vol. 289, American Physiological Society.
International Search Report mailed Dec. 9, 2009.
Robert W. Colman, "Regulation of angiogenesis by the kallikrein-kinin system", Current Pharmaceutical Design, vol. 12, No. 21, pp. 2599-2607, 2006.
Parenti et al., "The bradykinin/B1 receptor promotes angiogenesis by up-regulation of endogenous FGF-2 in endothelium via the nitric oxide synthase pathway", FASEB J 2001; 15: 1497-1489.

* cited by examiner

*Primary Examiner* — Kamal Saeed
*Assistant Examiner* — Nyeemah A Grazier
(74) *Attorney, Agent, or Firm* — Crowell & Moring LLP

(57) ABSTRACT

Substituted disulfonamide compounds corresponding to formula I:

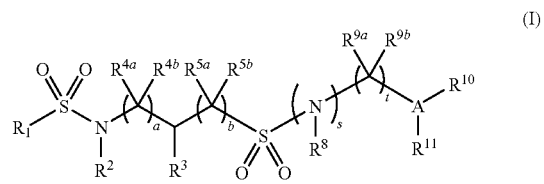

In which $R^1$, $R^2$, $R^3$, $R^{4a}$, $R^{4b}$, $R^{5a}$, $R^{5b}$, $R^8$, $R^{9a}$, $R^{9b}$, $R^{10}$, $R^{11}$, a, b, s, t and A have defined meanings, pharmaceutical compositions containing one or more such compounds, processes for preparing such compounds, and a method of using such compounds for the treatment or inhibition of pain and/or other conditions mediated by the bradykinin receptor 1 (BR1).

22 Claims, No Drawings

SUBSTITUTED DISULFONAMIDE COMPOUNDS

CROSS REFERENCE TO RELATED APPLICATIONS

This application claims priority from U.S. provisional patent application No. 61/111,900, filed Nov. 6, 2008, the entire disclosure of which is incorporated herein by reference. Priority is also claimed based on European patent application no. EP 080 19454.1, filed Nov. 6, 2008.

BACKGROUND OF THE INVENTION

The present invention relates to substituted disulfonamides, processes for the preparation thereof, pharmaceutical compositions containing these compounds and the use of substituted disulfonamides for the preparation of medicaments.

In contrast to the constitutive expression of the bradykinin 2 receptor (B2R), in most tissues the bradykinin 1 receptor (B1R) is not expressed or is expressed only weakly. Nevertheless, expression of B1R can be induced on various cells. For example, in the course of inflammation reactions a rapid and pronounced induction of B1R takes place on neuronal cells, but also various peripheral cells, such as fibroblasts, endothelial cells, granulocytes, macrophages and lymphocytes. In the course of inflammation reactions, a switch from a B2R to a B1R dominance thus occurs on the cells involved. The cytokines interleukin-1 (IL-1) and tumour necrosis factor alpha (TNFα) are involved to a considerable degree in this upwards regulation of B1R (Passos et al. J. Immunol. 2004, 172, 1839-1847). After activation with specific ligands, B1R-expressing cells then themselves can secrete inflammation-promoting cytokines such as IL-6 and IL-8 (Hayashi et al., Eur. Respir. J. 2000, 16, 452-458). This leads to inwards migration of further inflammation cells, e.g. neutrophilic granulocytes (Pesquero et al., PNAS 2000, 97, 8140-8145). The bradykinin B1R system can contribute towards chronification of diseases via these mechanisms. This is demonstrated by a large number of animal studies (overviews in Leeb-Lundberg et al., Pharmacol Rev. 2005, 57, 27-77 and Pesquero et al., Biol. Chem. 2006, 387, 119-126). On humans too, an enhanced expression of B1R, e.g. on enterocytes and macrophages in the affected tissue of patients with inflammatory intestinal diseases (Stadnicki et al., Am. J. Physiol. Gastrointest. Liver Physiol. 2005, 289, G361-366) or on T lymphocytes of patients with multiple sclerosis (Prat et al., Neurology. 1999; 53, 2087-2092) or an activation of the bradykinin B2R—B1R system in the course of infections with *Staphyloccocus aureus* (Bengtson et al., Blood 2006, 108, 2055-2063) is found. Infections with *Staphyloccocus aureus* are responsible for syndromes such as superficial infections of the skin up to septic shock.

Based on the pathophysiological relationships described, there is a great therapeutic potential for the use of B1R antagonists on acute and, in particular, chronically inflammatory diseases. These include diseases of the respiratory tract (bronchial asthma, allergies, COPD/chronic obstructive pulmonary disease, cystic fibrosis etc.), inflammatory intestinal diseases (ulcerative colitis, CD/Crohn's disease etc.), neurological diseases (multiple sclerosis, neurodegeneration etc.), inflammations of the skin (atopic dermatitis, psoriasis, bacterial infections etc.) and mucous membranes (Behcet's disease, pelvitis, prostatitis etc.), rheumatic diseases (rheumatoid arthritis, osteoarthritis etc.), septic shock and reperfusion syndrome (following cardiac infarction, stroke).

The bradykinin (receptor) system is moreover also involved in regulation of angiogenesis (potential as an angiogenesis inhibitor in cancer cases and macular degeneration on the eye), and B1R knockout mice are protected from induction of obesity by a particularly fat-rich diet (Pesquero et al., Biol. Chem. 2006, 387, 119-126). B1R antagonists are therefore also suitable for treatment of obesity.

B1R antagonists are suitable in particular for treatment of pain, particularly inflammation pain and neuropathic pain (Calixto et al., Br. J. Pharmacol 2004, 1-16), and in particular diabetic neuropathy (Gabra et al., Biol. Chem. 2006, 387, 127-143). They are furthermore suitable for treatment of migraine.

In the development of B1R modulators, however, there is the problem that the human and the rat B1 receptor differ so widely that many compounds which are good B1R modulators on the human receptor have only a poor or no affinity for the rat receptor. This makes pharmacological studies on animals considerably difficult, since many studies are usually conducted on the rat. However, if no activity exists on the rat receptor, neither the action nor side effects can be investigated on the rat. This has already led to transgenic animals with human B1 receptors being produced for pharmacological studies on animals (Hess et al., Biol. Chem. 2006; 387(2): 195-201). Working with transgenic animals, however, is more expensive than working with the unmodified animals.

The patent applications WO 2008/040492 and WO 2008/046573 describe compounds which, in in vitro assays, show an antagonistic action both on the human B1 receptor and on the B1 receptor of the rat.

The patent applications WO 2007/140383 and WO 2007/101007 describe compounds which have an antagonistic action on the macaque B1 receptor in in vitro assays. Experimental data on the activity on the human B1 receptor or the B1 receptor of the rat are not disclosed.

There continues to be a need for novel B1R modulators, B1R modulators which bind both to the rat receptor and to the human receptor offering particular advantages.

SUMMARY OF THE INVENTION

One object of the present invention was therefore to provide novel compounds which are suitable in particular as pharmacological active compounds in medicaments, preferably in medicaments for treatment of disorders or diseases which are at least partly mediated by B1R receptors.

This and other objects have been achieved by the substituted disulfonamides according to the invention.

The invention therefore provides substituted disulfonamides of the general formula I

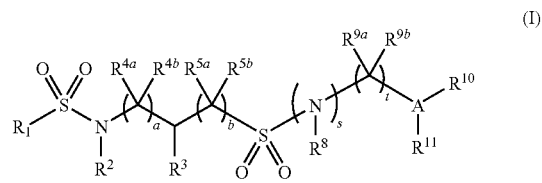

wherein
a represents 0, 1 or 2;
b represents 0, 1, 2, 3 or 4;
$R^1$ represents aryl, heteroaryl or an aryl or heteroaryl group bonded via a $C_{1-3}$-alkylene group, wherein aryl and heteroaryl in each case can be fused with a 4-, 5-, 6- or 7-membered ring or heterocyclic ring, wherein the ring and the heterocyclic ring is in each case saturated or at least monounsaturated, but not aromatic, and in each case can be substituted on one or more of its carbon ring members by one or more radicals independently of one another selected from the group consisting of F, Cl, B, I, —CF$_3$, —O—CF$_3$, and C$_{1-6}$-alkyl, and wherein the heterocyclic ring can contain one or more hetero atoms or hetero atom groups independently of one another selected from the group consisting of N, NR$^{50}$, O, S, S=O or S(=O)$_2$, R$^2$ and R$^3$ are defined as described under (i) or (ii):

(i) R$^2$ represents H, C$_{1-6}$-alkyl, C$_{3-8}$cycloalkyl, aryl or heteroaryl, or R$^2$ denotes a C$_{3-8}$-cycloalkyl, aryl or heteroaryl group bonded via a C$_{1-6}$-alkylene group, C$_{2-6}$-alkenylene group or C$_{2-6}$-alkynylene group;

R$^3$ represents H, F, Cl, Br, I, —CF$_3$, —OCF$_3$, OH, O—C$_{1-6}$-alkyl, C$_{1-6}$-alkyl, C$_{3-8}$-cycloalkyl, aryl or heteroaryl, or R$^3$ denotes a C$_{3-8}$-cycloalkyl, aryl or heteroaryl group bonded via a C$_{1-6}$-alkylene group, C$_{2-6}$-alkenylene group or C$_{2-6}$-alkynylene group; or (ii) R$^2$ and R$^3$, together with the —N—(CR$^{4a}$R$^{4b}$)$_a$—CH— group joining them, form a heterocyclic ring which, on one or more of its carbon ring members, can be substituted by one or more radicals independently of one another selected from the group consisting of F, Cl, Br, I, —CF$_3$, —O—CF$_3$ and —SH and/or can be fused with at least one aryl or heteroaryl, and/or two of its carbon ring members are bonded to one another via a C$_{1-3}$ alkylene bridge, wherein said heterocyclic ring is saturated or at least monounsaturated, but not aromatic, is 4-, 5-, 6- or 7-membered, and can contain, in addition to the N hetero atom to which R$^2$ is bonded, one or more hetero atoms or hetero atom groups independently of one another selected from the group consisting of N, NR$^{50}$, O, S, S=O or S(=O)$_2$; wherein R$^{50}$ denotes H, C$_{1-6}$-alkyl, —C(=O)—R$^{51}$, C$_{3-8}$-cycloalkyl, aryl, heteroaryl or a C$_{3-8}$-cycloalkyl, aryl or heteroaryl group bonded via a C$_{1-3}$-alkylene group, and R$^{51}$ denotes C$_{1-6}$-alkyl, C$_{3-8}$cycloalkyl, aryl, heteroaryl or a C$_{3-8}$-cycloalkyl, aryl or heteroaryl group bonded via a C$_{1-3}$-alkylene group;

R$^{4a}$, R$^{4b}$, R$^{5a}$, R$^{5b}$ each independently represent H, F, Cl, Br, I, —CF$_3$, —OCF$_3$, OH, SH, O—C$_{1-6}$-alkyl, C$_{1-6}$-alkyl, C$_{3-8}$-cycloalkyl, aryl or heteroaryl; or represent a C$_{3-8}$-cycloalkyl, aryl or heteroaryl group bonded via a C$_{1-6}$-alkylene group or C$_{2-6}$-alkenylene group;

s is 0 or 1;

t is 0, 1, 2 or 3;

R$^8$ represents H, C$_{1-6}$-alkyl, C$_{3-8}$cycloalkyl, aryl or heteroaryl, or a C$_{3-8}$-cycloalkyl, aryl or heteroaryl group bonded via a C$_{1-6}$-alkylene group;

R$^{9a}$ and R$^{9b}$ each independently denote H, F, Cl, OH, C$_{1-6}$-alkyl, O—C$_{1-6}$-alkyl, C$_{3-8}$-cycloalkyl, aryl or heteroaryl, or a C$_{3-8}$-cycloalkyl, aryl or heteroaryl group bonded via a C$_{1-6}$-alkylene group;

A represents N or CH;

with the proviso that if s represents 1 and t represents 0, A represents CH; and with the proviso that if s and t in each case represent 0, A represents N;

R$^{10}$ and R$^{11}$ together with A, represent a spirocyclic or cyclic group corresponding to formula (II) or formula (III)

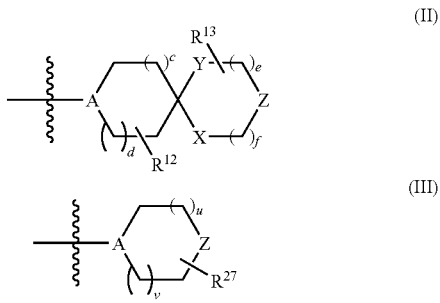

wherein c, d, e, f, u and v each independently denote 0, 1 or 2;

R$^{12}$, R$^{13}$ and R$^{27}$ each independently represent 0 to 4 substituents, each independently selected from the group consisting of F, Cl, OH, =O, C$_{1-6}$-alkyl, O—C$_{1-6}$-alkyl, C$_{3-8}$-cycloalkyl, aryl, heteroaryl and C$_{3-8}$-cycloalkyl, aryl or heteroaryl group bonded via a C$_{1-6}$-alkylene group;

and/or in each case two of the 0-4 substituents R$^{27}$ together represent a C$_{1-3}$-alkylene bridge, so that the ring shown in the general formula (III) assumes a bicyclically bridged form;

and/or two adjacent substituents of the 0-4 substituents R$^{13}$ form a fused aryl or heteroary group;

and/or two adjacent substituents of the 0-4 substituents R$^{27}$ form a fused aryl or heteroaryl;

X represents CR$^{14a}$R$^{14b}$, NR$^{15}$ or O;

Y represents CR$^{16a}$R$^{16b}$, NR$^{17}$ or O;

with the proviso that X does not denote NR$^{15}$ if Y denotes NR$^{17}$; and with the proviso that X and Y do not simultaneously denote O;

wherein

R$^{14a}$, R$^{14b}$, R$^{16a}$ and R$_{16b}$ each independently denote H, F, Cl, OH, C$_{1-6}$-alkyl, O—C$_{1-6}$-alkyl, C$_{3-8}$-cycloalkyl, aryl or heteroaryl, or represent a C$_{3-8}$-cycloalkyl, aryl or heteroaryl group bonded via a C$_{1-6}$-alkylene group, and/or R$^{14a}$ and R$^{14b}$ may together represent =O and/or R$^{16a}$ and R$^{16b}$ together can represent =O;

R$^{15}$ and R$^{17}$ each independently represent H, C$_{1-6}$-alkyl, C$_{3-8}$-cycloalkyl, aryl or heteroaryl, or denote a C$_{3-8}$-cycloalkyl, aryl or heteroaryl group bonded via a C$_{1-6}$-alkylene group;

Z in formula (II) represents CR$^{18a}$R$^{18b}$, NR$^{19}$ or O; or

Z in formula (II), if X represents O and f represents 0, may denote —(C(R$^{124}$)—C(R$^{125}$))—, wherein R$^{124}$ and R$^{125}$, together with the carbon atoms joining them, form a condensed-on aryl or heteroaryl ring; or Z in formula (II), if X represents O and f represents 0, denotes =(N(CR$^{126}$))—, wherein the N atom is bonded to the O atom via a single bond, and R$^{126}$ represents H, C$_{1-6}$-alkyl, C$_{3-8}$cycloalkyl, aryl or heteroaryl, or denotes a C$_{3-8}$-cycloalkyl, aryl or heteroaryl group bonded via a C$_{1-6}$-alkylene group;

Z in formula (III) represents CR$^{18a}$R$^{18b}$, NR$^{19}$, O, S, S(=O) or S(=O)$_2$; wherein R$^{18a}$ represents H, C$_{1-6}$-alkyl, C$_{3-8}$cycloalkyl, aryl or heteroaryl, or denotes a C$_{3-8}$-cycloalkyl, aryl or heteroaryl group bonded via a C$_{1-6}$-alkylene group, or $R^{18a}$ represents a group corresponding to formula (IV)

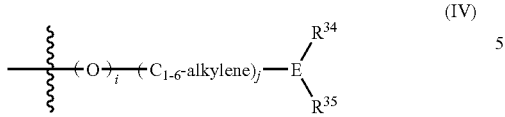
(IV)

wherein
i and j each independently represent 0 or 1;
E represents N or CH, with the proviso that if i represents 1 and j represents 0, then E represents CH;
$R^{34}$ and $R^{35}$ each independently denote H, $C_{1-6}$-alkyl, $C_{3-8}$-cycloalkyl, aryl or heteroaryl, or an aryl, heteroaryl or $C_{3-8}$-cycloalkyl group bonded via a $C_{1-3}$-alkylene group; or
$R^{34}$ and $R^{35}$ together with E, form a 5- or 6-membered aryl or heteroaryl group; or
$R^{34}$ and $R^{35}$ together with E, form a saturated heterocyclic ring corresponding to formula (V)

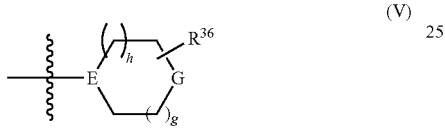
(V)

wherein
h and g each independently denote 0, 1 or 2;
G represents $CR^{37a}R^{37b}$, $NR^{38}$, O, S, S=O or $S(=O)_2$, with the proviso that if E represents CH, G does not represent $CR^{37a}R^{37b}$;
$R^{36}$ represents 0 to 4 substituents, each independently selected from the group consisting of F, Cl, Br, I, OH, SH, =O, O—$C_{1-6}$-alkyl, $C_{1-6}$-alkyl, $C_{3-8}$-cycloalkyl, aryl, heteroaryl and $C_{3-8}$-cycloalkyl, aryl or heteroaryl group bonded via a $C_{1-6}$-alkylene group; and/or
two adjacent substituents $R^{36}$ together represent a fused aryl or heteroaryl group;
$R^{37a}$ and $R^{37b}$ each independently denote H, F, Cl, Br, I, OH, SH, =O, O—$C_{1-6}$-alkyl, $C_{1-6}$-alkyl, $C_{3-8}$-cycloalkyl, aryl or heteroaryl, or represent a $C_{3-8}$-cycloalkyl, aryl or heteroaryl group bonded via a $C_{1-6}$-alkylene group;
$R^{38}$ represents H, $C_{1-6}$-alkyl, $C_{3-8}$-cycloalkyl, aryl or heteroaryl or denotes an aryl, heteroaryl or $C_{3-8}$-cycloalkyl bonded via a $C_{1-3}$-alkylene group;
$R^{18b}$ represents H, OH, $C_{1-6}$-alkyl, $C_{3-8}$-cycloalkyl, O—$C_{1-6}$-alkyl, O—($C_{3-8}$cycloalkyl), ($C_{1-6}$-alkylene)-O—$C_{1-6}$-alkyl, ($C_{1-6}$-alkylene)-O—($C_{3-8}$-cycloalkyl), aryl, heteroaryl, O-aryl or O-heteroaryl, or denotes an aryl, O-aryl, heteroaryl or O-heteroaryl group bonded via a $C_{1-6}$-alkylene group; or
$R^{18b}$ represents a group corresponding to formula (VI)

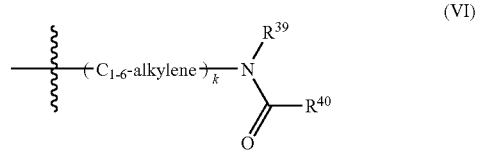
(VI)

wherein
K represents 0 or 1;
$R^{39}$ represents H, $C_{1-6}$-alkyl, $C_{3-8}$-cycloalkyl, aryl or heteroaryl, or denotes a $C_{3-8}$-cycloalkyl, aryl or heteroaryl group bonded via a $C_{1-3}$-alkylene group;
$R^{40}$ represents $C_{1-6}$-alkyl, $C_{3-8}$cycloalkyl, aryl or heteroaryl, or denotes a $C_{3-8}$-cycloalkyl, aryl or heteroaryl group bonded via a $C_{1-6}$-alkylene group; or
$R^{39}$ and $R^{40}$ together with the N—C(=O) group joining them, form a ring corresponding to formula (VII)

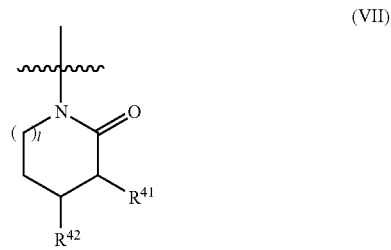
(VII)

wherein
I represents 0, 1 or 2; and
$R^{41}$ and $R^{42}$, together with the carbon atoms joining them, form a fused aryl or heteroaryl group;
$R^{19}$ represents H; or $(P)_z$—$R^{22}$,
wherein
z represents 0 or 1;
P represents (C=O), $S(=O)_2$ or C(=O)—$N(R^{24})$, wherein the N atom in the group C(=O)—$N(R^{24})$ is linked to $R^{22}$,
wherein
$R^{24}$ represents H, $C_{1-6}$-alkyl, $C_{3-8}$-cycloalkyl or an aryl, heteroaryl or $C_{3-8}$-cycloalkyl bonded via a $C_{1-3}$-alkylene group;
$R^{22}$ represents $C_{1-6}$-alkyl, aryl or heteroaryl, or denotes an aryl or heteroaryl group bonded via a $C_{1-6}$-alkylene group; or
$R^{22}$ represents a group corresponding to formula (VIII),

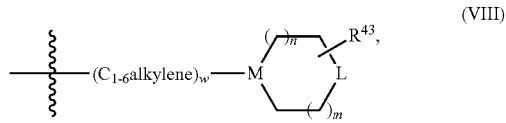
(VIII)

Wherein
n represents 0, 1 or 2;
m represents 0, 1 or 2;
w represents 0 or 1,
M represents CH or N;
with the proviso that if P represents C(=O)—$NR^{24}$ and w represents 0, then M represents CH; and
with the proviso that if z and w simultaneously represent 0, then M represents CH;
L represents $CR^{44a}R^{44b}$, $NR^{45}$, O, S, S=O or $S(=O)_2$;
$R^{43}$ represents 0 to 4 substituents, each independently selected from the group consisting of F, Cl, OH, =O, $C_{1-6}$-alkyl, O—$C_{1-6}$-alkyl, $C_{3-8}$-cycloalkyl, aryl, heteroaryl and a $C_{3-8}$-cycloalkyl, aryl or heteroaryl group bonded via a $C_{1-6}$-alkylene group;
and/or two adjacent substituents $R^{43}$ together represent a fused aryl or heteroaryl group;
$R^{44a}$ and $R^{44b}$ each independently represent H, F, Cl, Br, I, OH, $C_{1-6}$-alkyl, O—$C_{1-6}$-alkyl, $C_{3-8}$-cycloalkyl, aryl or heteroaryl, or denote a $C_{3-8}$-cycloalkyl, aryl or heteroaryl group bonded via a $C_{1-6}$-alkylene group; or $R^{44a}$ and $R^{44b}$ together may represent =O;

$R^{45}$ represents H, $C_{1-6}$-alkyl, $C_{3-8}$-cycloalkyl, aryl or heteroaryl, or denotes an aryl, heteroaryl or $C_{3-8}$-cycloalkyl group bonded via a $C_{1-3}$-alkylene group;

wherein the abovementioned $C_{1-3}$-alkylene, $C_{1-6}$-alkylene, $C_{2-6}$-alkenylene, $C_{2-6}$-alkynylene, $C_{3-6}$-cycloalkyl, $C_{3-8}$-cycloalkyl, aryl and heteroaryl groups may each be unsubstituted or substituted one or more times by identical or different substituents; and the abovementioned $C_{1-3}$-alkylene, $C_{2-6}$-alkenylene and $C_{2-6}$-alkynylene groups may each be branched or unbranched;

optionally in the form of an individual enantiomer or of an individual diastereomer, of the racemate, of the enantiomers, of the diastereomers, mixtures of the enantiomers and/or diastereomers, and in each case in the form of their bases and/or physiologically acceptable salts.

In the foregoing formula (IV), the bonds shown between E and $R^{34}$ and $R^{35}$ are not to be understood exclusively as single bonds, but can also be part of an aromatic system.

In the context of the present invention, the term "halogen" preferably represents F, Cl, Br and I, in particular F and Cl.

In the context of this invention, the expression "$C_{1-6}$-alkyl" includes acyclic saturated hydrocarbon radicals having 1, 2, 3, 4, 5 or 6 carbon atoms, which can be branched- or straight-chain (unbranched) and unsubstituted or substituted one or more times, for example 2, 3, 4 or 5 times, by identical or different substituents. The alkyl radicals can preferably be selected from the group consisting of methyl, ethyl, n-propyl, iso-propyl, n-butyl, iso-butyl, sec-butyl, tert-butyl, n-pentyl, iso-pentyl, neo-pentyl and hexyl. Particularly preferred alkyl radicals can be selected from the group consisting of methyl, ethyl, n-propyl, iso-propyl, n-butyl, sec-butyl, iso-butyl and tert-butyl.

In the context of this invention, the expression "$C_{3-8}$-cycloalkyl" denotes cyclic saturated hydrocarbons having 3, 4, 5, 6, 7 or 8 carbon atoms, which can be unsubstituted or substituted on one or more ring members one or more times, for example by 2, 3, 4 or 5 identical or different substituents. $C_{3-8}$-Cycloalkyl can preferably be selected from the group consisting of cyclopropyl, cyclobutyl, cyclopentyl, cyclohexyl, cycloheptyl and cyclooctyl.

In the context of this invention, the expression "aryl" denotes aromatic hydrocarbons, in particular phenyls and naphthyls. The aryl groups can also be condensed with further saturated, (partially) unsaturated or aromatic ring systems. Each aryl radical can be unsubstituted or substituted one or more times, for example 2, 3, 4 or 5 times, wherein the substituents on the aryl can be identical or different and can be in any desired and possible position of the aryl. Aryl can advantageously be selected from the group consisting of phenyl, 1-naphthyl and 2-naphthyl, which in each case can be unsubstituted or substituted one or more times, for example by 2, 3, 4 or 5 substituents.

In the context of the present invention, the expression "heteroaryl" represents a 5-, 6- or 7-membered cyclic aromatic group which contains at least 1, optionally also 2, 3, 4 or 5 hetero atoms, wherein the hetero atoms can be identical or different and the heteroaryl can be unsubstituted or substituted one or more times, for example 2, 3, 4 or 5 times, by identical or different substituents. The substituents can be bonded in any desired and possible position of the heteroaryl. The heterocyclic ring can also be part of a bi- or polycyclic, in particular a mono-, bi- or tricyclic system, which can then be more than 7-membered in total, preferably up to 14-membered. Preferred hetero atoms are selected from the group consisting of N, O and S. The heteroaryl group is preferably selected from the group consisting of pyrrolyl, indolyl, furyl (furanyl), benzofuranyl, thienyl (thiophenyl), benzothienyl, benzothiadiazolyl, benzothiazolyl, benzotriazolyl, benzodioxolanyl, benzodioxanyl, benzooxazolyl, benzooxadiazolyl, imidazothiazolyl, dibenzofuranyl, dibenzothienyl, phtalazinyl, pyrazolyl, imidazolyl, thiazolyl, oxazolyl, oxadiazolyl, triazole, tetrazole, isoxazoyl, pyridinyl (pyridyl), pyridazinyl, pyrimidinyl, pyrazinyl, pyranyl, indazolyl, purinyl, indolizinyl, quinolinyl, isoquinolinyl, quinazolinyl, quinoxalinyl, carbazolyl, phenazinyl, phenothiazinyl and oxadiazolyl, in particular from the group consisting of thienyl (thiophenyl), pyridinyl (pyridyl), pyrimidinyl, thiazolyl, triazolyl, imidazolyl, oxazolyl, oxadiazolyl, quinazolinyl, quinolinyl and isoquinolinyl, wherein bonding to the general structure (I) can be via any desired and possible ring member of the heteroaryl radical. The heteroaryl radical can be particularly preferably selected from the group consisting of thienyl, imidazoyl, thiazolyl, triazolyl, pyridinyl and pyrimidinyl.

In the context of the present invention, the expression "$C_{1-3}$-alkylene group" or "$C_{1-6}$-alkylene group" includes acyclic saturated hydrocarbon radicals having 1, 2 or 3 or, respectively, having 1, 2, 3, 4, 5 or 6 carbon atoms, which may be branched- or straight-chain (unbranched) and unsubstituted or substituted one or more times, for example 2, 3, 4 or 5 times, by identical or different substituents, and which link a corresponding group to the main structure. The alkylene groups can preferably be selected from the group consisting of —CH$_2$—, —CH$_2$—CH$_2$—, —CH(CH$_3$)—, —CH$_2$—CH$_2$—CH$_2$—, —CH(CH$_3$)—CH$_2$—, —CH(CH$_2$CH$_3$)—, —CH$_2$—(CH$_2$)$_2$—CH$_2$—, —CH(CH$_3$)—CH$_2$—CH$_2$—, —CH$_2$—CH(CH$_3$)—CH$_2$—, —CH(CH$_3$)—CH(CH$_3$)—, —CH(CH$_2$CH$_3$)—CH$_2$—, —C(CH$_3$)$_2$—CH$_2$—, —CH(CH$_2$CH$_2$CH$_3$)—, —C(CH$_3$)(CH$_2$CH$_3$)—, —CH$_2$—(CH$_2$)$_3$—CH$_2$—, —CH(CH$_3$)—CH$_2$—CH$_2$—CH$_2$—, —CH$_2$—CH(CH$_3$)—CH$_2$—CH$_2$—, —CH(CH$_3$)—CH$_2$—CH(CH$_3$)—, —CH(CH$_3$)—CH(CH$_3$)—CH$_2$—, —C(CH$_3$)$_2$—CH$_2$—CH$_2$—, —CH$_2$—C(CH$_3$)$_2$—CH$_2$—, —CH(CH$_2$CH$_3$)—CH$_2$—CH$_2$—, —CH$_2$—CH(CH$_2$CH$_3$)—CH$_2$—, —C(CH$_3$)$_2$—CH(CH$_3$)—, —CH(CH$_2$CH$_3$)—CH(CH$_3$)—, —C(CH$_3$)(CH$_2$CH$_3$)—CH$_2$—, —CH(CH$_2$CH$_2$CH$_3$)—CH$_2$—, —C(CH$_2$CH$_2$CH$_3$)—CH$_2$—, —CH(CH$_2$CH$_2$CH$_3$)—, —C(CH$_3$)(CH$_2$CH$_2$CH$_3$)—, —C(CH$_2$CH$_3$)$_2$— and —CH$_2$—(CH$_2$)$_4$—CH$_2$—. The alkylene groups can particularly preferably be selected from the group consisting of —CH$_2$—, —CH$_2$—CH$_2$— and —CH$_2$—CH$_2$—CH$_2$—.

In the context of the present invention, the expression "(C)$_{2-6}$alkylene group" additionally includes, in addition to the $C_{1-6}$-alkylene groups described above, those groups in which these groups are linked to the main structure via an oxygen atom.

In the context of the present invention, the expression "$C_{2-6}$-alkenylene group" includes acyclic hydrocarbon radicals having 2, 3, 4, 5 or 6 carbon atoms which are unsaturated one or more times, for example 2, 3 or 4 times, and can be branched- or straight-chain (unbranched) and unsubstituted or substituted one or more times, for example 2, 3, 4 or 5 times, by identical or different substituents and which link a corresponding radical to the main structure. In this context the alkenylene groups contain at least one C=C double bond. The alkenylene groups can preferably be selected from the group consisting of —CH=CH—, —CH=CH—CH$_2$—, —C(CH$_3$)=CH$_2$—, —CH=CH—CH$_2$—CH$_2$—, —CH$_2$—CH=CH—CH$_2$—, —CH=CH—CH=CH—, —C(CH$_3$)=CH—CH$_2$—, —CH=C(CH$_3$)—CH$_2$—, —C(CH$_3$)=C $(CH_3)$—, —$C(CH_2CH_3)$=CH—, —CH=CH—$CH_2$—$CH_2$—$CH_2$—, —$CH_2$—CH=$CH_2$—$CH_2$—$CH_2$—, —CH=CH—CH—$CH_2$—$CH_2$— and —CH=$CH_2$—CH—CH=$CH_2$—.

In the context of the invention, the expression "$C_{2-6}$-alkynylene group" includes acyclic hydrocarbon radicals having 2, 3, 4, 5 or 6 carbon atoms which are unsaturated one or more times, for example 2, 3 or 4 times, and can be branched- or straight-chain (unbranched) and unsubstituted or substituted one or more times, for example 2, 3, 4 or 5 times, by identical or different substituents and which link a corresponding radical to the main structure. In this context the alkynylene groups contain at least one C triple bond. The alkynylene groups can preferably be selected from the group consisting of —C≡C—, —C≡C—$CH_2$—, —C≡C—$CH_2$—, —C≡C—$CH(CH_3)$—, —$CH_2$—C≡C—$CH_2$—, —C≡C—C≡C—, —C≡C—$C(CH_3)_2$—, —C≡C—$CH_2$—$CH_2$—$CH_2$—, —$CH_2$—C≡C—$CH_2$—$CH_2$—, —C≡C—C≡C—$CH_2$— and —C≡C—$CH_2$—C≡C—.

In the context of the present invention, the expression "aryl or heteroaryl group bonded via a $C_{1-3}$-alkylene group, a $C_{1-6}$-alkylene group, $C_{2-6}$-alkenylene group or $C_{2-6}$-alkynylene group" means that the $C_{1-3}$-alkylene groups, $C_{1-6}$-alkylene groups, $C_{2-6}$-alkenylene groups, $C_{2-6}$-alkynylene groups and aryl or heteroaryl have the meanings defined above and the aryl or heteroaryl group is bonded to the main structure via a $C_{1-3}$-alkylene group, $C_{1-6}$-alkylene group, $C_{2-6}$-alkenylene group or $C_{2-6}$-alkynylene group. Examples which may be mentioned include benzyl, phenethyl and phenylpropyl.

In the context of the present invention, the expression "$C_{3-8}$-cycloalkyl and heterocycloalkyl bonded via a $C_{1-3}$-alkylene group, $C_{1-6}$-alkylene group, $C_{2-6}$-alkenylene group or $C_{2-6}$-alkynylene group" means that the $C_{1-3}$-alkylene group, $C_{1-6}$-alkylene group, $C_{2-6}$-alkenylene group, $C_{2-6}$-alkynylene group, $C_{3-8}$-cycloalkyl and heterocycloalkyl have the meanings defined above and $C_{3-8}$-cycloalkyl and heterocycloalkyl are bonded to the main structure via a $C_{1-3}$-alkylene group, $C_{1-6}$-alkylene group, $C_{2-6}$-alkenylene group or $C_{2-6}$-alkynylene group.

In connection with "alkyl", "alkylene", "alkenylene", "alkynylene" and "cycloalkyl", in the context of this invention the term "substituted" is understood as meaning replacement of a hydrogen by F, Cl, Br, I, $CF_3$, $OCF_3$, CN, $NH_2$; NH—$C_{1-6}$-alkyl, NH—$C_{1-6}$-alkylene-OH, N($C_{1-6}$-alkyl)$_2$, N($C_{1-6}$-alkylene-OH)$_2$, $NO_2$, SH, S—$C_{1-6}$-alkyl, $C_{1-6}$-alkyl, S-benzyl, O—$C_{1-6}$-alkyl, OH, O—$C_{1-6}$-alkylene-OH, =O, O-benzyl, C(=O)$C_{1-6}$-alkyl, $CO_2H$, $CO_2$—$C_{1-6}$-alkyl, phenyl, phenoxy, benzyl, naphthyl, furyl, thienyl and pyridinyl, wherein which are substituted several times are to be understood as meaning those group which are substituted several times, for example two or three times, either on different or on the same atoms, for example three times on the same C atom, as in the case of $CF_3$ or $CH_2CF_3$, or at different places, as in the case of CH(Cl)—CH=CH—$CHCl_2$. Substitution several times can be by identical or different substituents, such as, for example, in the case of CH(OH)—CH=CH—$CHCl_2$. In particular, this is to be understood as meaning replacement of one or more hydrogens by F, Cl, $NH_2$, OH, phenyl, O—$CF_3$ or O—$C_{1-6}$-alkyl, in particular by methoxy.

With respect to "aryl" and "heteroaryl", in the context of this invention "substituted" is understood as meaning replacement one or more times, for example 2, 3, 4 or 5 times, of one or more hydrogen atoms of the corresponding ring system by F, Cl, Br, I, CN, $NH_2$, NH—$C_{1-6}$-alkyl, NH—$C_{1-6}$-alkylene-OH, N($C_{1-6}$-alkyl)$_2$, N($C_{1-6}$-alkylene-OH)$_2$, NH-aryl$^1$, N(aryl$^1$)$_2$, N($C_{1-6}$-alkyl)aryl$^1$, pyrrolinyl, piperazinyl, morpholinyl, azetidinyl, piperidinyl, thiazolinyl, azepanyl, diazepanyl, ($C_{1-3}$-alkylene)-azetidinyl, ($C_{1-3}$-alkylene)-pyrrolinyl, ($C_{1-3}$-alkylene)-piperidinyl, ($C_{1-3}$-alkylene)-morpholinyl, ($C_{1-3}$-alkylene)-piperazinyl, ($C_{1-3}$-alkylene)-thiazolinyl, ($C_{1-3}$-alkylene)-azepanyl, ($C_{1-3}$-alkylene)-diazepanyl, $NO_2$, SH, OH, O—$C_{1-6}$-alkyl, O—$C_{1-6}$-alkyl-OH, C(=O)$C_{1-6}$-alkyl, $NHSO_2C_{1-6}$-alkyl, $NHCOC_{1-6}$-alkyl, $CO_2H$, $CH_2SO_2$-phenyl, $CO_2$—$C_{1-6}$-alkyl, $OCF_3$, $CF_3$, —O—$CH_2$—O—, —O—$CH_2$—$CH_2$—O—, —O—$C(CH_3)_2$—$CH_2$—, unsubstituted $C_{1-6}$-alkyl, pyrrolidinyl, imidazolyl, benzyloxy, phenoxy, phenyl, naphthyl, pyridinyl, —$C_{1-3}$-alkylene-aryl$^1$, benzyl, thienyl, furyl, wherein aryl$^1$ represents phenyl, thiazolyl, thienyl or pyridinyl, on one or various atoms, wherein the above-mentioned substituents—unless stated otherwise—may optionally be substituted in their turn by the aforementioned substituents. Substitution of aryl and heteroaryl several times can be by identical or different substituents. Preferred substituents for aryl and heteroaryl can be selected from the groups consisting of —O—$C_{1-3}$-alkyl, unsubstituted F, Cl, Br, I, CN, $CF_3$, $OCF_3$, OH, SH, —$CH_2$-azetidinyl, —$CH_2$-pyrrolidinyl, —$CH_2$-piperidinyl, —$CH_2$-piperazinyl, —$CH_2$-morpholinyl, phenyl, naphthyl, thiazolyl, thienyl and pyridinyl, in particular from the group consisting of F, Cl, CN, $CF_3$, $CH_3$; $OCH_3$, $OCF_3$, and —$CH_2$-azetidinyl.

In the context of the invention, "isolated" in connection with a stereoisomer means separated from other stereoisomers, but not necessarily other substances.

In the chemical structural formulas used here to describe the compounds according to the invention, the symbol $$"R^a \diagdown "$$

is also used to describe one or more substitution patterns, this group not being bonded to a particular atom within the chemical structural formula, in contrast to the representation of a bond to a particular atom (by way of example $R^a$ here represents a substituent R having a numbering represented by the variable "a"). This may be explained by way of example with the aid of the group $$"R^{27} \diagdown "$$

from formula (III) shown above: The definition for $R^{27}$ states that $R^{27}$ can represent 0 to 4 substituents. $R^{27}$ can therefore be absent, or 1, 2, 3 or 4 of the C-bonded hydrogen atoms within the partial structure represented by formula (III) can be replaced by a substituent envisaged in the definition of $R^{27}$, it being possible for the particular substituents to be chosen independently of one another, that is to say also to have different meanings, and for C-bonded hydrogen atoms on one or more carbon atoms to be replaced. As explained in the definition of $R^{27}$, two $R^{27}$ substituents together can also represent a $C_{1-3}$-alkylene bridge or a fused aryl or heteroaryl (also called condensed-on aryl or heteroaryl or fused/condensed-on aryl or heteroaryl group), so that $R^{27}$ in formula (III) also has the meanings shown below by way of example, in which $R^{27}$ represents two substituents on in each case different carbon atoms, and in the second example the variable u represents 1:

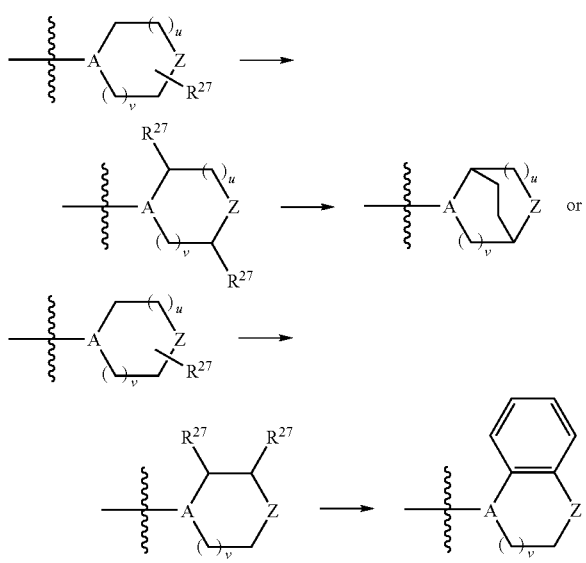

In the context of the present invention, the symbol

used in formulas designates a linking of a corresponding group to the particular main structure.

Those skilled in the art will understand that identical groups used for definition of different substituents are in each case independent of one another.

In the context of this invention, the term "physiologically acceptable salt" is understood as meaning preferably salts of the compounds according to the invention with inorganic or organic acids, which are physiologically acceptable, particularly when used on humans and/or mammals. Examples of suitable acids include hydrochloric acid, hydrobromic acid, sulfuric acid, methanesulfonic acid, formic acid, acetic acid, oxalic acid, succinic acid, tartaric acid, mandelic acid, fumaric acid, maleic acid, lactic acid, citric acid, glutamic acid, 1,1-dioxo-1,2-dihydro-1$\lambda^6$-benzo[d]isothiazol-3-one (saccharic acid), monomethylsebacic acid, 5-oxo-proline, hexane-1-sulfonic acid, nicotinic acid, 2-, 3- or 4-aminobenzoic acid, 2,4,6-trimethylbenzoic acid, α-lipoic acid, acetylglycine, hippuric acid, phosphoric acid and/or aspartic acid. The salts of hydrochloric acid (hydrochlorides) and of citric acid (citrates) are particularly preferred.

$R^1$ in the compounds according to the invention preferably represents phenyl, naphthyl, chromanyl, indolyl, benzofuranyl, benzothiophenyl (benzothienyl); benzooxazolyl, benzooxadiazolyl, pyrrolyl, furanyl, thienyl, pyridinyl, pyridazinyl, pyrimidinyl, pyrazinyl, imidazothiazolyl, carbazolyl, dibenzofuranyl, dibenzothiophenyl (dibenzothienyl), quinolinyl, isoquinolinyl or a phenyl or naphthyl bonded via a $C_{1-3}$-alkylene group, particularly preferably phenyl, naphthyl, chromanyl, benzothiophenyl (benzothienyl), quinolinyl, isoquinolinyl, thienyl or a phenyl bonded via a $C_{1-3}$-alkylene group, very particularly preferably phenyl, naphthyl, chromanyl, benzothiophenyl (benzothienyl) or a phenyl bonded via a $C_{1\ or\ 2}$-alkylene group, wherein the abovementioned aryl or heteroaryl radicals in each case are unsubstituted or substituted one or more times by identical or different substituents, wherein the substituents independently of one another in particular are selected from the group consisting of —O—$C_{1-3}$-alkyl, $C_{1-6}$-alkyl, F, Cl, Br, $CF_3$, $OCF_3$, OH, phenyl, phenoxy, naphthyl, thiazolyl, thienyl and pyridinyl and wherein the abovementioned alkylene groups in each case are unsubstituted or substituted one or more times by identical or different substituents, wherein the substituents independently of one another in particular are selected from the group consisting of —O—$C_{1-3}$-alkyl, —$C_{1-4}$-alkyl, F, Cl, Br, $CF_3$, $OCF_3$, OH, phenyl, phenoxy, naphthyl, furyl, thienyl and pyridinyl.

$R^1$ can represent in particular phenyl or naphthyl, wherein the phenyl or naphthyl is unsubstituted or substituted one or more times, for example 2, 3, 4 or 5 times, by identical or different substituents chosen from methyl, methoxy, $CF_3$, $OCF_3$, F and Cl.

In similarly preferred embodiments of the compounds of the invention, $R^1$ is selected from the group consisting of 4-methoxy-2,3,6-trimethylphenyl, 4-methoxy-2,6-dimethylphenyl, 4-methoxy-2,3,5-trimethylphenyl, 2,4,6-trimethylphenyl, 2-chloro-6-methylphenyl, 2,4,6-trichlorophenyl, 1,3-dichloro-5-trifluoromethylphenyl, 2-chloro-6-(trifluoromethyl)phenyl, 2,6-dichloro-4-methoxyphenyl, 2,6-dichloro-4-trifluoromethyl, 2-methylnaphthyl, 2-chloronaphthyl, 2-fluoronaphthyl, 2-chloro-4-(trifluoromethoxy) phenyl, 4-chloro-2,5-dimethylphenyl, 2-chloro-6-methylphenyl, 2,3-dichlorophenyl, 3,4-dichlorophenyl, 2,4-dichlorophenyl, 2,4,5-trichlorophenyl, 2,4,6-trichlorophenyl, 2-(trifluoromethyl)phenyl, 3-(trifluoromethyl)phenyl, 4-(trifluoromethyl)phenyl, 1-naphthyl and 2-naphthyl.

In similarly preferred embodiments of the compounds according to the invention, $R^1$ is selected from the group consisting of 4-methoxy-2,3,6-trimethylphenyl, 4-methoxy-2,6-dimethylphenyl, 2,4,6-trimethylphenyl, 2,6-dichloro-4-(trifluoromethyl)phenyl, 2-chloro-6-methylphenyl, 2,4,6-trichlorophenyl, 2,4,5-trichlorophenyl, 4-fluoro-2,6-dimethylphenyl, 2,6-dichloro-4-methoxyphenyl, 2,6-dichlorophenyl, 2,6-dichloro-3-methylphenyl, 6-methoxy-2-naphthyl, 2-methyl-1-naphthyl, 2-chloro-1-naphthyl, 2-fluoro-1-naphthyl, 2-chloro-4-(trifluoromethoxy)phenyl, 4-chloro-2,5-dimethylphenyl, 2-chlorobenzyl, 3-chlorobenzyl, 4-chlorobenzyl, 2,3-dichlorophenyl, 3,4-dichlorophenyl, 2,4-dichlorophenyl, 2-(trifluoromethyl)phenyl, 3-(trifluoromethyl)phenyl, 4-(trifluoromethyl)phenyl, 4-methyl-1-naphthyl, 5-chloro-1-naphthyl, 4-chloro-1-naphthyl, 4-fluoro-1-naphthyl, 4-methoxy-1-naphthyl, 1-naphthyl, 2-naphthyl, benzothiophenyl, 2,2-diphenylethanyl and 2,2-dimethylchroman-6-yl. In particular, $R^1$ can represent 4-methoxy-2,6-dimethylphenyl or 2-chloro-6-methylphenyl.

In similarly preferred embodiments of the compounds according to the invention corresponding to formula I, the part structure Ac I shown below

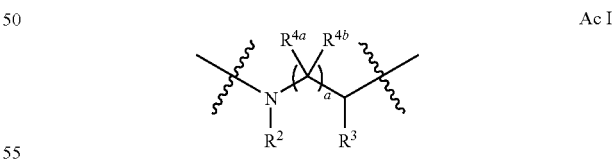

Ac I represents a group corresponding to formula Ac I.a

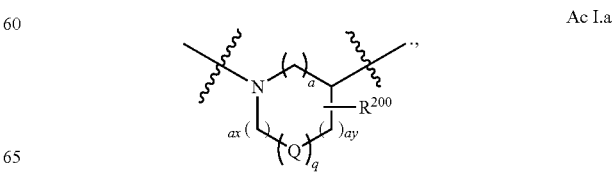

Ac I.a wherein a represents 0, 1 or 2;

ax represents 0, 1, 2 or 3;

ay represents 0, 1 or 2;

q represents 0 or 1;

with the proviso that a+ax+ay+q≧2 in particular 2, 3, 4 or 5;

Q represents $CH_2$, $NR^{50}$, O, S, S=O or S(=O)$_2$, wherein $R^{200}$ represents 0-4 substituents independently selected from the group consisting of F, Cl, —$CF_3$ and —O—$CF_3$, in particular represents F or $CF_3$, or two $R^{200}$ substituent together represent a fused aryl- or heteroaryl, in particular a benzo group.

If the structure of the N-containing heterocyclic ring allows, $R^{200}$ can therefore also represent two aryls, in particular benzo groups, fused on to the heterocyclic ring. In certain embodiments, $R^{200}$ represents 0 substituents, that is to say is absent.

In particular, the part structure Ac I can represent one of the following groups:

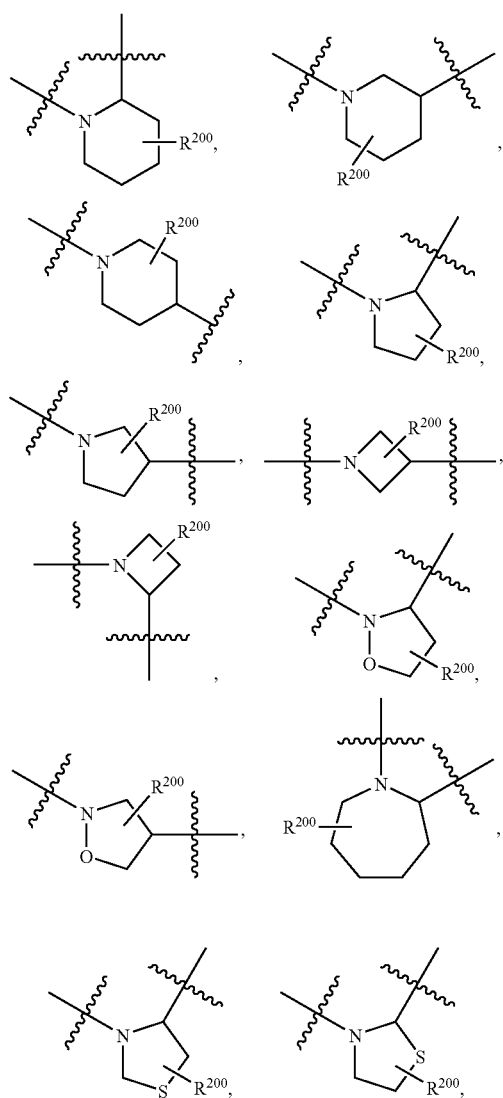

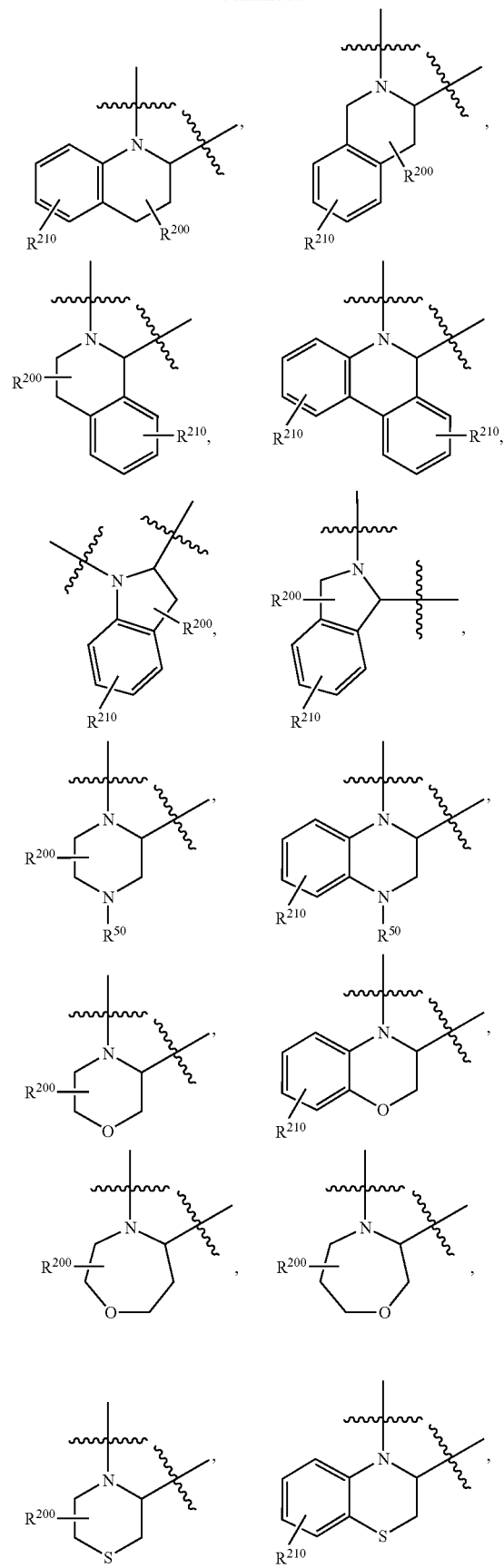

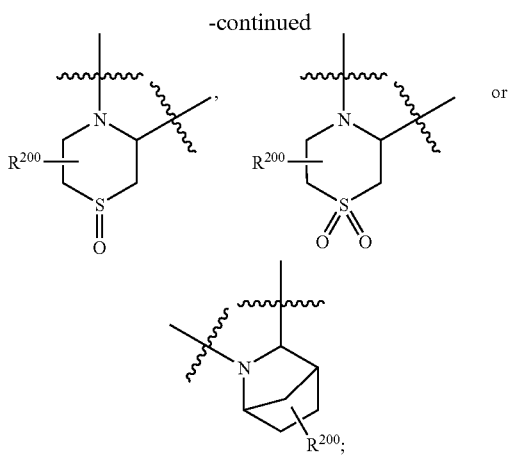

wherein

R$^{200}$ represents 0-4 substituents independently selected from the group consisting of F, Cl, —CF$_3$ and —O—CF$_3$, in particular F or CF$_3$, and/or two adjacent R$^{200}$ groups together form a fused aryl or heteroaryl group, in particular a benzo group;

R$^{210}$ represents 0-4 substituents independently selected from the group consisting of —O—C$_{1-3}$-alkyl, C$_{1-6}$-alkyl, F, Cl, Br, I, CF$_3$, OCF$_3$, OH, SH, phenyl, naphthyl, furyl, thienyl and pyridinyl, in particular from the group consisting of methyl, methoxy, CF$_3$, OCF$_3$, F, Cl and Br;

R$^{50}$ represents H, C$_{1-6}$-alkyl, —C(=O)—R$^{51}$, C$_{3-8}$-cycloalkyl, aryl, heteroaryl or a C$_{3-8}$-cycloalkyl, aryl or heteroaryl group bonded via a C$_{1-3}$-alkylene group, and R$^{51}$ represents C$_{1-6}$-alkyl, C$_{3-8}$-cycloalkyl, aryl, heteroaryl or a C$_{3-8}$-cycloalkyl, aryl or heteroaryl group bonded via a C$_{1-3}$-alkylene group.

In certain embodiments of the compounds according to the invention, R$^{200}$ and/or R$^{210}$ represent 0 substituents; that is to say are in each case absent.

In a similarly preferred embodiment of the compounds according to the invention, R$^2$ represents H, C$_{3-6}$-cycloalkyl, aryl, heteroaryl or a C$_{3-6}$-cycloalkyl, aryl or heteroaryl group bonded via a C$_{1-3}$-alkylene group; in each case unsubstituted or substituted one or more times by identical or different substituents. In particular, R$^2$ can represent H, methyl, ethyl, n-propyl, iso-propyl, n-butyl, iso-butyl, sec-butyl, tert-butyl or cyclopropyl, in each case unsubstituted or substituted one or more times by identical or different substituents selected from the group consisting of F, Cl, OH, OCH$_3$ and OCF$_3$, or R$^2$ represents phenyl or pyridyl, which is unsubstituted or substituted one or more times by identical or different substituents selected from the group consisting of C$_{1-6}$-alkyl-O—, F, Cl, Br, I, CF$_3$, OCF$_3$, OH and SH, in particular from methyl, methoxy, F, Cl, CF$_3$, or OCF$_3$, and wherein phenyl or pyridyl can be bonded via a C$_{1-3}$-alkylene group.

In a similarly preferred embodiment of the compounds according to the invention, R$^3$ represents H, F, Cl, —CF$_3$, —OH, C$_{1-6}$-alkyl, aryl; or an aryl group bonded via a C$_{1-3}$-alkylene group, in each case unsubstituted or substituted one or more times by identical or different substituents. In particular, R$^3$ can represent H, F, n-propyl, iso-propyl, n-butyl, iso-butyl, sec-butyl, tert-butyl, cyclopropyl, methoxy or ethoxy, in each case unsubstituted or substituted one or more times by identical or different substituents selected from the group consisting of F, Cl, OH, OCH$_3$ and OCF$_3$, or the R$^3$ represents phenyl or benzyl, wherein the aromatic in each case is unsubstituted or substituted one or more times by identical or different substituents chosen from C$_{1-6}$-alkyl, C$_{1-6}$-alkyl-O—, F, Cl, Br, I, CF$_3$, OCF$_3$, OH and SH, in particular from methyl, methoxy, F, Cl, CF$_3$, or OCF$_3$.

In similarly preferred embodiments of the compounds according to the invention, R$^{4a}$, R$^{4b}$, R$^{5a}$, R$^{5b}$, and/or R$^{6b}$, in each case independently of one another, represent H, F, Cl, —CF$_3$, OH, OCF$_3$, or O—C$_{1-6}$-alkyl, preferably H or F, in particular H.

In the compounds according to the invention, the following part structure

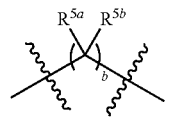

can preferably represent a —CH$_2$—, —(CH$_2$)$_2$—, —(CH$_2$)$_3$— or —(CH$_2$)$_4$— group.

Embodiments of the compounds according to the invention which are similarly preferred are those in which R$^8$ preferably represents H; C$_{1-6}$-alkyl; in particular methyl, ethyl, n-propyl, iso-propyl, n-butyl, iso-butyl, sec-butyl, tert-butyl; cyclopropyl, cyclobutyl, cyclopentyl, cyclohexyl, —CH$_2$CF$_3$, phenyl, benzyl, phenylethyl, phenylpropyl, or cyclopropyl, cyclobutyl, cyclopentyl, cyclohexyl bonded via a C$_{1-3}$-alkylene group, in each case unsubstituted or substituted one or more times by identical or different substituents. In particular, R$_8$ can represent H, methyl, ethyl, iso-propyl or cyclopropyl.

Embodiments of the compounds according to the invention which are similarly preferred are those in which R$^{9a}$ and R$^{9b}$ each independently represent H; F; methyl; ethyl, iso-propyl, CF$_3$, methoxy; cyclopropyl; phenyl; benzyl, phenylethyl or a cycloalkyl or —CF$_3$ bonded via a C$_{1-3}$-alkylene group, in each case unsubstituted or substituted one or more times by identical or different substituents. In particular, R$^{9a}$ and R$^{9b}$ represent H.

Embodiments of the compounds according to the invention which are similarly preferred are those in which the general formula (II) described above assumes the following part structure (IIa):

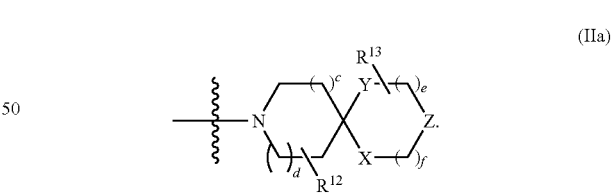

(IIa)

Embodiments of the compounds according to the invention which are similarly preferred are those in which the formula (III) described above assumes one of the following partial structures (IIIa) or (IIIb):

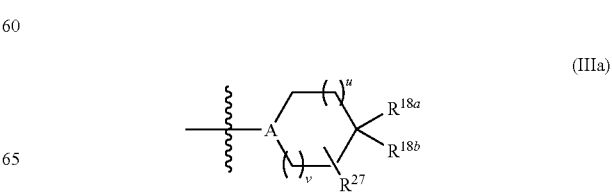

(IIIa)

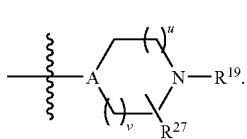
(IIIb)

Embodiments of the compounds according to the invention which are similarly preferred are those in which the part structure according to the formula (IIa) shown above assumes the following part structure (IIb):

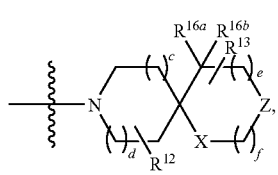
(IIb)

wherein in certain embodiments of these compounds of the invention $R^8$ represents H or $C_{1-6}$-alkyl, in each case unsubstituted or substituted one or more times by identical or different substituents, and $R^{9a}$ and $R^{9b}$ each represent H.

Embodiments of the compounds according to the invention which are similarly preferred are those compounds in which the partial structures according to the formulas (IIIa) and (IIIb) shown above assume one of the following partial structures (IIIc), (IIId) or (IIIe):

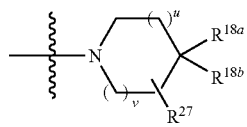
(IIIc)

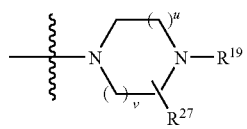
(IIId)

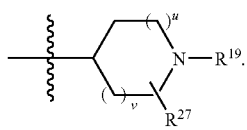
(IIIe)

In certain embodiments of these compounds according to the invention, s and t in each case represent 0.

Embodiments of the compounds according to the invention which are similarly preferred are those in which the partial structures according to the formulas (IIIa) and (IIIb) shown above assume one of the partial structures (IIIc) or (IIId) shown above and two of the substituents $R^{27}$ together represent a $C_{1-3}$-alkylene bridge, so that the ring represented in the part structure (IIIc) or (IIId) assumes a bicyclically bridged form. In certain embodiments of these compounds, s and t in each case=0.

Embodiments of the compounds according to the invention which are similarly preferred are those in which the partial structures according to the formulas (IIIa) and (IIIb) shown above assume one of the partial structures (IIIc) or (IIIe) similarly shown above, s represents 1 and t represents 1, 2 or 3. In certain embodiments of these compounds according to the invention, $R^8$ represents H, $C_{1-6}$-alkyl or $C_{3-6}$-cycloalkyl, in each case unsubstituted or substituted one or more times.

Further preferred embodiments of the compounds according to the invention are those in which the part structure according to the formula (IIb) shown above assumes the following part structure (IIc):

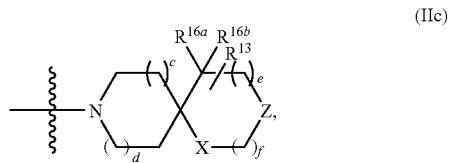
(IIc)

wherein in certain embodiments of these compounds, s and t in each case denote 0.

In further preferred embodiments of the compounds according to the invention, the particular structures according to the formulas (IIIc) or (IIId) shown above assume one of the following partial structures (IIIc) or (IIIg)

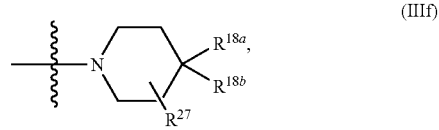
(IIIf)

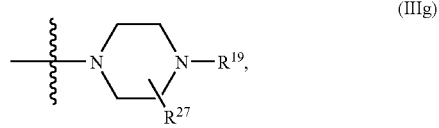
(IIIg)

wherein in certain embodiments of these compounds $R^{27}$ represents H and/or two of the substituents $R^{27}$ form a fused aryl or heteroaryl, in particular a benzo group.

Preferred embodiments of the compounds according to the invention are furthermore those compounds in which the partial structures IIIc or (IIId) shown above represent one of the following groups A to H:

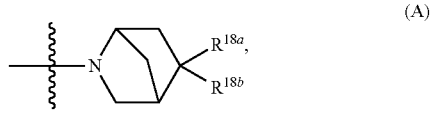
(A)

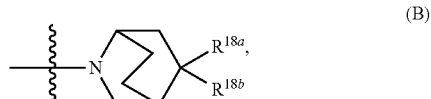
(B)

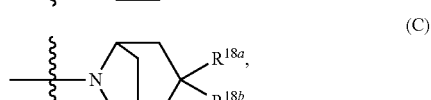
(C)

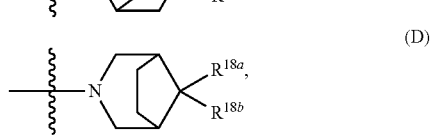
(D)

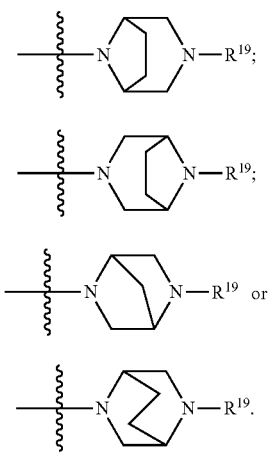

(E)

(F)

(G) or (H)

Persons skilled in the art understand that the presentation chosen for the groups A to H includes all possible stereoisomers of these groups in each case.

Further preferred embodiments of the compounds according to the invention are those compounds in which the partial structures (IIIc) or (IIIe) shown above represent a group according to one of the formulas (IIIh) or (IIIi)

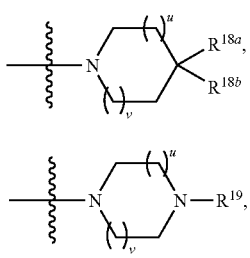

(IIIh)

(IIIi)

and $R^{9a}$ and $R^{9b}$ in each case represent H. In certain embodiments of these compounds u and v each independently represent 0 or 1. In particular, u and v both represent 1.

Further preferred embodiments of the compounds according to the invention are those compounds in which in the part structure (IIc) shown above, $R^{16a}$ and $R^{16b}$ in each case represent H or together form =O; $R^{13}$ represents H, aryl or heteroaryl and/or two of the substituents $R^{13}$ together form =O and/or two adjacent substituents $R^{13}$ together form a fused aryl or heteroaryl, in particular a benzo group, in each case unsubstituted or substituted one or more times by identical or different substituents.

Further preferred embodiments of the compounds according to the invention are those compounds in which in the partial structures according to the formulas (IIIf) or (IIIg) shown above:

$R^{18a}$ represents H; $C_{1-6}$-alkyl; $C_{3-8}$-cycloalkyl, —NH($C_{1-6}$alkyl), —N($C_{1-6}$alkyl)$_2$, phenyl, pyridyl, thienyl, pyrimidyl, thiazolyl, imidazolyl or triazolyl, in each case unsubstituted or substituted one or more times; phenyl, pyridyl, thienyl, pyrimidyl, thiazolyl, imidazolyl or triazolyl bonded via an —(O)$_{0-1}$—$C_{1-6}$-alkylene group, in each case unsubstituted or substituted one or more times; or $R^{18a}$ represents a group corresponding to formula VIIa

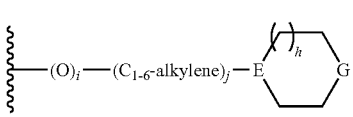

(VIIa)

wherein

I represents 0 or 1;

J represents 0 or 1;

H represents 0 or 1;

E represents N or CH; with the proviso that if i represents 1 and j represents 0, then E represents CH;

G represents $CR^{37a}R^{37b}$ or $NR^{38}$; wherein $R^{37a}$ and $R^{37b}$ each independently represent H, F or $C_{1-6}$-alkyl;

$R^{38}$ represents H; $C_{3-6}$-cycloalkyl or pyridyl, in particular pyridin-4-yl; and $R^{18b}$ represents H; OH; $C_{1-6}$-alkyl; phenyl, pyridyl, thienyl, thiazolyl, pyrimidyl, imidazolyl or triazolyl, in each case unsubstituted or substituted one or more times, phenyl, pyridyl, thienyl, thiazolyl, pyrimidyl, imidazolyl or triazolyl, O-phenyl or O-pyridyl bonded via a $C_{1-6}$-alkylene group, in each case unsubstituted or substituted one or more times by identical or different substituents; phenyl, pyridyl or thienyl bridged via $C_{1-6}$-alkylene-NH(C=O), in each case unsubstituted or substituted one or more times by identical or different substituents;

$R^{19}$ represents H; $C_{1-6}$-alkyl; $C_{3-8}$-cycloalkyl, or $C_{1-6}$-alkyl bonded via (C=O)$_{0-1}$; phenyl, pyridyl, thienyl, thiazolyl, triazolyl, pyrimidinyl or imidazolyl; in each case unsubstituted or substituted one or more times by identical or different substituents; phenyl, pyridyl, thienyl, thiazolyl, pyrimidinyl, triazolyl or imidazolyl bonded via a $C_{1-6}$-alkylene group; in each case unsubstituted or substituted one or more times by identical or different substituents; or $R^{19}$ represents a group corresponding to formula (VIIIa)

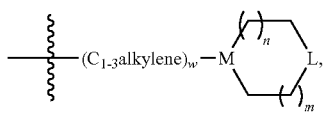

(VIIIa)

wherein w represents 0 or 1;

n represents 0 or 1;

m represents 0 or 1;

M represents CH or N, with the proviso that if w represents 0, M represents CH;

L represents $CR^{44a}R^{44b}$ or $NR^{45}$; wherein $R^{44a}$ and $R^{44b}$ each independently represent H, F or $C_{1-6}$-alkyl, in each case unsubstituted or substituted one or more times by identical or different substituents;

$R^{45}$ represents H; $C_{1-6}$-alkyl, $C_{3-6}$-alkyl or pyridyl, in each case unsubstituted or substituted one or more times by identical or different substituents.

Further preferred embodiments of the compounds according to the invention are those compounds in which in the partial structures according to formulas (IIIc) or (IIId) shown above represent one of the following groups A to H:

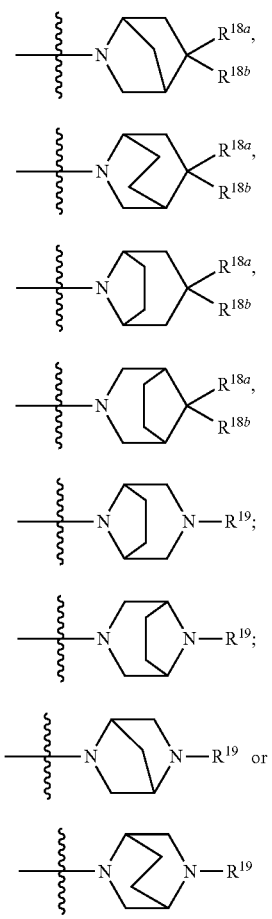

(A)
(B)
(C)
(D)
(E)
(F)
(G)
(H)

and wherein $R^{18a}$ represents H; $C_{1-6}$-alkyl; $C_{3-8}$-cycloalkyl, $N(C_{1-6}$-alkyl$)_2$; $NH(C_{1-6}$-alkyl); azetidinyl; pyrrolidinyl, piperidinyl, 4-($C_{1-6}$alkyl)-piperazinyl; phenyl or pyridyl, in each case unsubstituted or substituted one or more times by identical or different substituents; $N(C_{1-6}$-alkyl$)_2$; $NH(C_{1-6}$-alkyl); azetidinyl; pyrrolidinyl, piperidinyl, 4-($C_{1-6}$alkyl)-piperazinyl; phenyl, imidazolyl, triazolyl or pyridyl bonded via a —(O)$_{0-1}$—$C_{1-6}$-alkylene group, in each case unsubstituted or substituted one or more times by identical or different substituents;

$R^{18b}$ represents H; OH; $C_{1-6}$-alkyl; phenyl or pyridyl, in each case unsubstituted or substituted one or more times by identical or different substituents; phenyl or pyridyl bonded via a $C_{1-6}$-alkylene group, in each case unsubstituted or substituted one or more times by identical or different substituents; and $R^{19}$ represents H; $C_{1-6}$-alkyl; $C_{3-8}$-cycloalkyl, phenyl, pyridyl, thienyl, imidazolyl, thiazolyl or triazolyl, in each case unsubstituted or substituted one or more times by identical or different substituents; phenyl, pyridyl, thienyl, imidazolyl, thiazolyl, or triazolyl bonded via a $C_{1-6}$-alkylene group or a (C=O) group, in each case unsubstituted or substituted one or more times by identical or different substituents.

Further preferred embodiments of the compounds according to the invention are those compounds in which in the partial structures according to the formulas (IIIh) or (IIIi) shown above:

$R^{18a}$ represents H; $C_{1-6}$-alkyl; $C_{3-8}$-cycloalkyl, $N(C_{1-6}$-alkyl$)_2$; $NH(C_{1-6}$-alkyl), azetidinyl; pyrrolidinyl, piperidinyl, 4-($C_{1-6}$alkyl)-piperazinyl; phenyl or pyridyl, in each case unsubstituted or substituted one or more times by identical or different substituents; $N(C_{1-6}$-alkyl$)_2$; $NH(C_{1-6}$-alkyl), azetidinyl; pyrrolidinyl, piperidinyl, 4-($C_{1-6}$alkyl)-piperazinyl; phenyl, imidazolyl, triazolyl, or pyridyl bonded via a —(O)$_{0/1}$—$C_{1-6}$-alkylene group, in each case unsubstituted or substituted one or more times by identical or different substituents;

$R^{18b}$ represents H; OH; $C_{1-6}$-alkyl; phenyl or pyridyl, in each case unsubstituted or substituted one or more times by identical or different substituents; phenyl or pyridyl bonded via a $C_{1-6}$-alkylene group, in each case unsubstituted or substituted one or more times by identical or different substituents; and $R^{19}$ represents H; $C_{1-6}$-alkyl; $C_{3-8}$-cycloalkyl, phenyl, pyridyl, thienyl, imidazolyl, thiazolyl, or triazolyl, in each case unsubstituted or substituted one or more times by identical or different substituents; phenyl or pyridyl bonded via a $C_{1-6}$-alkylene group or (C=O) group, in each case unsubstituted or substituted one or more times by identical or different substituents.

Further preferred embodiments of the compounds according to the invention are those compounds in which the partial structure according to formula IIc shown above can assume one of the following partial structures SP:

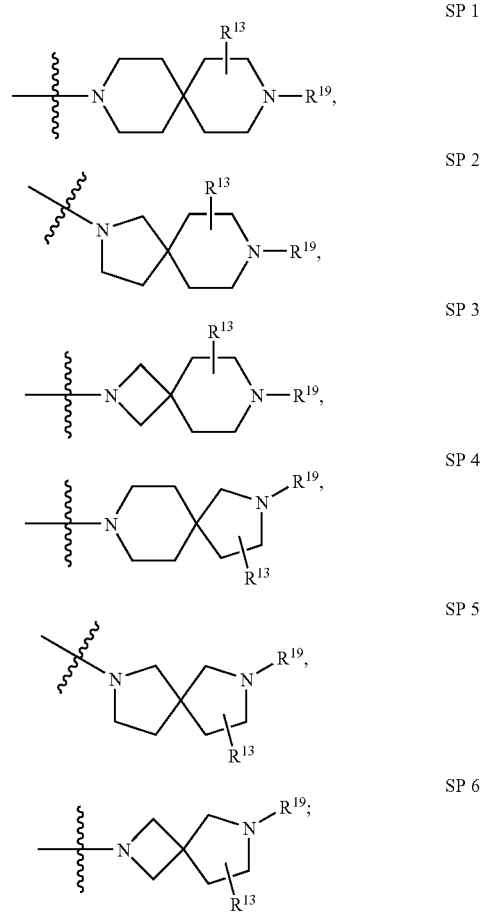

SP 1
SP 2
SP 3
SP 4
SP 5
SP 6

SP 7 – SP 29: chemical structure diagrams (spiro heterocyclic substituent groups).

-continued

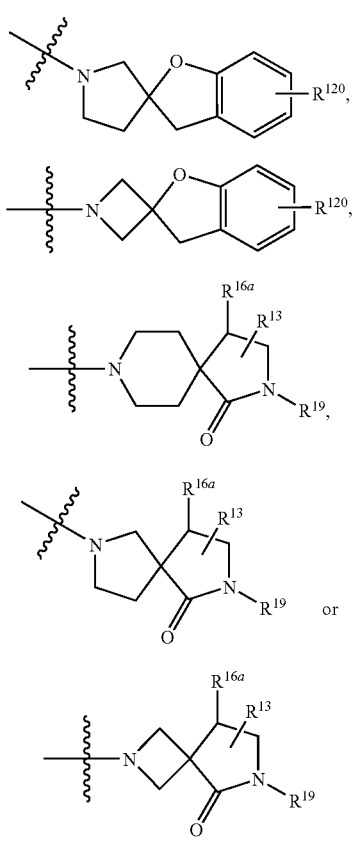

SP 30

SP 31

SP 32

SP 33 or

SP 34 wherein $R^{13}$ represents H or phenyl, unsubstituted or substituted one or more times by identical or different substituents; and/or two $R^{13}$ substituents together form =O and/or two adjacent substituents $R^{13}$ together form a fused aryl or heteroaryl group, in particular a benzo group, in each case unsubstituted or substituted one or more times by identical or different substituents, $R^{15}$ represents H; $C_{1-6}$-alkyl; $C_{3-8}$-cycloalkyl, phenyl, pyridyl, in each case unsubstituted or substituted one or more times by identical or different substituents; phenyl or pyridyl bonded via a $C_{1-6}$-alkylene group, in each case unsubstituted or substituted one or more times by identical or different substituents;

$R^{16a}$ represents H, $C_{1-6}$-alkyl, phenyl or pyridyl, in each case unsubstituted or substituted one or more times by identical or different substituents;

$R^{18a}$ represents H; $C_{1-6}$-alkyl; $C_{3-8}$-cycloalkyl, $N(C_{1-6}$-alkyl$)_2$; $NH(C_{1-6}$-alkyl), azetidinyl; pyrrolidinyl, piperidinyl, 4-($C_{1-6}$alkyl)-piperazinyl; phenyl or pyridyl, in each case unsubstituted or substituted one or more times by identical or different substituents; $N(C_{1-6}$-alkyl$)_2$; $NH(C_{1-6}$-alkyl), azetidinyl; pyrrolidinyl, piperidinyl, 4-($C_{1-6}$alkyl)-piperazinyl; phenyl, imidazolyl, triazolyl, or pyridyl bonded via a —(O)$_{0/1}$—$C_{1-6}$-alkylene group, in each case unsubstituted or substituted one or more times by identical or different substituents;

$R^{18b}$ represents H; OH; $C_{1-6}$-alkyl; phenyl or pyridyl, in each case unsubstituted or substituted one or more times by identical or different substituents; phenyl or pyridyl bonded via a $C_{1-6}$-alkylene group, in each case unsubstituted or substituted one or more times by identical or different substituents;

$R^{19}$ represents H; $C_{1-6}$-alkyl; $C_{3-8}$-cycloalkyl, phenyl, pyridyl, thienyl, imidazolyl, thiazolyl, or triazolyl, in each case unsubstituted or substituted one or more times by identical or different substituents; phenyl or pyridyl bonded via a $C_{1-6}$-alkylene group or (C=O) group, in each case unsubstituted or substituted one or more times by identical or different substituents;

$R^{120}$ represents H; F; Cl; OH; $OCH_3$, O—$CF_3$, $C_{1-6}$-alkyl; $CF_3$, phenyl, unsubstituted or substituted one or more times;

$R^{126}$ represents H; $C_{1-6}$-alkyl; $C_{3-6}$cycloalkyl; phenyl or pyridyl; $C_{3-6}$-cycloalkyl, phenyl or pyridyl bonded via a $C_{1-3}$-alkylene group, in each case unsubstituted or substituted one or more times by identical or different substituents.

Further preferred embodiments of compounds according to the invention are those compounds in which in formula I shown above the following part structure (B):

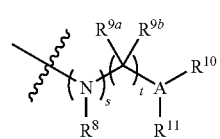

(B)

is one of the following partial structures B.1. to B.47:

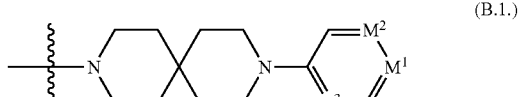

(B.1.)

(B.2.)

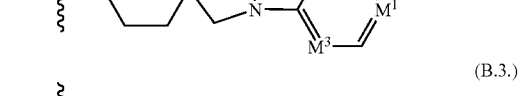

(B.3.)

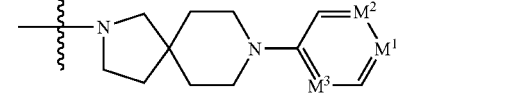

(B.4)

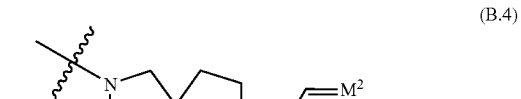

(B.5.)

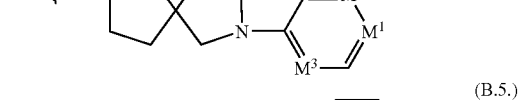

(B.6.)

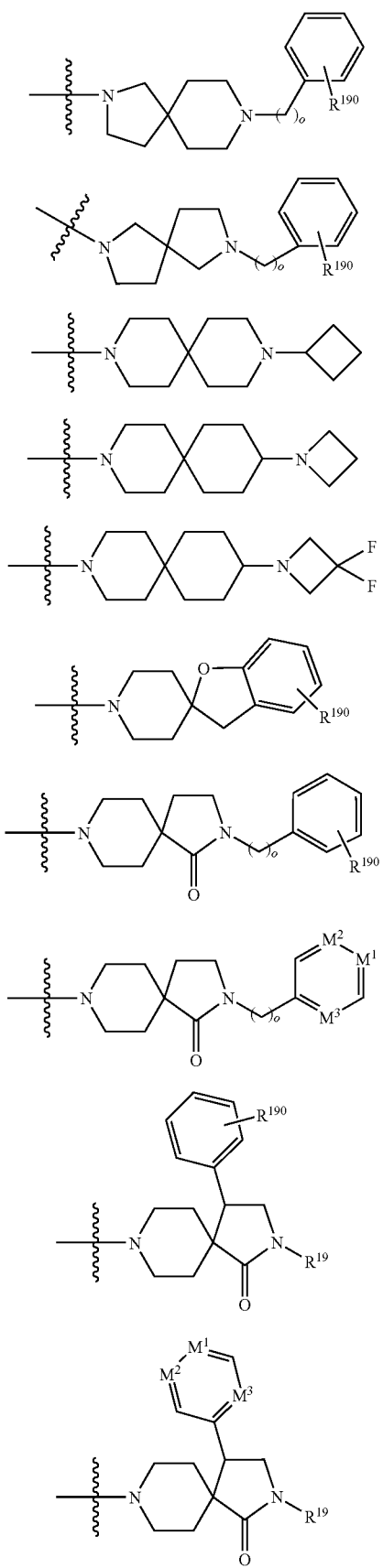
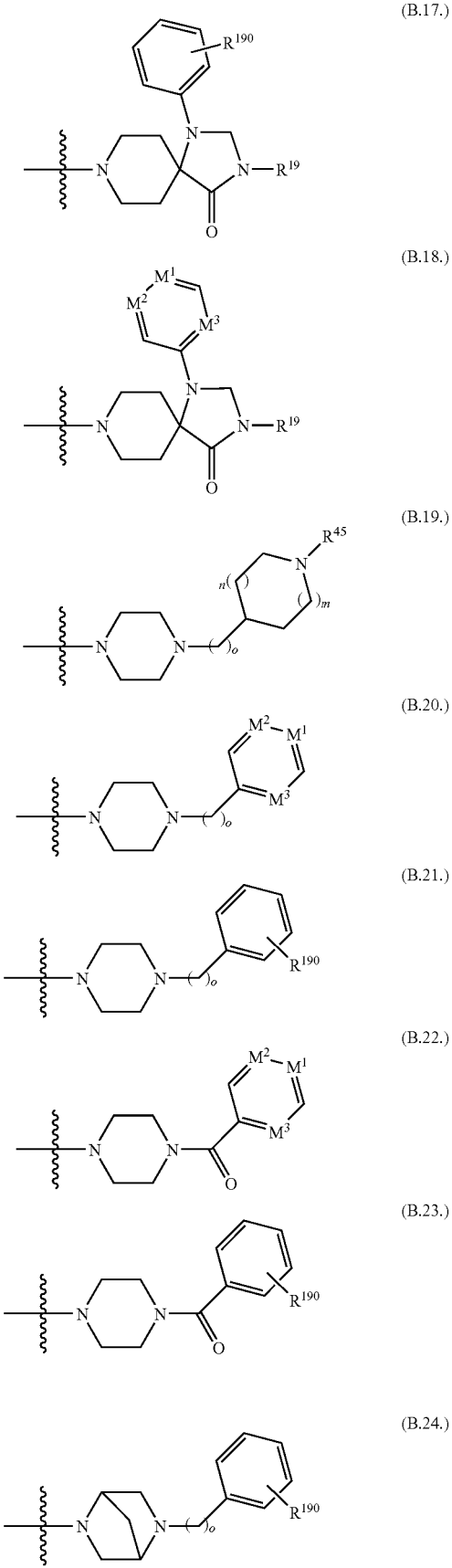

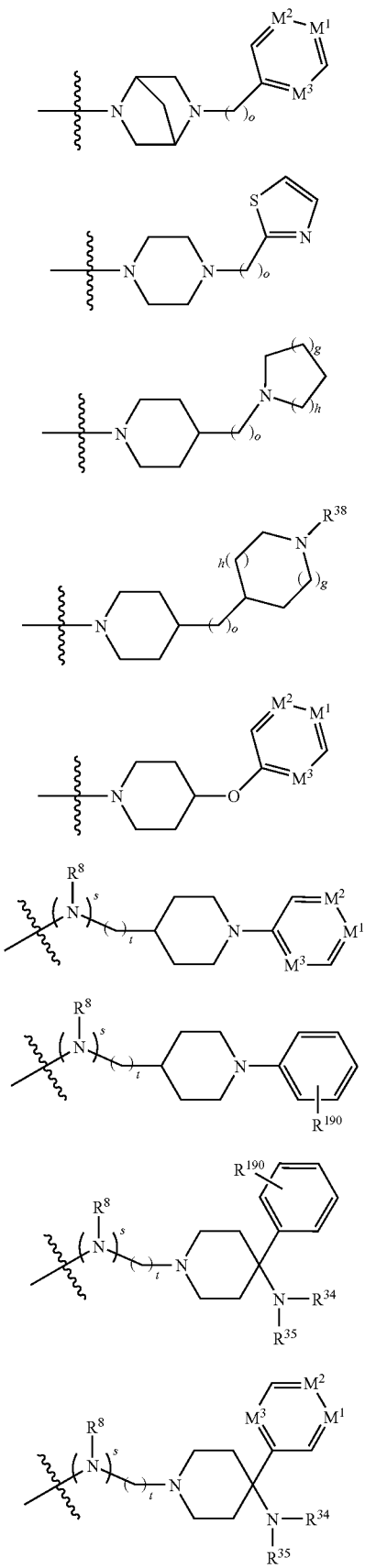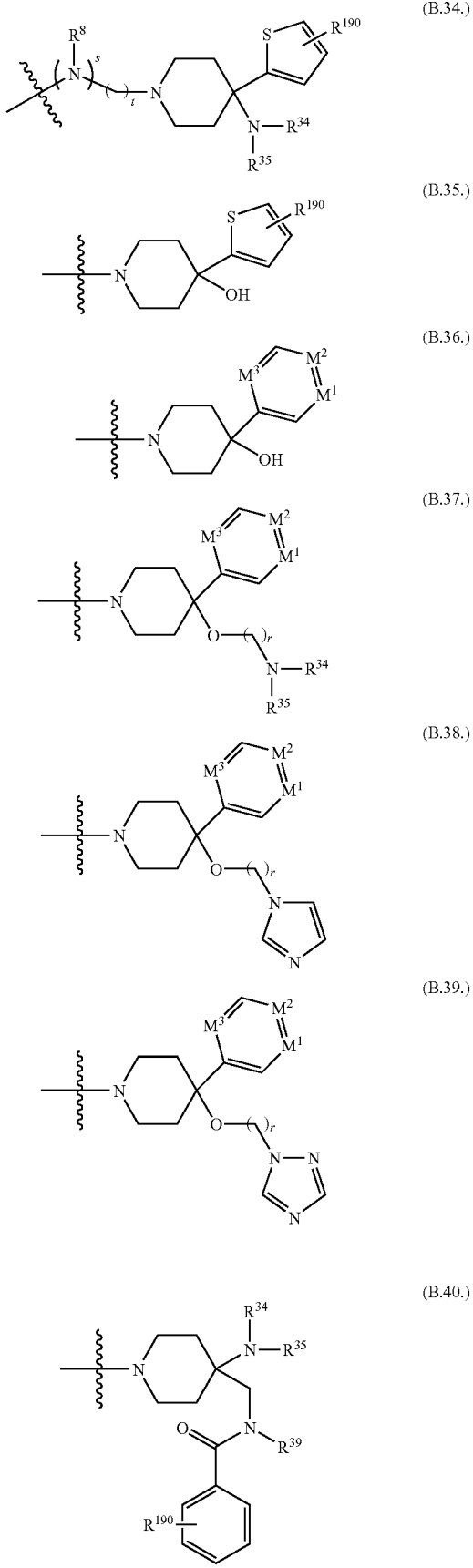

-continued

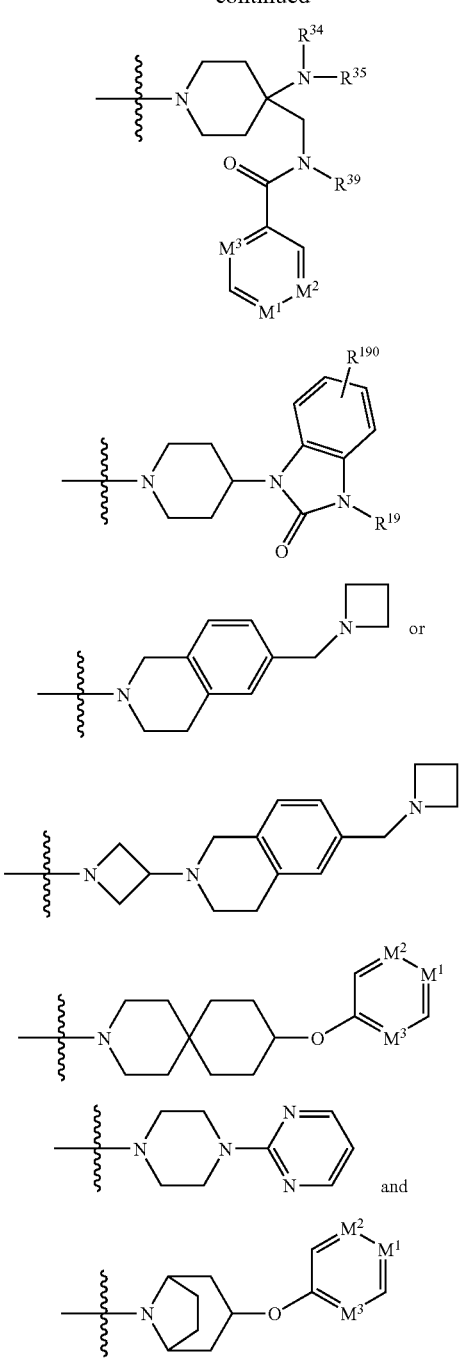

(B.41.)

(B.42.)

(B.43.)

(B.44.)

(B.45.)

(B.46.)

(B.47.)

wherein
h=0 or 1;
g=0 or 1;
m=0 or 1;
n=0 or 1;
o=1, 2 or 3;
r=1, 2 or 3, in particular 1 or 2;
s=0 or 1;
t=0, 1, 2 or 3, in particular 0, 1, or 2, with the proviso that if s is 0, then t likewise is 0;
$M^1$, $M^2$ and $M^3$ each independently represent N or CH, wherein one variable from $M^1$, $M^2$ and $M^3$ represents N, and the others both represent CH;

$R^8$ represents H; $C_{1-6}$alkyl, in particular methyl, ethyl, n-propyl, iso-propyl, n-butyl, sec-butyl, iso-butyl and tert-butyl; $C_{3-6}$cycloalkyl, in particular cyclopropyl, in each case unsubstituted or substituted one or more times by identical or different substituents;

$R^{19}$ is selected from H; $C_{1-6}$alkyl, in particular methyl, ethyl, n-propyl, iso-propyl, n-butyl, sec-butyl, iso-butyl and tert-butyl; $C_{3-6}$cycloalkyl, in particular cyclopropyl; in each case unsubstituted or substituted one or more times by identical or different substituents;

$R^{34}$ and $R^{35}$ preferably independently of one another are methyl or ethyl or, together with the N atom joining them, form an azetidinyl, pyrrolidinyl, piperidinyl, 4-($C_{1-6}$alkyl)-piperazinyl group, in each case unsubstituted or substituted one or more times by identical or different substituents;

$R^{38}$ represents H, $C_{1-6}$-alkyl; $C_{3-6}$-cycloalkyl, or pyridyl;

$R^{39}$ is selected from H; $C_{1-6}$alkyl, in particular methyl, ethyl, n-propyl, iso-propyl, n-butyl, sec-butyl, iso-butyl and tert-butyl; $C_{3-6}$cycloalkyl, in particular cyclopropyl, in each case unsubstituted or substituted one or more times by identical or different substituents;

$R^{45}$ represents H, $C_{1-6}$-alkyl, $C_{3-6}$-cycloalkyl or pyridyl; and $R^{190}$ represents 0-4 substituents each independently selected from the group consisting of F, Cl, 0-$CF_3$, $CF_3$ and CN.

In certain embodiments of the compounds according to the invention which contain one of the partial structures B.1. to B.46. described above, $R^8$, $R^{9a}$, $R^{9b}$, $R^{19}$ and $R^{39}$ each independently denote H or methyl.

In the partial structures B.5., B.6., B.7., B.8., B.13., B.14., B.19., B.20., B.21., B.24., B. 25. and B.26. shown above, o preferably represents 0 or 1; in the partial structures B.27. and B.28. o preferably represents 1 or 2.

In the partial structures shown above, $R^{190}$, if it is bonded to a phenyl group, preferably represents a substituent which is selected from the group consisting of F, $CF_3$ and CN and which is preferably bonded to the phenyl ring in the 3 or 4 position.

Further embodiments of the compounds according to the invention are those which are represented by the following formulas $C_1$-$C_{13}$:

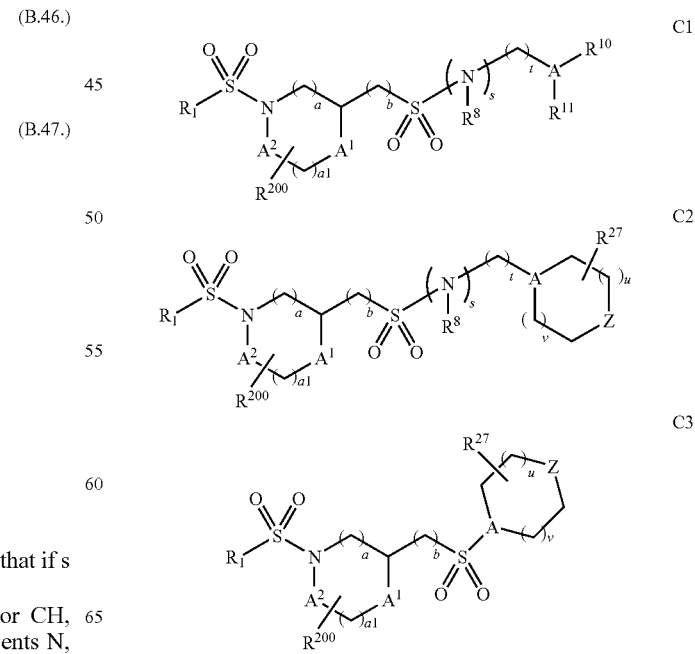

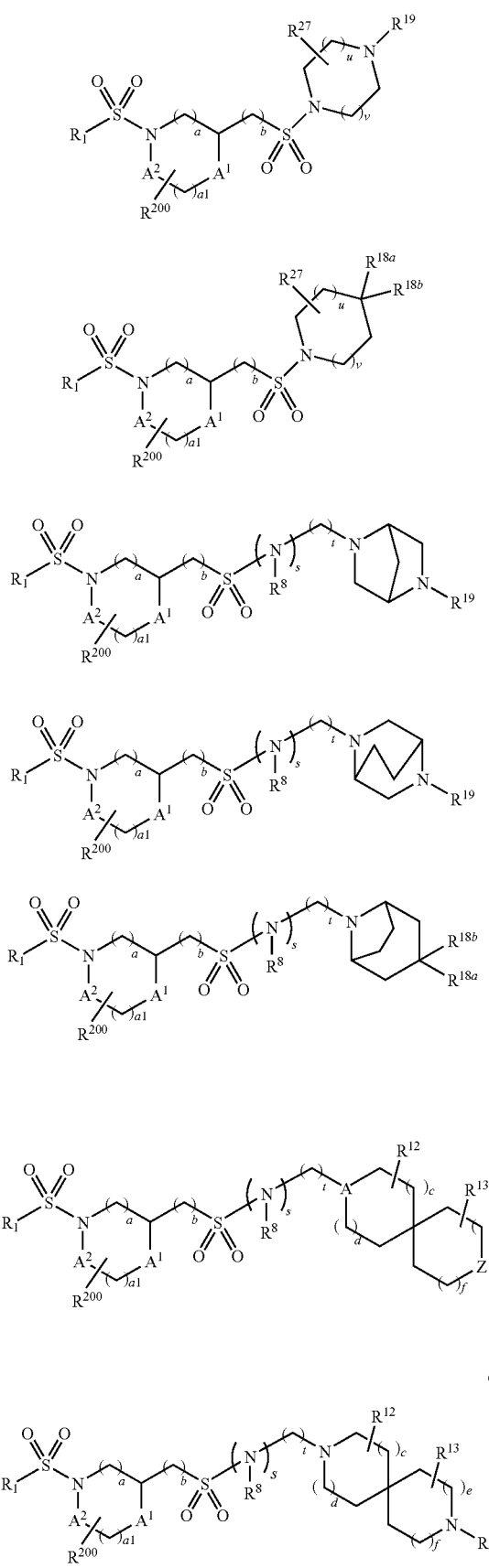

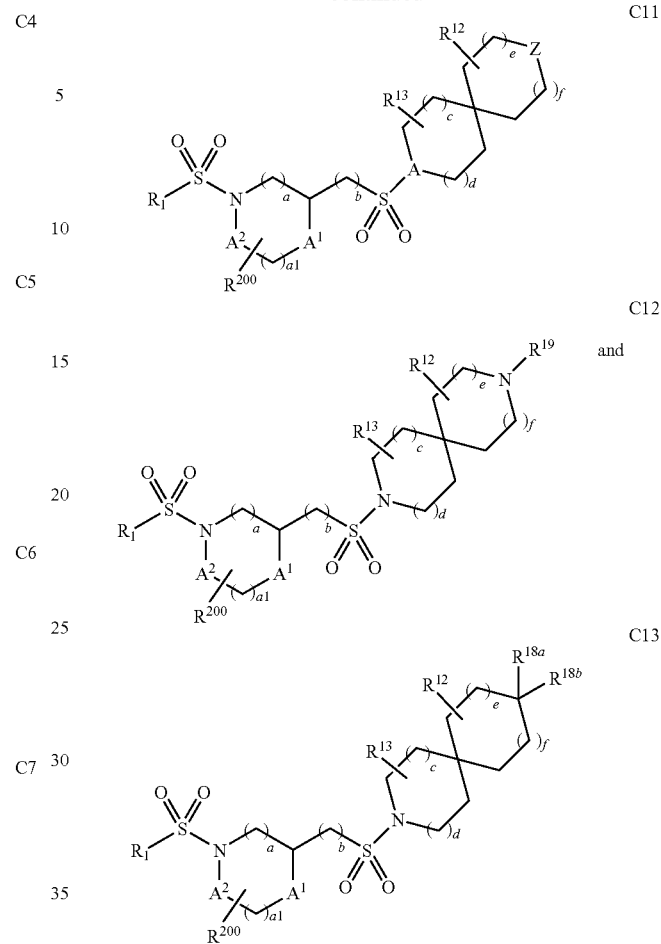

wherein
a represents 0, 1 or 2,
a1 represents 0, 1 or 2,
$A^1$ represents $CH_2$, O or $NR^{50}$
$A^2$ represents $CH_2$, O or $NR^{50}$
b represents 1, 2, 3 or 4;
and the other substituent groups, variables and indices have the meanings described herein in connection with the compounds according to the invention and preferred embodiments thereof.

In preferred embodiments of the compounds according to the invention, these are compounds corresponding to the foregoing formulas C1 to C13 wherein, if present in the particular general formula,
a represents 0, 1 or 2,
a1 represents 0, 1 or 2,
$A^1$ represents $CH_2$, O or $NR^{50}$
$A^2$ represents $CH_2$, O or $NR^{50}$
b represents 1, 2, 3 or 4
c, d, e and f, in each case independently of one another, represent 0 or 1
s represents 1,
t represents 1, 2 or 3,
u and v each independently represent 0 or 1;
$R^1$ represents phenyl or naphthyl, wherein the phenyl or naphthyl is unsubstituted or substituted one or more times, for example 2, 3, 4 or 5 times, by identical or different substituents selected from the group consisting of methyl, methoxy, $CF_3$, $OCF_3$, F, Cl and Br;

R⁸ represents H, methyl, ethyl, n-propyl, iso-propyl, n-butyl, iso-butyl, sec-butyl, tert-butyl, cyclopropyl, cyclobutyl, phenyl, benzyl, phenylethyl, phenylpropyl, or cyclopropyl bonded via a $C_{1-3}$-alkylene group, in each case unsubstituted or substituted one or more times by identical or different substituents;

$R^{12}$ is absent or represents 1, 2, 3 or 4 substituents selected from F and methyl;

$R^{13}$ and $R^{27}$ each independently are absent or represent 1, 2, 3 or 4 substituents selected from F and methyl or represent a fused benzo group which is unsubstituted or substituted one or more times by identical or different substituents;

$R^{18a}$ represents H; $C_{1-6}$-alkyl; $C_{3-8}$-cycloalkyl, $N(C_{1-6}$-alkyl$)_2$; $NH(C_{1-6}$-alkyl), azetidinyl; pyrrolidinyl, piperidinyl, 4-($C_{1-6}$alkyl)-piperazinyl; phenyl or pyridyl, in each case unsubstituted or substituted one or more times; $N(C_{1-6}$-alkyl$)_2$; $NH(C_{1-6}$-alkyl), azetidinyl; pyrrolidinyl, piperidinyl, 4-($C_{1-6}$)-piperazinyl; phenyl, imidazolyl, triazolyl, or pyridyl bonded via a $-(O)_{0/1}-C_{1-6}$-alkylene group, in each case unsubstituted or substituted one or more times;

$R^{18b}$ represents H; OH; $C_{1-6}$-alkyl; phenyl, pyridyl, thienyl or thiazolyl in each case unsubstituted or substituted one or more times, phenyl, pyridyl, O-phenyl, O-pyridyl, thienyl or thiazolyl bonded via a $C_{1-6}$-alkylene group, in each case unsubstituted or substituted one or more times; phenyl, pyridyl or thienyl bridged via $C_{1-6}$-alkylene-NH(C=O), in each case unsubstituted or substituted one or more times;

$R^{19}$ represents H; $C_{1-6}$-alkyl; $C_{3-8}$-cycloalkyl, piperidinyl, or $C_{1-6}$-alkyl bonded via (C=O)$_{0-1}$; phenyl, pyridyl, thienyl, thiazolyl, triazolyl, pyrimidinyl or imidazolyl; in each case unsubstituted or substituted one or more times; phenyl, pyridyl, thienyl, thiazolyl, pyrimidinyl, triazolyl or imidazolyl bonded via a $C_{1-6}$-alkylene group; in each case unsubstituted or substituted one or more times;

$R^{200}$ represents 0-4 substituents each independently selected from the group consisting of F, Cl, —CF$_3$ and —O—CF$_3$, in particular F or CF$_3$, and/or two adjacent $R^{200}$ groups together form a fused aryl or heteroaryl group, in particular a benzo group.

In embodiments of the compounds according to the invention corresponding to the foregoing formulas C1 to C13 which are furthermore preferred, the following combinations are met, namely a represents 0, $A^1$ represents CH$_2$, a1 represents 0 and $A^2$ represents CH$_2$;

a represents 0, $A^1$ represents CH$_2$, a1 represents 1 and $A^2$ represents CH$_2$;

a represents 1, $A^1$ represents CH$_2$, a1 represents 0 and $A^2$ represents CH$_2$;

a represents 1, $A^1$ represents CH$_2$, a1 represents 0 and $A^2$ represents 0;

a represents 0, $A^1$ represents CH$_2$, a1 represents 2 and $A^2$ represents CH$_2$;

a represents 1, $A^1$ represents CH$_2$, a1 represents 1 and $A^2$ represents CH$_2$, or a represents 2, $A^1$ represents CH$_2$, a1 represents 0 and $A^2$ represents CH$_2$.

In a further preferred embodiment of the present invention, the substituted compounds according to the invention are selected from the group consisting of:

1  1-(2-(1-(Mesitylsulfonyl)pyrrolidin-3-yl)ethylsulfonyl)-4-(2-(pyrrolidin-1-yl)ethyl)piperidine
2  (R)-1-(3-(1-(Naphthalen-2-ylsulfonyl)pyrrolidin-2-yl)propylsulfonyl)-4-(pyridin-4-yl)piperazine hydrochloride
3  1-(2-(1-(Benzo[b]thiophen-3-ylsulfonyl)pyrrolidin-3-yl)ethylsulfonyl)-4-(2-(pyrrolidin-1-yl)ethyl)piperidine
4  (S)-1-(3-(1-(Mesitylsulfonyl)azetidin-2-yl)propylsulfonyl)-4-(2-(pyrrolidin-1-yl)ethyl)piperidine hydrochloride
5  1-(1-Methylpiperidin-4-yl)-4-(4-(1-(naphthalen-1-ylsulfonyl)pyrrolidin-2-yl)butylsulfonyl)piperazine dihydrochloride
6  1-(4-(1-(Mesitylsulfonyl)pyrrolidin-2-yl)butylsulfonyl)-4-(2-(pyrrolidin-1-yl)ethyl)piperidine
7  1-(4-(1-(4-Methoxy-2,3,6-trimethylphenylsulfonyl)pyrrolidin-2-yl)butylsulfonyl)-4-(1-methylpiperidin-4-yl)piperazine
8  1-(4-(1-(4-Methoxy-2,3,6-trimethylphenylsulfonyl)pyrrolidin-2-yl)butylsulfonyl)-4-(2-(pyrrolidin-1-yl)ethyl)piperidine
9  1-(4-(1-(2,6-Dichloro-4-(trifluoromethyl)phenylsulfonyl)pyrrolidin-2-yl)butylsulfonyl)-4-(1-methylpiperidin-4-yl)piperazine
10 1-(4-Methoxy-2,3,6-trimethylphenylsulfonyl)-3-(3-(4-(2-(pyrrolidin-1-yl)ethyl)piperidin-1-ylsulfonyl)propyl)piperidine hydrochloride
11 1-(Mesitylsulfonyl)-3-(3-(4-(2-(pyrrolidin-1-yl)ethyl)piperidin-1-ylsulfonyl)propyl)piperidine hydrochloride
12 1-(Mesitylsulfonyl)-4-(3-(4-(2-(pyrrolidin-1-yl)ethyl)piperidin-1-ylsulfonyl)propyl)piperidine
13 1-(3-(1-(Mesitylsulfonyl)piperidin-4-yl)propylsulfonyl)-4-(1-methylpiperidin-4-yl)piperazine
14 1-(2,6-Dichloro-4-(trifluoromethyl)phenylsulfonyl)-4-(2-(4-(2-(pyrrolidin-1-yl)ethyl)piperidin-1-ylsulfonyl)ethyl)piperidine
16 1-(2-(1-(4-Methoxy-2,3,6-trimethylphenylsulfonyl)pyrrolidin-3-yl)ethylsulfonyl)-4-(2-(pyrrolidin-1-yl)ethyl)piperidine hydrochloride
17 1-(2-(1-(2,3-Dichlorophenylsulfonyl)pyrrolidin-3-yl)ethylsulfonyl)-4-(2-(pyrrolidin-1-yl)ethyl)piperidine hydrochloride
18 4-(2-(Pyrrolidin-1-yl)ethyl)-1-(2-(1-(2,4,5-trichlorophenylsulfonyl)pyrrolidin-3-yl)ethylsulfonyl)piperidine hydrochloride
19 1-(2-(1-(4-Chloro-2,5-dimethylphenylsulfonyl)pyrrolidin-3-yl)ethylsulfonyl)-4-(2-(pyrrolidin-1-yl)ethyl)piperidine
20 1-(2-(1-(Mesitylsulfonyl)pyrrolidin-3-yl)ethylsulfonyl)-4-(pyridin-4-yl)piperazine hydrochloride
21 1-(2-(1-(2,3-Dichlorophenylsulfonyl)pyrrolidin-3-yl)ethylsulfonyl)-4-(pyridin-4-yl)piperazine hydrochloride
22 1-(2-(1-(4-Methoxy-2,3,6-trimethylphenylsulfonyl)pyrrolidin-3-yl)ethylsulfonyl)-4-(pyridin-4-yl)piperazine
23 1-(2-(1-(4-Chloro-2,5-dimethylphenylsulfonyl)pyrrolidin-3-yl)ethylsulfonyl)-4-(pyridin-4-yl)piperazine
24 1-(2-(1-(3,4-Dichlorophenylsulfonyl)pyrrolidin-3-yl)ethylsulfonyl)-4-(pyridin-4-yl)piperazine hydrochloride
25 1-(2-(1-(4-Methoxy-2,6-dimethylphenylsulfonyl)pyrrolidin-3-yl)ethylsulfonyl)-4-(2-(pyrrolidin-1-yl)ethyl)piperidine hydrochloride
26 1-(3-(1-(4-Methoxy-2,6-dimethylphenylsulfonyl)piperidin-2-yl)propylsulfonyl)-4-(1-methylpiperidin-4-yl)piperazine
27 (S)-1-(3-(1-(2-Chloro-6-methylphenylsulfonyl)pyrrolidin-2-yl)propylsulfonyl)-4-(1-methylpiperidin-4-yl)piperazine
28 (S)-1-(1-Methylpiperidin-4-yl)-4-(3-(1-(2,4,6-trichlorophenylsulfonyl)pyrrolidin-2-yl)propylsulfonyl)piperazine
29 (S)-1-(3-(1-(4-Cloro-2,5-dimethylphenylsulfonyl)pyrrolidin-2-yl)propylsulfonyl)-4-(1-methylpiperidin-4-yl)piperazine
30 (S)-1-(1-Methylpiperidin-4-yl)-4-(3-(1-(naphthalen-1-ylsulfonyl)pyrrolidin-2-yl)propylsulfonyl)piperazine
31 (S)-1-(3-(1-(2,4-Dichlorophenylsulfonyl)pyrrolidin-2-yl)propylsulfonyl)-4-(1-methylpiperidin-4-yl)piperazine
32 (S)-1-(3-(1-(4-Methoxy-2,6-dimethylphenylsulfonyl)pyrrolidin-2-yl)propylsulfonyl)-4-(1-methylpiperidin-4-yl)piperazine
33 (S)-1-(3-(1-(2,2-Diphenylethylsulfonyl)pyrrolidin-2-yl)propylsulfonyl)-4-(1-methylpiperidin-4-yl)piperazine
34 (R)-1-(3-(1-(4-Methoxy-2,6-dimethylphenylsulfonyl)pyrrolidin-2-yl)propylsulfonyl)-4-(1-methylpiperidin-4-yl)piperazine
35 (S)-1-(1-Methylpiperidin-4-yl)-4-(3-(1-(3-(trifluoromethyl)phenylsulfonyl)pyrrolidin-2-yl)propylsulfonyl)piperazine
36 4-(1-(3-((2R,4S)-4-Fluoro-1-(4-methoxy-2,6-dimethylphenylsulfonyl)pyrrolidin-2-yl)propylsulfonyl)piperidin-4-yloxy)pyridine
37 1-(1-Methylpiperidin-4-yl)-4-((1-(3-(trifluoromethyl)phenylsulfonyl)piperidin-2-yl)methylsulfonyl)piperazine
38 1-(2-(1-(4-Chloro-2,5-dimethylphenylsulfonyl)piperidin-2-yl)ethylsulfonyl)-4-(1-methylpiperidin-4-yl)piperazine dihydrochloride
39 1-(4-Methoxy-2,3,6-trimethylphenylsulfonyl)-3-(2-(4-(2-(pyrrolidin-1-yl)ethyl)piperidin-1-ylsulfonyl)ethyl)piperidine hydrochloride
40 (S)-2-(4-(3-(1-(4-Methoxy-2,3,6-trimethylphenylsulfonyl)pyrrolidin-2-yl)propylsulfonyl)piperazin-1-yl)thiazole -continued 41 (R)-1-(3-(1-(Mesitylsulfonyl)pyrrolidin-2-yl)propylsulfonyl)-4-(1-methylpiperidin-4-yl)piperazine dihydrochloride
42 1-(4-(1-(Mesitylsulfonyl)pyrrolidin-2-yl)butylsulfonyl)-4-(1-methylpiperidin-4-yl)piperazine dihydrochloride
43 3-((4-(2-(1-(4-Chloro-2,5-dimethylphenylsulfonyl)pyrrolidin-3-yl)ethylsulfonyl)piperazin-1-yl)methyl)benzonitrile hydrochloride
44 1-(3-(1-(4-Methoxy-2,6-dimethylphenylsulfonyl)indolin-2-yl)propylsulfonyl)-4-(pyridin-3-yl)piperidin-4-ol
45 1-(4-Methoxy-2,6-dimethylphenylsulfonyl)-2-(3-(9-(pyridin-4-yl)-3,9-diazaspiro[5.5]undecan-3-ylsulfonyl)propyl)indoline
46 (S)-4-(1-(3-(1-(2-Chloro-6-methylphenylsulfonyl)pyrrolidin-2-yl)propylsulfonyl)piperidin-4-yloxy)pyridine
47 (S)-4-(1-(3-(1-(4-Methoxy-2,6-dimethylphenylsulfonyl)pyrrolidin-2-yl)propylsulfonyl)piperidin-4-yloxy)pyridine
48 (S)-4-(1-(3-(1-(2-(Trifluoromethyl)phenylsulfonyl)pyrrolidin-2-yl)propylsulfonyl)piperidin-4-yloxy)pyridine
49 (S)-4-(1-(3-(1-(Naphthalen-2-ylsulfonyl)pyrrolidin-2-yl)propylsulfonyl)piperidin-4-yloxy)pyridine
50 (S)-4-(1-(3-(1-(Naphthalen-1-ylsulfonyl)pyrrolidin-2-yl)propylsulfonyl)piperidin-4-yloxy)pyridine
51 (S)-4-(1-(3-(1-(2,4-Dichlorophenylsulfonyl)pyrrolidin-2-yl)propylsulfonyl)piperidin-4-yloxy)pyridine
52 (S)-4-(1-(3-(1-(2,3-Dichlorophenylsulfonyl)pyrrolidin-2-yl)propylsulfonyl)piperidin-4-yloxy)pyridine
53 (S)-4-(1-(3-(1-(4-Chloro-2,5-dimethylphenylsulfonyl)pyrrolidin-2-yl)propylsulfonyl)piperidin-4-yloxy)pyridine
54 (1R,3R,5S)-8-(3-((S)-1-(4-Methoxy-2,6-dimethylphenyl-sulfonyl)pyrrolidin-2-yl)propylsulfonyl)-3-(pyridin-4-yloxy)-8-azabicyclo[3.2.1]octane
55 (1R,3R,5S)-8-(3-((S)-1-(2-Chloro-6-methylphenylsulfonyl)pyrrolidin-2-yl)propylsulfonyl)-3-(pyridin-4-yloxy)-8-azabicyclo[3.2.1]octane
56 (1R,3R,5S)-3-(Pyridin-4-yloxy)-8-(3-((S)-1-(2-(trifluoromethyl)phenylsulfonyl)pyrrolidin-2-yl)propylsulfonyl)-8-azabicyclo[3.2.1]octane
57 (1R,3R,5S)-8-(3-((S)-1-(Naphthalen-2-ylsulfonyl)pyrrolidin-2-yl)propylsulfonyl)-3-(pyridin-4-yloxy)-8-azabicyclo[3.2.1]octane
58 (1R,3R,5S)-8-(3-((S)-1-(Naphthalen-1-ylsulfonyl)pyrrolidin-2-yl)propylsulfonyl)-3-(pyridin-4-yloxy)-8-azabicyclo[3.2.1]octane
59 (1R,3R,5S)-8-(3-((S)-1-(2,4-Dichlorophenylsulfonyl)pyrrolidin-2-yl)propylsulfonyl)-3-(pyridin-4-yloxy)-8-azabicyclo[3.2.1]octane
60 (1R,3R,5S)-8-(3-((S)-1-(2,3-Dichlorophenylsulfonyl)pyrrolidin-2-yl)propylsulfonyl)-3-(pyridin-4-yloxy)-8-azabicyclo[3.2.1]octane
61 (1R,3R,5S)-8-(3-((S)-1-(4-Chloro-2,5-dimethylphenylsulfonyl)pyrrolidin-2-yl)propylsulfonyl)-3-(pyridin-4-yloxy)-8-azabicyclo[3.2.1]octane
62 3-(3-((S)-1-(2-Chloro-6-methylphenylsulfonyl)pyrrolidin-2-yl)propylsulfonyl)-9-(pyridin-4-yloxy)-3-azaspiro[5.5]undecane
63 9-(3,3-Difluoroazetidin-1-yl)-3-(3-((S)-1-(4-methoxy-2,6-dimethylphenylsulfonyl)pyrrolidin-2-yl)propylsulfonyl)-3-azaspiro[5.5]undecane
64 3-(3-((S)-1-(4-Methoxy-2,6-dimethylphenylsulfonyl)pyrrolidin-2-yl)propylsulfonyl)-9-(pyridin-4-yl)-3,9-diazaspiro[5.5]undecane
65 3-(3-((S)-1-(2-Chloro-6-methylphenylsulfonyl)pyrrolidin-2-yl)propylsulfonyl)-9-(pyridin-4-yl)-3,9-diazaspiro[5.5]undecane
66 3-(3-((S)-1-(4-Methoxy-2,6-dimethylphenylsulfonyl)pyrrolidin-2-yl)propylsulfonyl)-9-(pyridin-4-yloxy)-3-azaspiro[5.5]undecane hydrochloride
67 3-(3-((S)-1-(Naphthalen-1-ylsulfonyl)pyrrolidin-2-yl)propylsulfonyl)-9-(pyridin-4-yl)-3,9-diazaspiro[5.5]undecane hydrochloride
68 3-(Pyridin-4-yl)-9-(3-((S)-1-(2-(trifluoromethyl)phenylsulfonyl)pyrrolidin-2-yl)propylsulfonyl)-3,9-diazaspiro[5.5]undecane hydrochloride
69 (S)-4-(1-(3-(1-(2,2-Dimethylchroman-6-ylsulfonyl)pyrrolidin-2-yl)propylsulfonyl)piperidin-4-yloxy)pyridine
70 (S)-4-(1-(3-(1-(3-Chlorobenzylsulfonyl)pyrrolidin-2-yl)propylsulfonyl)piperidin-4-yloxy)pyridine
71 (S)-4-(1-(3-(1-(2-Chloro-4-(trifluoromethyl)phenylsulfonyl)pyrrolidin-2-yl)propylsulfonyl)piperidin-4-yloxy)pyridine
72 (S)-4-(1-(3-(1-(2,6-Dichloro-4-(Trifluoromethyl)phenyl-sulfonyl)pyrrolidin-2-yl)propylsulfonyl)piperidin-4-yloxy)pyridine
73 (S)-4-(1-(3-(1-(4-Fluoro-2,6-dimethylphenylsulfonyl)pyrrolidin-2-yl)propylsulfonyl)piperidin-4-yloxy)pyridine
74 3-(3-(1-(4-Methoxy-2,6-dimethylphenylsulfonyl)piperidin-2-yl)propylsulfonyl)-9-(pyridin-4-yl)-3,9-diazaspiro[5.5]undecane
75 3-(3-((S)-1-(4-Methylnaphthalen-1-ylsulfonyl)pyrrolidin-2-yl)propylsulfonyl)-9-(pyridin-4-yl)-3,9-diazaspiro[5.5]undecane
76 3-(3-((S)-1-(5-Chloronaphthalen-1-ylsulfonyl)pyrrolidin-2-yl)propylsulfonyl)-9-(pyridin-4-yl)-3,9-diazaspiro[5.5]undecane
77 3-(3-((S)-1-(4-Methoxynaphthalen-1-ylsulfonyl)pyrrolidin-2-yl)propylsulfonyl)-9-(pyridin-4-yl)-3,9-diazaspiro[5.5]undecane
78 3-(3-((S)-1-(4-Fluoronaphthalen-1-ylsulfonyl)pyrrolidin-2-yl)propylsulfonyl)-9-(pyridin-4-yl)-3,9-diazaspiro[5.5]undecane
79 3-(3-((S)-1-(4-Chloronaphthalen-1-ylsulfonyl)pyrrolidin-2-yl)propylsulfonyl)-9-(pyridin-4-yl)-3,9-diazaspiro[5.5]undecane
80 (1R,3s,5S)-8-(1-(3-((S)-1-(4-Methoxy-2,6-ydimethylphenylsulfonyl)pyrrolidin-2-l)propylsulfonyl)azetidin-3-yl)-3-(pyridin-4-yloxy)-8-azabicyclo[3.2.1]octane
81 (1R,3s,5S)-8-(1-(3-((S)-1-(2-Chloro-6-methylphenylsulfonyl)pyrrolidin-2-yl)propylsulfonyl)azetidin-3-yl)-3-(pyridin-4-yloxy)-8-azabicyclo[3.2.1]octane
82 2-(3-((S)-1-(4-Methoxy-2,6-dimethylphenylsulfonyl)pyrrolidin-2-yl)propylsulfonyl)-7-(pyridin-4-yl)-2,7-diazaspiro[4.4]nonane
83 2-(3-((S)-1-(2-Chloro-6-methylphenylsulfonyl)pyrrolidin-2-yl)propylsulfonyl)-7-(pyridin-4-yl)-2,7-diazaspiro[4.4]nonane
84 2-(3-((S)-1-(4-Methoxy-2,5-dimethylphenylsulfonyl)pyrrolidin-2-yl)propylsulfonyl)-7-(pyridin-4-yl)-2,7-diazaspiro[4.4]nonane
85 (S)-2-(3-(1-(4-Methoxy-2,6-dimethylphenylsulfonyl)pyrrolidin-2-yl)propylsulfonyl)-8-(pyridin-4-yl)-2,8-diazaspiro[4.5]decane
86 3-(3-(1-(2-Chloro-6-methylphenylsulfonyl)piperidin-2-yl)propylsulfonyl)-9-(pyridin-4-yl)-3,9-diazaspiro[5.5]undecane, and
87 3-(3-(1-(4-Methoxy-2,6-dimethylphenylsulfonyl)piperidin-2-yl)propylsulfonyl)-9-(pyridin-3-yl)-9-(2-(pyrrolidin-1-yl)ethoxy)-3-azaspiro[5.5]undecane optionally in the form of an individual enantiomer or an individual diastereomer, or a racemate, or the enantiomers, or the diastereomers, or mixtures of the enantiomers or diastereomers, in each case in the form of their bases and/or physiologically acceptable salts, in particular the hydrochloride salts.

The numbering of the individual embodiments of the compounds according to the invention used above is retained in the following explanations of the present invention, in particular in the description of the examples.

According to one aspect of the present invention, the compounds according to the invention preferably have an antagonistic action on the human B1R receptor or the B1R receptor of the rat. In a preferred embodiment of the invention, the compounds according to the invention have an antagonistic action both on the human B1R receptor (hB1R) and on the rat B1R receptor (rB1R).

In a preferred embodiment of the present invention, the compounds according to the invention show an inhibition of at least 15%, 25%, 50%. 70%, 80% or 90% on the human B1R receptor and/or on the B1R receptor of the rat in the FLIPR assay at a concentration of 10 µM. Compounds which show an inhibition on the human B1R receptor and on the B1R receptor of the rat of at least 70%, in particular of at least 80% and particularly preferably of at least 90% at a concentration of 10 µM are very particularly preferred.

The agonistic or antagonistic action of substances on the bradykinin 1 receptor (B1R) of the human and rat species can be quantified with ectopically expressing cell lines (CHO K1 cells) and with the aid of a $Ca^{2+}$-sensitive dyestuff (Fluo-4) in a fluorescent imaging plate reader (FLIPR). The value in % activation is based on the $Ca^{2+}$ signal after addition of Lys-Des-$Arg^9$-bradykinin (0.5 nM) or Des-$Arg^9$-bradykinin (100 nM). Antagonists lead to a suppression of the $Ca^{2+}$ inflow after addition of the agonist. % inhibition compared with the maximum achievable inhibition is stated.

The substances according to the invention preferably act, for example, on the B1R relevant in connection with various diseases, so that they are suitable as pharmaceutically active compounds in medicaments. The invention therefore also provides medicaments containing at least one compound according to the invention and optionally suitable additives and/or auxiliary substances and/or optionally further active compounds. The medicaments according to the invention optionally contain, in addition to at least one compound according to the invention, suitable additives and/or auxiliary substances, that is to say also carrier materials, fillers, solvents, diluents, dyestuffs and/or binders, and can be administered as liquid medicament forms in the form of injection solutions, drops or juices or as semi-solid medicament forms in the form of granules, tablets, pellets, patches, capsules, plasters/spray-on plasters or aerosols. The choice of auxiliary substances etc. and the amounts thereof to be employed depend on whether the medicament is to be administered orally, perorally, parenterally, intravenously, intraperitoneally, intradermally, intramuscularly, nasally, buccally, rectally or topically, for example on the skin, the mucous membranes or into the eyes. Formulations in the form of tablets, coated tablets, capsules, granules, drops, juices and syrups are suitable for oral administration, and solutions, suspensions, easily reconstitutable dry formulations and sprays are suitable for parenteral, topical and inhalatory administration. Substituted disulfonamides according to the invention in a depot, in dissolved form or in a plaster, optionally with the addition of agents which promote penetration through the skin, are suitable formulations for percutaneous administration. Formulation forms which can be used orally or percutaneously can release the substituted disulfonamides according to the invention in a delayed manner. The substituted disulfonamides according to the invention can also be used in parenteral long-term depot forms, such as e.g. implants or implanted pumps. In principle, other further active compounds known to persons skilled in the art can be added to the medicaments according to the invention.

The amount of active compound to be administered to patients varies as a function of the weight of the patient, of the mode of administration, the indication and the severity of the disease. 0.00005 to 50 mg/kg, in particular 0.01 to 5 mg/kg of at least one compound according to the invention are conventionally administered.

In a preferred form of the medicament, a substituted disulfonamide according to the invention contained therein may be present as an isolated diastereomer and/or enantiomer, as a racemate or as a non-equimolar or equimolar mixture of the diastereomers and/or enantiomers.

B1R is involved in particular in pain. The substituted disulfonamides according to the invention can accordingly be used for preparing a medicament for treatment of pain, in particular acute, visceral, neuropathic or chronic pain or inflammation pain. The invention therefore also provides a method of using at least one substituted disulfonamide according to the invention for the preparation of a medicament for treatment of pain, in particular acute, visceral, neuropathic or chronic pain. A particular embodiment of the present invention is the use of at least one of the substituted disulfonamides according to the invention for the preparation of a medicament for treatment of inflammation pain.

The invention also provides a method of treating or inhibiting pain, in particular acute, visceral, neuropathic or chronic pain or inflammation pain, by administering a pharmacologically effective amount of at least one substituted disulfonamide compound according to the invention to a subject in need thereof.

The invention also provides a method of using at least one substituted disulfonamide according to the invention for the preparation of a medicament for treatment of diabetes, diseases of the respiratory tract, for example bronchial asthma, allergies, COPD/chronic obstructive pulmonary disease or cystic fibrosis; inflammatory intestinal diseases, for example ulcerative colitis or CD/Crohn's disease; neurological diseases, for example multiple sclerosis or neurodegeneration; inflammations of the skin, for example atopic dermatitis, psoriasis or bacterial infections; rheumatic diseases, for example rheumatoid arthritis or osteoarthritis; septic shock; reperfusion syndrome, for example following cardiac infarction or stroke, obesity; and as an angiognesis inhibitor.

In addition, the invention contemplates a method of using at least one substituted disulfonamide according to the invention for treatment of one of the abovementioned indications.

In this context, in one of the above uses it may be advantageous for a substituted disulfonamide which is used to be present as an isolated diastereomer and/or enantiomer, as a racemate or as a non-equimolar or equimolar mixture of the diastereomers and/or enantiomers.

The invention also provides a method for treatment, in particular in one of the abovementioned indications, of a non-human mammal or a human requiring treatment of pain, in particular of acute, visceral, neuropathic or chronic pain or inflammation pain, by administration of a therapeutically active dose of a substituted disulfonamide according to the invention, or of a medicament according to the invention.

The invention also provides processes for the preparation of the substituted disulfonamides according to the invention as described in the description and the examples.

General Processes for Preparing Compounds According to the Invention:

The present invention also provides a process for the preparation of substituted disulfonamides according to the invention as described in the description and the examples.

Abbreviations
AIBN=N,N-azobisisobutyronitrile
DBU=1,8-diazabicyclo(5.4.0)undec-7-ene
DEAD=diethyl azodicarboxylate
DIAD=diisopropyl azodicarboxylate
DIBAL-H=diisobutylaluminium hydride
DIPEA=N,N—N,N-diisopropylethylamine
EPHP=N-ethylpiperidinium hypophosphite
eq=equivalents
h=hours
LAH=lithium aluminium hydride
LHMDS=lithium hexamethyldisilazide
MEK=methyl ethyl ketone
min=minutes
Ms=methanesulfonyl
NMP=N-methylpyrrolidone
Oxone®=2 $KHSO_5.KHSO_4.K_2SO_4$
PFP=pentafluorophenol
TMSCl=trimethylsilyl chloride The protective group (PG) is a suitable nitrogen-protecting group, preferably tert-butyloxycarbonyl (Boc), benzyloxycarbonyl (Cbz), 9-fluorenylmethoxycarbonyl (Fmoc), benzyl (Bn) or p-methoxybenzyl (PMB).

Protective groups can be introduced and removed by conventional methods known from the literature to persons skilled in the art, as described, for example, in Philip J. Kocienski, Protecting Groups, 3rd edition, Georg Thieme Verlag, 2005 (ISBN 3-13-135603-0) or Peter G. M. Wuts, Theodora W. Greene, Greene's Protective Groups in Organic Synthesis, 4th edition, Wiley-Interscience, 2007 (ISBN-13: 978-0-471-69754-1).

Diastereomers and/or enantiomers can likewise be separated by conventional methods known to persons skilled in the art, for example by recrystallization, chromatography or, in particular, HPLC chromatography or crystallization with an optionally chiral acid or base and separation of the salts or chiral HPLC chromatography (Fogassy et al., Optical resolution methods, Org. Biomol. Chem. 2006, 4, 3011-3030).

It will be apparent to persons skilled in the art that the sequence of some reaction steps can be modified, where appropriate.

The amino alcohols employed, compounds corresponding to formulas (A) and (F), are commercially available or are known from the literature. Amino alcohols of formulas (A) and (F) which are not commercially available can be prepared analogously to syntheses known from the literature, for example from the corresponding carboxylic acid esters or carboxylic acids using metal hydrides, for example lithium aluminium hydride, diisobutylaluminium hydride, diborane or borane complexes, as reducing agents. The amine units (RRNH) employed are commercially available, known from the literature or can be prepared by methods known to persons skilled in the art.

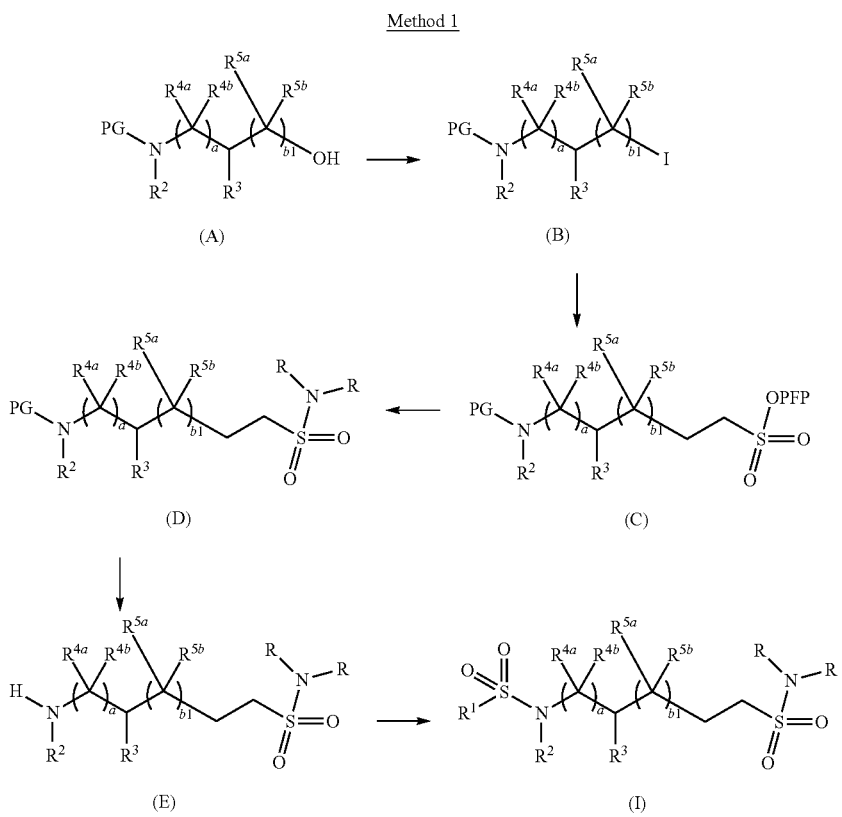

Method 1

In the abovementioned formulas (A)-(E) and (I), b1 represents 0, 1 or 2, and NRR represents the group —$(NR^8)_s$—$(CR^{9a}R^{9b})_t$-$AR^{10}R^{11}$.

In Method I, compounds of formula (A) are reacted in the presence of a suitable base, for example imidazole, pyridine or 4-(dimethylamino)-pyridine, optionally also in the presence of triphenylphoshine (or corresponding polymer-bonded or fluorinated variants) in an iodination, preferably with iodine, sodium iodide or potassium iodide, in at least one suitable solvent, for example diethyl ether, acetonitrile, toluene, benzene or pyridine, at a temperature of from preferably −20° C. to the reflux temperature to give compounds of formula (B). Alternatively, the reaction of compounds of formula (A) to give compounds of formula (B) can be carried out sequentially in two stages, the alcohol (A) first being converted into a suitable leaving group in a suitable solvent, such as, for example, methylene chloride, tetrahydrofuran, acetone, N,N-dimethylformamide or pyridine, optionally also in the presence of a suitable base, for example 4-(dimethylamino)-pyridine, pyridine, N,N—N,N-diisopropylethylamine (DIPEA) or triethylamine, optionally additionally in the presence of a tetraalkylammonium salt, for example tetra-n-butylammonium bromide, with a suitable reagent or reagent mixture, for example carbon tetrabromide/triphenylphosphine, methanesulfonyl chloride or p-toluenesulfonyl chloride, at a temperature of from preferably −20° C. to the reflux temperature. This product is then converted into compounds of the general formula (B) in a suitable solvent, preferably selected from the group consisting of acetone, methyl ethyl ketone or N,N-dimethyl-formamide, in the presence of a suitable iodine-containing salt, for example sodium iodide or potassium iodide, optionally additionally in the presence of a tetraalkylammonium salt, for example tetra-n-butylammonium iodide, at a temperature of from preferably −20° C. to 200° C., optionally in a microwave oven.

Compounds of the general formula (B) are then reacted in an intermolecular free radical addition with pentafluorophenyl vinylsulfonate in the presence of a chain carrier, preferably selected from the group consisting of tri-n-butyltin hydride, tristrimethylsilylsilane or N-ethylpiperidinium hypophosphite (EPHP), and in the presence of a suitable free radical initiator, for example triethylborane (plus air) or AIBN (plus heat), optionally additionally in the presence of a suitable reducing agent, for example sodium borohydride, in at least one suitable solvent, preferably selected from the group consisting of methylene chloride, toluene or 1,4-dioxane, preferably at temperatures of between 0° C. and the reflux temperature, to give compounds of the general formula (C).

The resulting compounds of formula (C) are reacted with amines (RRNH) in a suitable solvent, preferably selected from the group consisting of N,N-dimethylformamide, tetrahydrofuran, toluene, methylene chloride, NMP, methanol, water or mixtures thereof, in the presence of at least one suitable base, for example DBU, triethylamine, sodium hydride, LHMDS, optionally additionally in the presence of an ammonium salt, for example tetraalkylammonium halides, in particular tetra-n-butylammonium chloride, preferably at temperatures of from 0° C. to 200° C., optionally in a microwave oven, to give compounds of formula (D).

Compounds of the general formula (E) are obtained from compounds of formula (D) by eliminating the respective protective group (PG). Preferred protective groups can be removed as follows:

BOC protective groups can be removed in at least one solvent, preferably selected from the group consisting of acetonitrile, diethyl ether, tetrahydrofuran, methanol, ethanol, methylene chloride, 1,4-dioxane, ethyl acetate and dimethylformamide, with an acid, preferably selected from the group consisting of trifluoroacetic acid, hydrochloric acid, methanesulfonic acid and sulfuric acid, at temperatures of from preferably 0° C. to the reflux temperature.

minium chloride/anisole in a mixture of methylene chloride and nitromethane, or triethylsilane/PdCl$_2$ in methanol, with the addition of triethylamine, are also suitable. A further method is the hydrogenolytic removal of the protective group under increased pressure or normal pressure using catalysts, such as, for example, Pd on charcoal, Pd(OH)$_2$, PdCl$_2$, Raney nickel or PtO$_2$, in solvents, such as, for example, methanol, ethanol, 2-propanol, tetrahydrofuran, acetic acid, ethyl acetate or chloroform, optionally with the addition of HCl, formic acid or trifluoroacetic acid.

The compounds of formula (E) are reacted in a sulfonylation with sulfonyl chlorides, bromides or pentafluorophenolates R$^1$SO$_2$X (X=Cl, Br, OPFP), optionally in the presence of an organic or inorganic base, preferably selected from the group consisting of potassium carbonate, sodium carbonate, sodium bicarbonate, N,N-diisopropylethylamine (DIPEA), triethylamine, pyridine, 4-dimethylaminopyridine, diethylamine or DBU, preferably in an organic solvent, for example acetone, acetonitrile, methylene chloride or tetrahydrofuran and mixtures thereof, preferably at a temperature from 0° C. to the reflux temperature, to give sulfonylated compounds of formula (I) according to the invention.

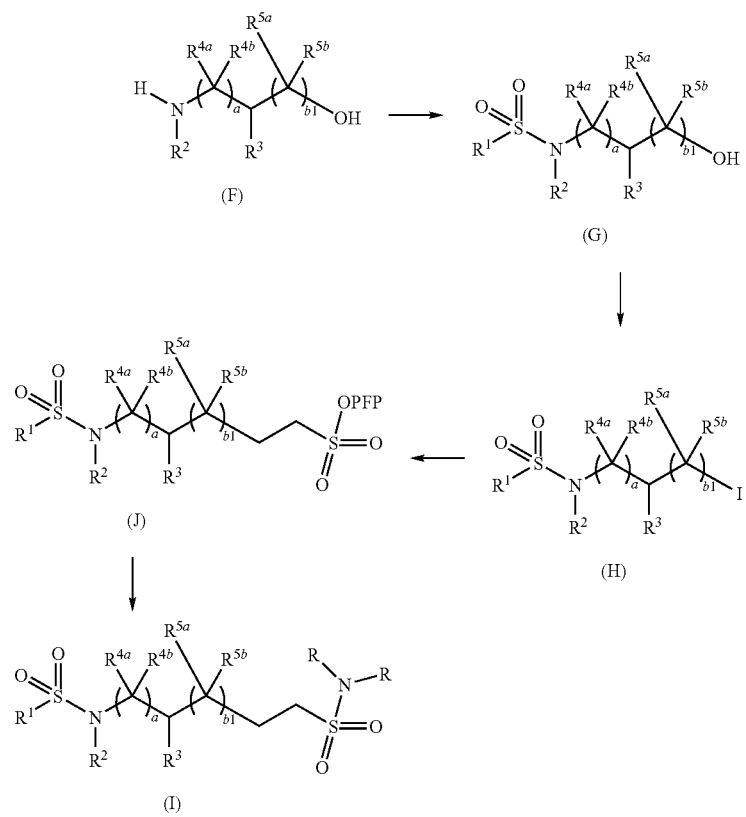

Method 2

Cbz protective groups can be removed under acidic conditions, for example by reaction with an HBr/glacial acetic acid mixture, a mixture of trifluoroacetic acid in 1,4-dioxane/water or HCl in methanol or ethanol. Reagents such as, for example, trimethylsilyl iodide, in solvents, such as, for example, methylene chloride, chloroform or acetonitrile, BF$_3$ etherate, with the addition of ethanethiol or Me$_2$S, in solvents, such as, for example, methylene chloride, a mixture of alu- In the abovementioned formulas (F), (G), (H), (J) and (I), b1 represents 0, 1 or 2, and NRR represents the group —(NR$^8$)$_s$—(CR$^{9a}$R$^{9b}$)$_t$-AR$^{10}$R$^{11}$.

In Method 2, compounds of formula (F) are reacted in a sulfonylation with sulfonyl chlorides, bromides or pentafluorophenolates R$^1$SO$_2$X (X=Cl, Br, OPFP), optionally in the presence of an organic or inorganic base, preferably selected from the group consisting of potassium carbonate, sodium carbonate, sodium bicarbonate, N,N-diisopropylethylamine (DIPEA), triethylamine, pyridine, 4-(dimethylamino)-pyridine, diethylamine or DBU, preferably in an organic solvent, for example acetone, acetonitrile, methylene chloride or tetrahydrofuran and mixtures thereof, at a temperature of from preferably 0° C. to the reflux temperature, to give the sulfonylated compounds of the general formula (G).

Compounds of formula (G) are then reacted in the presence of a suitable base, for example imidazole, pyridine or 4-(dimethylamino)-pyridine, optionally also in the presence of triphenylphoshine (or corresponding polymer-bonded or fluorinated variants) in an iodination with iodine, sodium iodide or potassium iodide, in at least one suitable solvent, for example diethyl ether, acetonitrile, toluene, benzene or pyridine, at a temperature of from preferably −20° C. to the reflux temperature to give compounds of formula (H). Alternatively, the reaction of compounds of formula (G) to give compounds of formula (H) can be carried out sequentially in two stages, the alcohol (G) first being converted to a suitable leaving group in a suitable solvent, such as, for example, methylene chloride, tetrahydrofuran, acetone, N,N-dimethylformamide or pyridine, optionally also in the presence of a suitable base, for example 4-(dimethylamino)-pyridine, pyridine, N,N—N,N-diisopropylethylamine (DIPEA) or triethylamine, optionally additionally in the presence of a tetraalkylammonium salt, for example tetra-n-butylammonium bromide, with a suitable reagent or reagent mixture, for example carbon tetrabromide/triphenylphosphine, methanesulfonyl chloride or p-toluenesulfonyl chloride, at a temperature of from preferably −20° C. to the reflux temperature. This product is then converted into a compound of formula (H) in a suitable solvent, preferably selected from the group consisting of acetone, methyl ethyl ketone or N,N-dimethylformamide, in the presence of a suitable iodine-containing salt, for example sodium iodide or potassium iodide, optionally additionally in the presence of a tetraalkylammonium salt, for example tetra-n-butylammonium iodide, at a temperature of from preferably −20° C. to 200° C., optionally in a microwave oven.

Compounds of formula (H) are then reacted in an intermolecular free radical addition with pentafluorophenyl vinylsulfonate in the presence of a chain carrier, preferably selected from the group consisting of tri-n-butyltin hydride, tristrimethylsilylsilane or N-ethylpiperidinium hypophosphite (EPHP), and in the presence of a suitable free radical initiator, for example triethylborane (plus air) or AIBN (plus heat), optionally additionally in the presence of a suitable reducing agent, for example sodium borohydride, in at least one suitable solvent, preferably selected from the group consisting of methylene chloride, toluene or 1,4-dioxane, preferably at temperatures of between 0° C. and the reflux temperature, to give compounds of formula (J).

The resulting compounds of formula (J) are reacted with amines (RRNH) in a suitable solvent, preferably selected from the group consisting of N,N-dimethylformamide, tetrahydrofuran, toluene, methylene chloride, NMP, methanol, water or mixtures thereof, in the presence of at least one suitable base, for example DBU, triethylamine, sodium hydride, LHMDS, optionally additionally in the presence of an ammonium salt, for example tetraalkylammonium halides, in particular tetra-n-butylammonium chloride, preferably at temperatures of from 0° C. to 200° C., optionally in a microwave oven, to give a compound of formula (I) according to the invention.

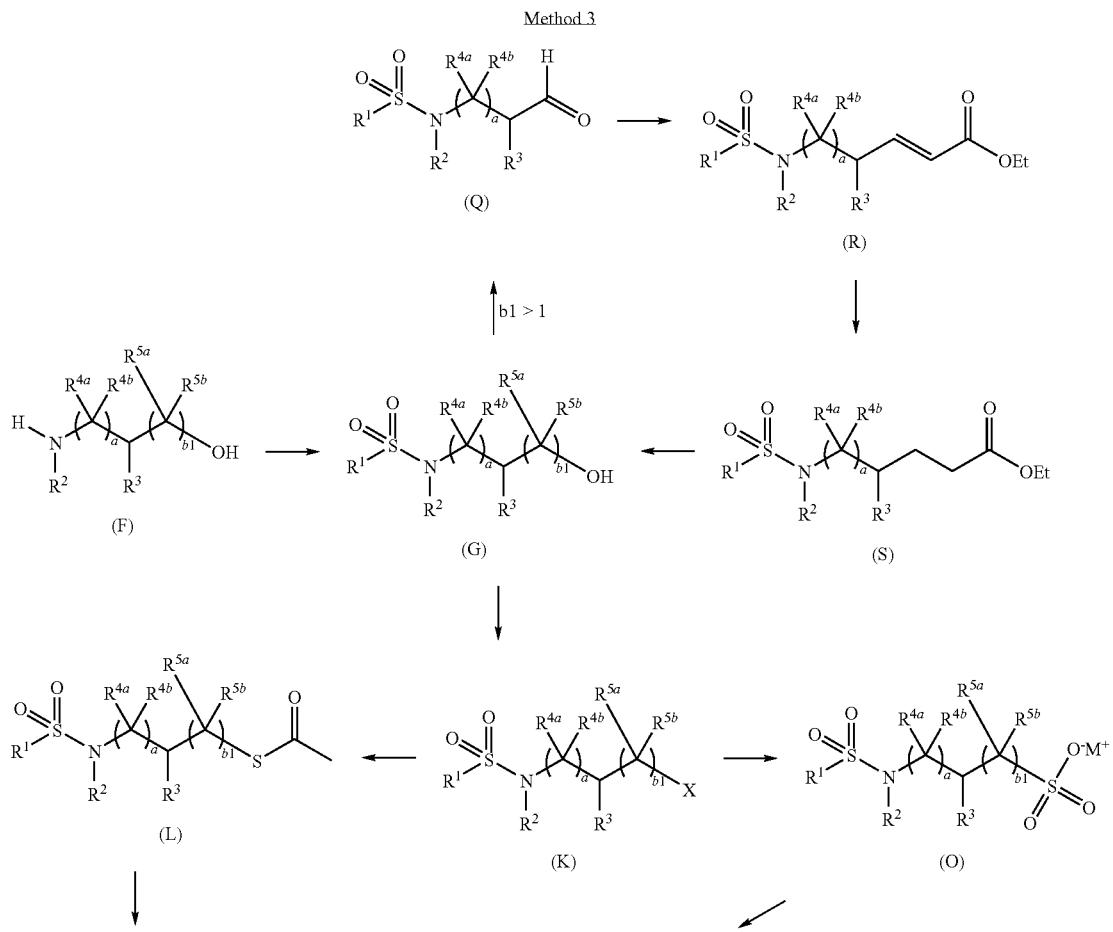

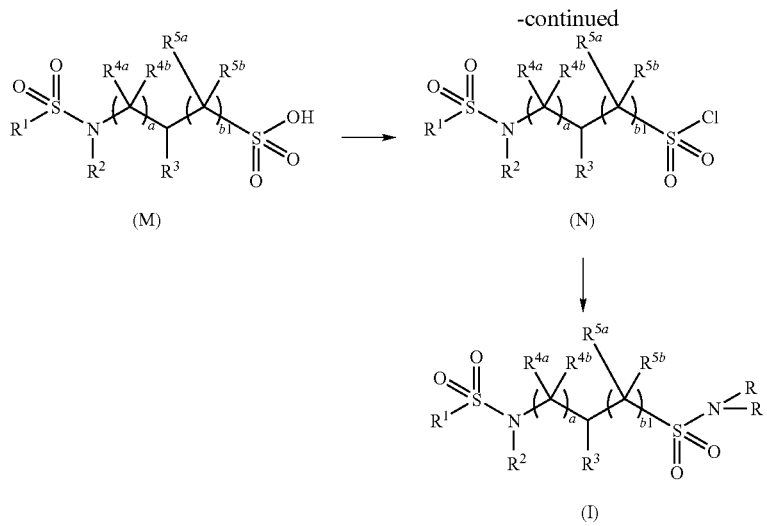

In the foregoing formulas (F), (G), (K), (L), (M), (N) and (I), b1 represents 0, 1, 2, 3 or 4, NRR represents the group —(NR$^8$)$_s$—(CR$^{9a}$R$^{9b}$)$_t$-AR$^{10}$R$^{11}$, and X represents halogen (preferably bromine, iodine) or OSO$_2$R (wherein R represents phenyl, tolyl, trifluoromethyl or methyl, preferably methyl).

In Method 3, compounds of formula (F) are reacted in a sulfonylation with sulfonyl chlorides, bromides or pentafluorophenolates R$^1$SO$_2$X (X=Cl, Br, OPFP), optionally in the presence of an organic or inorganic base, preferably selected from the group consisting of potassium carbonate, sodium carbonate, sodium bicarbonate, N,N-diisopropylethylamine (DIPEA), triethylamine, pyridine, 4-(dimethylamino)-pyridine, diethylamine or DBU, preferably in an organic solvent, for example acetone, acetonitrile, methylene chloride or tetrahydrofuran, preferably at a temperature from 0° C. to the reflux temperature, to give the sulfonylated compounds of formula (G).

If b1>1 and R$^{5a}$ and R$^{5b}$=H, then the compounds of formula (G) can optionally be converted into compounds of formula (Q). For this, the compounds of formula (G) are reacted by oxidation methods known to persons skilled in the art, such as, for example, Jones, Corey-Kim, Sarett or Swern oxidation. Typical reaction conditions for Jones oxidation are Cr$_2$O$_3$ in H$_2$SO$_4$ in solvents, such as, for example, diethyl ether, typical conditions for Corey-Kim oxidation are N-chlorosuccinimide and dimethylsulfide in, for example, toluene, whereas in Sarett oxidation Collins reagent (CrO$_3$*2 pyridine) is used. Swern oxidation is carried out in the presence of a mixture of oxalyl chloride and DMSO in the presence of a base, such as, for example, triethylamine or pyridine. TEMPO/p-(diacetoxyiodo)toluene in solvents, such as, for example, chloroform or cyclohexane, or Corey's reagent (pyridinium chlorochromate) in solvents, such as, for example, MC, and in the present of a base, such as, for example, sodium acetate or sodium bicarbonate, are similarly used. The oxidation can furthermore be carried out in the presence of MnO$_2$ in a suitable solvent, such as, for example, MC.

The resulting compounds of formula (Q) are converted into compounds of formula (R) in a Wittig-Horner reaction in the presence of ethyl 2-(dimethoxy-phosphoryl)acetate and bases, such as, for example, NaH, K$_2$CO$_3$, sodium ethanolate, potassium tert-butylate, lithium diisopropylamide or n-butyllithium, in solvents, such as, for example, water, THF, diethyl ether, hexane, benzene, toluene, 1,2-dimethoxyethane, DMF or DMSO, optionally in the presence of MgBr$_2$, triethylamine or HMPT.

Alternatively, the aldehydes of formula (Q) can be reacted in a Wittig-Horner reaction in the presence of methyl or ethyl 2-(diethylphosphino)acetate and bases, such as, for example, NaH, K$_2$CO$_3$, sodium ethanolate, potassium tert-butylate, lithium diisopropylamide or n-butyllithium, in solvents, such as, for example, water, THF, diethyl ether, hexane, benzene, toluene, DMF, DMSO or 1,2-dimethoxyethane, optionally in the presence of MgBr$_2$, triethylamine or HMPT, to give an aldehyde extended by a CH$_2$ spacer. This stage can optionally be repeated several times to extend b1 by one CH$_2$ each time. The resulting aldehyde can then be converted by reduction methods known to persons skilled in the art into the corresponding alcohol of formula (G).

Compounds of formula (R), which can be obtained from the compounds of formula (Q), are then reacted in a hydrogenolysis in the presence of a homogeneous or heterogeneous catalyst or by the action of a suitable reducing agent to give compounds of formula (S). A suitable homogeneous catalyst is, for example, tris(triphenylphosphane)rhodium chloride in solvents, such as, for example, benzene or toluene. Heterogeneous catalysts which can be used include Pt/C, palladium/C, Raney nickel or Pt$_2$O in solvents, such as, for example, acetic acid, methanol, ethanol, ethyl acetate, hexane, chloroform or mixtures thereof, optionally in the presence of acids, such as, for example, sulfuric acid or hydrochloric acid. A suitable reducing agent is, for example, L-Selectride, which is used in solvents, such as, for example, THF.

The carboxylic acid ester functionality of the compounds of the general formula (S) obtained in this way are then reduced to the corresponding compounds of the general formula (G) (b1=3). Reducing agents serve for this, such as, for example, LiBH$_4$ or NaBH$_4$, in solvents, such as, for example, diethyl ether, toluene, THF, water, methanol, ethanol or mixtures thereof, optionally in the presence of boronic acid esters. Zn(BH$_4$)$_2$ in solvents, such as, for example, DME, or BH$_3$—Me$_2$S complex in solvents, such as, for example, THF or MC, are similarly used. Aluminium hydrides, such as, for example, DIBAH or LAH, in solvents, such as, for example, diethyl ether, benzene, toluene, THF, MC, DME, hexane or mixtures thereof, can furthermore be used for reduction of the carboxylic acid ester.

Compounds of formula (G) are then reacted in at least one solvent, preferably selected from the group consisting of methylene chloride, 1,4-dioxane, diethyl ether, tetrahydrofuran, acetonitrile and N,N-dimethylformamide, with a sulfonyl chloride, preferably selected from the group consisting of methylsulfonyl chloride, trifluoromethylsulfonyl chloride, p-tolylsulfonyl chloride, and at least one base, preferably selected from the group consisting of sodium hydride, cesium carbonate, calcium carbonate, potassium carbonate, triethylamine, N,N-diisopropylethylamine (DIPEA) and pyridine, at temperatures of from preferably 0° C. to 80° C. to give compounds of formula (K) [X=OSO$_2$R].

These compounds of formula (K) [X=OSO$_2$R] can then optionally be converted into compounds of formula (K) [X=halogen] in a suitable solvent, preferably selected from the group consisting of acetone, methyl ethyl ketone or N,N-dimethylformamide, in the presence of at least one suitable halogen-containing salt, for example sodium iodide, potassium iodide, a tetraalkylammonium salt, for example tetra-n-butylammonium iodide, tetra-n-butylammonium bromide or tetra-n-butylammonium chloride, preferably at a temperature from −20° C. to 200° C., optionally in a microwave oven.

Alternatively, compounds of formula (G) are reacted, optionally in the presence of a suitable base, for example imidazole, pyridine, N,N—N,N-diisopropylethylamine (DIPEA), triethylamine or 4-(dimethylamino)-pyridine, optionally also in the presence of triphenylphoshine (or corresponding polymer-bonded or fluorinated variants) and/or in the presence of a tetraalkylammonium salt, for example tetra-n-butylammonium bromide, in a halogenation with iodine, sodium iodide, potassium iodide, carbon tetrabromide/triphenylphosphine, PCl$_3$, PBr$_3$ or alternative halogenating reagents known to persons skilled in the art, in at least one suitable solvent, for example methylene chloride, tetrahydrofuran, acetone, diethyl ether, acetonitrile, N,N-dimethylformamide, toluene, benzene or pyridine, preferably at a temperature from −20° C. to the reflux temperature to give compounds of formula (K) [X=halogen].

The resulting compounds of formula (K) are reacted in at least one suitable solvent, preferably selected from the group consisting of N,N-dimethylformamide, 1,4-dioxane, methylene chloride or tetrahydrofuran, in a Thio-Mitsunobu in the presence of DEAD or DIAD and triphenylphosphine (or corresponding polymer-bonded or fluorinated variants) or also in the presence of a suitable base, for example Cs$_2$CO$_3$ or DBU, optionally additionally in the presence of a tetraalkylammonium salt, for example tetra-n-butylammonium bromide, with thiolacetic acid or corresponding salts of this acid, such as, for example, potassium thioacetate, preferably at temperatures from −20° C. to 150° C., to give compounds of formula (L).

Compounds of formula (L) are then reacted in a suitable solvent or solvent mixtures, preferably selected from the group consisting of N,N-dimethylformamide, methylene chloride, tetrahydrofuran, methanol or water, in the presence of chlorine gas, or a suitable acid, for example formic acid, acetic acid or trifluoroacetic acid, optionally in combination with a suitable oxidizing agent, for example hydrogen peroxide or Oxone®, optionally additionally in the presence of potassium acetate, preferably at temperatures of from −20° C. to 150° C., to give compounds of formula (M).

Compounds of formula (M) are reacted in at least one suitable solvent, preferably selected from the group consisting of N,N-dimethylformamide, methylene chloride, tetrahydrofuran, toluene or benzene, in the presence of a chlorinating reagent, preferably selected from the group consisting of oxalyl chloride, phosphorus oxychloride, phosphorus pentachloride and thionyl chloride, preferably a temperature from −20° C. to 150° C., to give sulfonyl chlorides of formula (N).

Alternatively, sulfonyl chloride of formula (N) can be obtained in 2 stages from compounds of formula (K) via compounds of formula (O). For this, compounds of formula (K) are reacted in a suitable solvent or solvent mixture, preferably selected from the group consisting of water, methanol, ethanol, iso-propanol and tert-butanol, in the presence of Na$_2$SO$_4$, preferably at temperatures from −20° C. to 200° C., to give compounds of formula (O), which are then reacted in at least one suitable solvent, preferably selected from the group consisting of N,N-dimethylformamide, methylene chloride, tetrahydrofuran, toluene and benzene, in the presence of a chlorinating reagent, preferably selected from the group consisting of oxalyl chloride, phosphorus oxychloride, phorsphorus pentachloride and thionyl chloride, preferably at temperatures from −20° C. to 150° C., to give sulfonyl chlorides of formula (N).

Compounds of formula (N) are finally reacted in a sulfonylation with amines (RRNH), optionally in the presence of an organic or inorganic base, preferably selected from the group consisting of potassium carbonate, sodium carbonate, sodium bicarbonate, N,N-diisopropylethylamine (DIPEA), triethylamine, pyridine, 4-(dimethylamino)-pyridine, diethylamine and DBU, preferably in an organic solvent, for example acetone, acetonitrile, methylene chloride or tetrahydrofuran and mixtures thereof, at a temperature of from 0° C. to the reflux temperature to give compounds of formula (I) according to the invention.

Pharmacological Methods

1. Functional Investigation on the Bradykinin 1 Receptor (B1R)

The agonistic or antagonistic action of substances on the bradykinin 1 receptor (B1R) of the human and rat species can be determined with the following assay. In accordance with this assay, the Ca$^{2+}$ inflow through the channel is quantified with the aid of a Ca$^{2+}$-sensitive dyestuff (type Fluo-4, Molecular Probes Europe BV, Leiden, Holland) in a fluorescent imaging plate reader (FLIPR, Molecular Devices, Sunnyvale, USA).

2. Method:

Chinese hamster ovary cells (CHO K1 cells) transfected stably with the human B1R gene (hB1R cells) or the B1R gene of the rat (rB1R cells) are used. For functional studies, these cells are plated out on black 96-well plates with a clear base (BD Biosciences, Heidelberg, Germany or Greiner, Frickenhausen, Germany) in a density of 20,000-35,000 cells/well. The cells are left overnight at 37° C. and 5% CO$_2$ in culture medium (hB1R cells: Nutrient Mixture Ham's F12, Gibco Invitrogen GmbH, Karlsruhe, Germany or DMEM, Sigma-Aldrich, Taufkirchen, Germany; rB1R cells: D-MEM/F12, Gibco Invitrogen GmbH, Karlsruhe, Germany) with 10 vol. % FBS (foetal bovine serum, Gibco Invitrogen GmbH, Karlsruhe, Germany or PAN Biotech GmbH, Aidenbach, Germany). On the following day, the cells are loaded for 60 min at 37° C. with 2.13 µM Fluo-4 (Molecular Probes Europe BV, Leiden Holland) in HBSS buffer (Hank's buffered saline solution, Gibco Invitrogen GmbH, Karlsruhe, Germany) with 2.5 mM probenecid (Sigma-Aldrich, Taufkirchen, Germany) and 10 mM HEPES (Sigma-Aldrich, Taufkirchen, Germany). The plates are then washed 2× with HBSS buffer, and HBSS buffer which additionally contains 0.1% BSA (bovine serum albumin; Sigma-Aldrich, Taufkirchen, Germany), 5.6 mM glucose and 0.05% gelatine (Merck KGaA, Darmstadt, Germany) is added. After a further incubation of 20 minutes at room temperature, the plates are inserted into the FLIPR for the $Ca^{2+}$ measurement.

Alternatively, the plates are washed with buffer A (15 mM HEPES, 80 mM NaCl, 5 mM KCl, 1.2 mM $CaCl_2$, 0.7 mM $MgSO_4$, 2 g/l glucose, 2.5 mM probenecid), buffer A is added and the plates are loaded with 2.5 µM Fluo-4 and 0.025% Pluronic F127 (Sigma-Aldrich, Taufkirchen, Germany). Thereafter, the cells are washed 2× with buffer A and incubated for 30 minutes at room temperature with buffer A, which additionally contains 0.05% BSA and 0.05% gelatine, and thereafter inserted into the FLIPR for the $Ca^{2+}$ measurement. The $Ca^{2+}$-dependent fluorescence is measured here before and after addition of substances ($\lambda_{ex}$=488 nm, $\lambda_{em}$=540 nm). Quantification is by measurement of the highest fluorescence intensity (FC, fluorescence counts) over time.

3. FLIPR Assay:

The FLIPR protocol consists of 2 additions of substance. Test substances (10 µM) are first pipetted on to the cells and the $Ca^{2+}$ inflow is compared with the control (hB1R: Lys-Des-Arg$^9$-bradykinin>=50 nM; rB1R: Des-Arg$^9$-bradykinin 10 µM). This gives the result in % activation based on the $Ca^{2+}$ signal after addition of Lys-Des-Arg$^9$-bradykinin (>=50 nM) or Des-Arg$^9$-bradykinin (10 µM). After incubation for 10-20 minutes, Lys-Des-Arg$^9$-bradykinin (hB1R) or Des-Arg$^9$-bradykinin (rB1R) at the $EC_{80}$ concentration is applied and the inflow of $Ca^{2+}$ is likewise determined. Antagonists lead to a suppression of the $Ca^{2+}$ inflow. The percent inhibition compared to the maximum achievable inhibition is calculated.

In order to determine the $IC_{50}$ value, the substances are added in various concentrations. Duplicate or triplicate determinations (n=2 or n=3) are carried out, and these are repeated in at least one further independent experiment (N>=2).

The compounds preferably have a B1R-antagonistic action on the human receptor and/or on the rat receptor.

The invention is explained in further detail hereinafter with reference to illustrative examples which do not limit the general scope of the invention.

EXAMPLES

The chemicals and solvents employed were obtained commercially from the conventional suppliers (Acros, Aldrich, Fluka, Lancaster, Maybridge, TCI, Fluorochem, Tyger, ABCR, Fulcrum, FrontierScientific, Milestone etc.). The reactions were carried out in some cases under inert gas (nitrogen). The yields of the compounds prepared are not optimized. The mixing ratios of solvents are always stated in the volume/volume ratio. The equivalent amounts of reagents employed and the amounts of solvent and reaction temperatures and times can vary slightly between different reactions carried out by the same method. The working up and purification methods were adapted depending on the properties of the compounds. The compounds were analyzed by mass spectroscopy (HPLC-MS) and/or NMR:

NMR analysis was measured on a Bruker 440 MHz or 600 MHz. apparatus

Materials and methods for the HPLC-MS analysis: HPLC: Waters Alliance 2795 with PDA Waters 2998; MS: Micromass Quattro Micro™ API; column: Waters Atlantis® T3, 3 µm, 100 Å, 2.1×30 mm; column temperature: 40° C., eluent A: purified water+0.1% formic acid; eluent B: acetonitrile (gradient grade)+0.1% formic acid; gradient: 0% B to 100% B in 8.8 min, 100% B for 0.4 min, 100% B to 0% B in 0.01 min, 0% B for 0.8 min; flow rate: 1.0 ml/min; ionization: ES+, 25 V; mixture: 100 µl/min 70% methanol+0.2% formic acid; UV: 200-400 nm Preparation of the Educts Employed that were not Acquired Commercially 1. Amino alcohols Preparation of (2S,4S)-tert-butyl 4-Fluoro-2-(hydroxymethyl)pyrrolidine-1-carboxylate

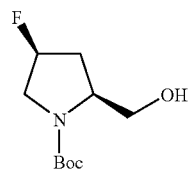

N-Boc-cis-4-fluoro-L-proline (2 g, 8.575 mmol) was dissolved in tetrahydrofuran (20 ml), the solution was cooled and boron hydride-tetrahydrofuran complex (1 mol/l, 12.86 ml) was added slowly at 0° C. The reaction mixture warmed slowly to room temperature, after stirring for 3 h it was cooled again to 0° C., water (5 ml) was slowly added dropwise, potassium carbonate (2 g, 14.477 mmol) was added and the mixture was stirred for 30 min. After separation of the phases, the aqueous phase was extracted with diethyl ether (3×20 ml) and the combined organic phases were dried over sodium sulfate and concentrated in vacuo. The crude product was purified by column chromatography (silica gel) with diethyl ether/hexane (4:1). Yield: 1.73 g, 92%

2. Amines

Preparation of 2-(piperazin-1-yl)thiazole

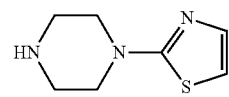

2-Bromothiazole (15 g, 91.45 mmol) and piperazine (27.6 g, 320 mmol) were dissolved in 1-butanol (290 ml) and the solution was refluxed for 5 h and stirred at room temperature for 15 h. The precipitate was filtered off, the mother liquor was concentrated and saturated sodium carbonate solution (100 ml) was added to the residue. The mixture was extracted with methylene chloride (2×80 ml) and the organic phases were combined, dried over magnesium sulfate and concentrated in vacuo. The crude product was purified by column chromatography (silica gel) with ethyl acetate/methanol (1:1). Yield: 14.2 g (91%)

Preparation of 4-(piperidin-4-yloxy)pyridine dihydrochloride

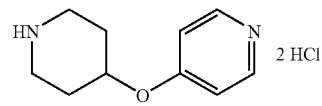

Stage (i): tert-Butyl 4-(pyridin-4-yloxy)piperidine-1-carboxylate tert-Butyl 4-hydroxypiperidine-1-carboxylate (6.348 g, 31.546 mmol) and triphenylphosphine (10.256 g, 39.432 mmol) were added to a solution of 4-hydroxypyridine (3 g, 31.456 mmol) in tetrahydrofuran (50 ml) at room temperature. Diisopropyl azodicarboxylate (7.66 ml, 39.432 mmol) was subsequently added dropwise and the mixture was then stirred at 55° C. for 15 h. Saturated sodium bicarbonate solution (50 ml) was added to the reaction mixture and the mixture was extracted with ethyl acetate (4×80 ml). The combined organic phases were washed with sat. sodium chloride solution (20 ml), dried over sodium sulfate and concentrated in vacuo. The crude product was subsequently purified by column chromatography (silica gel) with ethyl acetate/hexane (4:1). Yield: 4.11 g (46%)

Stage (ii): 4-(Piperidin-4-yloxy)pyridine dihydrochloride

Hydrogen chloride (47 ml, 59 mmol, 1.25 mol/l in methanol) was added to a solution of tert-butyl 4-(pyridin-3-yloxy)piperidine-1-carboxylate (4.1 g, 14.727 mmol) in methanol (10 ml) at room temperature and the reaction mixture was refluxed for 30 min. The solvent was removed in vacuo and the residue was taken up in a little ethanol, and diethyl ether was added. The mixture was subsequently cooled in an ice bath for 30 min and the solid formed was filtered off and dried. Yield: 3.46 g (93%)

Preparation of 4-(pyridin-3-yl)piperidin-4-ol

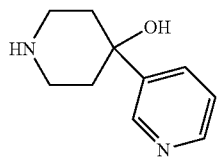

Stage (i): 1-Benzyl-4-(pyridin-3-yl)piperidin-4-ol (Apparatus: 1 l three-necked flask with nitrogen balloon) Magnesium (5.7 g) was initially introduced into anhydrous ether (125 ml), 1,1-dibromoethane (0.5 g) and isopropyl chloride (17.3 ml) were added dropwise and the mixture was stirred for 15 min to initiate the magnesium. A solution of 3-bromopyridine (25 g) in anhydrous tetrahydrofuran (400 ml) was added dropwise at 40° C. over the course of 20 min and the mixture was then refluxed for 2 h. A solution of 1-benzylpiperidin-4-one (30 g) in anhydrous tetrahydrofuran (100 ml) was finally added dropwise at 40° C. over the course of 20 min and the mixture was stirred at room temperature overnight. Thin layer chromatography control: 10% methanol in chloroform. The reaction mixture was hydrolysed with water (50 ml) at 0° C. and filtered over Celite. Extraction was carried out with methylene chloride (2×100 ml) and the combined organic phases were washed with water (50 ml), dried over sodium sulfate and concentrated in vacuo. The crude product was purified by column chromatography (Alox neutral) with 5% methanol in chloroform. Yield: 8.2 g (19%)

Stage (ii): 4-(Pyridin-3-yl)piperidin-4-ol (Apparatus: 1 l three-necked flask with condenser) Palladium on charcoal (10%, catalytic amount) was added to a solution of 1-benzyl-4-(pyridin-3-yl)piperidin-4-ol (32 g) in methanol (220 ml), followed by ammonium formate solution (22.7 g in 50 ml of water). The reaction mixture was refluxed at 68° C. overnight. Thin layer chromatography control: 20% methanol in chloroform. The mixture was filtered over Celite and the filtrate was concentrated in vacuo. The residue was washed with acetone (100 ml) in order to obtain the desired compound in a pure form. Yield: 17.3 g (81%)

Preparation of 3-(pyridin-4-yl)-3,9-diazaspiro[5.5]undecane dihydrochloride

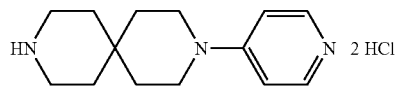

Stage (i): tert-Butyl 9-(pyridin-4-yl)-3,9-diazaspiro[5.5]undecane-3-carboxylate tert-Butyl 3,9-diazaspiro[5.5]undecane-3-carboxylate (1 g, 3.931 mmol), 4-chloropyridinium chloride (1.765 g, 11.794 mmol) and triethylamine (2.2 ml, 15.725 mmol) were refluxed in 1-butanol (50 ml) for 15 h. Saturated sodium bicarbonate solution (30 ml) and ethyl acetate (80 ml) were added, the phases were separated and the aqueous phase was extracted with ethyl acetate (2×80 ml). The combined organic phases were dried over magnesium sulfate and concentrated in vacuo. The crude product was purified by column chromatography (silica gel) with ethyl acetate/hexane/methanol/ammonia (25% aq) 400/40/40/1. Yield: 0.52 g (39%)

Alternatively, this reaction can also be carried out with 4-fluoropyridine (or the corresponding hydrochloride). The target compound also can alternatively be prepared via Hartwig-Buchwald coupling with 4-bromopyridine in the presence of a suitable palladium catalyst, such as e.g. tris(dibenzylidene-acetone)dipalladium/(S)-(–)-2,2'-bis(diphenylphosphino)-1,1'-binaphthyl, in toluene and in the presence of a suitable base, for example sodium tert-butylate, at 90° C.

Stage (ii): 3-(Pyridin-4-yl)-3,9-diazaspiro[5.5]undecane dihydrochloride

Hydrogen chloride in methanol (1.25 mol/l, 6.3 ml) was added to tert-butyl 9-(pyridin-4-yl)-3,9-diazaspiro[5.5]undecane-3-carboxylate (0.52 g, 1.569 mmol) and the mixture was refluxed for 1 h. The solvent was removed in vacuo, the residue taken up in ethanol (3 ml) and the mixture cooled. Acetone (80 ml) was added and the mixture was stirred in an ice bath for 30 min. The precipitate was filtered out with suction, washed with diethyl ether and dried in vacuo.

Yield: 0.4 g (83%)

Alternatively, the protective group can also be removed with an excess of trifluoroacetic acid in methylene chloride at temperatures of between 0° C. and room temperature.

Preparation of (1R,3s,5S)-3-(pyridin-4-yloxy)-8-azabicyclo[3.2.1]octane dihydrochloride

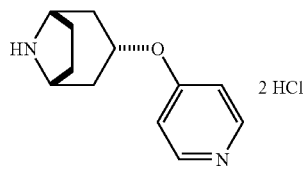

Stage (i): (1R,3R,5S)-tert-Butyl 3-hydroxy-8-azabicyclo[3.2.1]octane-8-carboxylate and (1R,3s,5S)-tert-butyl 3-hydroxy-8-azabicyclo[3.2.1]octane-8-carboxylate Boc-nortropinone (2.5 g, 11.097 mmol) was dissolved in methanol (20 ml) and the solution was cooled with an ice bath. Sodium borohydride (1.26 g, 33.291 mmol) was added slowly under an inert gas. After stirring at room temperature for 4 h, hydrolysis was carried out with saturated sodium bicarbonate solution (30 ml), methanol was removed in vacuo and the aqueous phase was extracted with ethyl acetate (3×50 ml). The combined organic phases were dried over magnesium sulfate and concentrated in vacuo. The crude product was purified by column chromatography (silica gel) with ethyl acetate/methanol/methylene chloride/ammonia (25 aq) (400:40:40:1). The isomers were separated by this procedure; this was assigned by NMR analysis. Yield: endo 50% [reacted further in stage (ii)], exo 25%

Stage (ii): (1R,3s,5S)-tert-Butyl 3-(pyridin-4-yloxy)-8-azabicyclo[3.2.1]octane-8-carboxylate (1R,3r,5S)-tert-Butyl 3-hydroxy-8-azabicyclo[3.2.1]octane-8-carboxylate (1 eq) was dissolved in tetrahydrofuran (50 eq), and 4-hydroxypyridine (1 eq) and triphenylphosphine (1.25 eq) were added. Thereafter, diisopropyl azodicarboxylate (1.25 eq) was added dropwise and the reaction mixture was heated to 55° C. After 15 h tetrahydrofuran was removed in vacuo, the residue was taken up in ethyl acetate (50 ml) and the mixture was extracted with aqueous hydrogen chloride solution (2×40 ml, 1 mol/l). The aqueous phase was rendered alkaline (pH=8) with sodium hydroxide solution and extracted with ethyl acetate (3×50 ml). The organic phases were combined, dried over sodium sulfate and concentrated in vacuo. The crude product was purified by column chromatography (silica gel) with ethyl acetate/hexane (3:1). Yield: 65% The other isomer can be obtained analogously from the corresponding exo product from stage (i).

Stage (iii): (1R,3s,5S)-3-(Pyridin-4-yloxy)-8-azabicyclo[3.2.1]octane dihydrochloride (1R,3s,5S)-tert-Butyl 3-(pyridin-4-yloxy)-8-azabicyclo[3.2.1]octane-8-carboxylate (1 eq) was added to hydrogen chloride in methanol (4 eq, 1.25 mol/l) and the reaction mixture was refluxed for 30 min. The solvent was removed in vacuo and the residue was taken up in a little ethanol (5 ml), and acetone (30 ml) was then added. The mixture was stirred at room temperature for 30 min and diethyl ether (20 ml) was then added. The precipitate was filtered off with suction, washed with diethyl ether and dried in vacuo. Yield: 90%

The other isomer can be obtained analogously from the corresponding exo product from stage (i) analogously to stage (ii) and (iii).

Preparation of
9-(pyridin-4-yloxy)-3-azaspiro[5.5]undecane
dihydrochloride

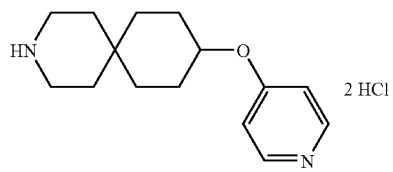

Stage (i):
1-(Benzyloxycarbonyl)piperidine-4-carboxylic acid

Water (75 ml) was added to piperidine-4-carboxylic acid (25 g) in THF (75 ml), followed by sodium bicarbonate (30.8 g). The mixture was cooled to 0° C. and Cbz chloride (38.9 ml) was added dropwise. The reaction mixture was subsequently stirred at room temperature for 5 h (TLC control). When the reaction was complete, the organic solvent was distilled off and the residue was taken up in water (200 ml), and the mixture was washed with ethyl acetate (2×150 ml). The aqueous phase was rendered acidic with dilute aqueous HCl and extracted with ethyl acetate. The organic phase was dried ($Na_2SO_4$) and concentrated in vacuo. Yield: 48.5 g (96%)

Stage (ii): 1-Benzyl 4-methyl
piperidine-1,4-dicarboxylate 1-(Benzyloxycarbonyl)piperidine-4-carboxylic acid (48.5 g) in methanol (485 ml) was cooled to 0° C. and thionyl chloride (13.34 ml) was added dropwise. The mixture was subsequently refluxed for 20 min (TLC control). When the reaction was complete, the methanol was distilled off, the residue was taken up in water (15 ml) and with ethyl acetate (2×150 ml). The combined organic phases were extracted with water and sat. sodium chloride solution and the extract was dried ($Na_2SO_4$) and concentrated in vacuo. Yield: 38 g (67%)

Stage (iii): Benzyl 4-formylpiperidine-1-carboxylate

A solution of 1-benzyl 4-methyl piperidine-1,4-dicarboxylate (10 g) in toluene (100 ml) under nitrogen was cooled to −78° C. DIBAL-H (60.9 ml) subsequently was added dropwise at −78° C., and the mixture was stirred at this temperature for 1 h (TLC control). Because the reaction was incomplete, a further 0.2 eq of DIBAL-H was added and the mixture was stirred for a further 30 min (TLC control: some educt and the corresponding alcohol were to be detected). Methanol (40 ml), followed by sat. sodium chloride solution (40 ml) were added slowly to the reaction mixture at −78° C. The mixture was filtered over Celite and the solvent was removed in vacuo. The residue was extracted with ethyl acetate (3×75 ml) and the extract was dried ($Na_2SO_4$) and concentrated in vacuo. The crude product obtained in this way was purified by column chromatography (silica gel, 20% ethyl acetate/hexane). Yield: 4.3 g (49%)

Stage (iv): Benzyl
9-oxo-3-azaspiro[5.5]undec-7-ene-3-carboxylate

Methyl vinyl ketone (1.64 ml), ethanol (5 ml) and water (5 ml) were added to benzyl 4-formylpiperidine-1-carboxylate (5 g). The mixture was subsequently added to a boiling solution of potassium hydroxide (0.22 g) in ethanol (10 ml) and the resulting reaction mixture was refluxed for 1 h (TLC control). When the reaction was complete, the mixture was added to water (25 ml) and extracted with ethyl acetate (2×50 ml). The combined organic phases were dried ($Na_2SO_4$) and concentrated in vacuo. The crude product obtained in this way was purified by column chromatography (silica gel, 25% ethyl acetate/hexane). Yield: 2.8 g (46%)

Stage (v): tert-Butyl
9-oxo-3-azaspiro[5.5]undecane-3-carboxylate

Boc anhydride (9.4 ml) and potassium carbonate (7.56 g) were added to benzyl 9-oxo-3-azaspiro[5.5]undec-7-ene-3-carboxylate (8.2 g) in EtOH/water (9:1) (200 ml). Pd/C (1 g) was subsequently added and hydrogenolysis was carried out under 80 psi for 4 h (TLC control). When the reaction was complete, the mixture was filtered over Celite and the residue rinsed with ethanol and ethyl acetate. The filtrate was dried ($Na_2SO_4$) and concentrated in vacuo. The residue was taken up in ethyl acetate and water and the aqueous phase was extracted with ethyl acetate. The combined organic phases were dried ($Na_2SO_4$) and concentrated in vacuo. The resulting crude product was purified by column chromatography (silica gel, 20% ethyl acetate/hexane). Yield: 2.92 g, 40%

Stage (vi): tert-Butyl 9-hydroxy-3-azaspiro[5.5]undecane-3-carboxylate tert-Butyl 9-oxo-3-azaspiro[5.5]undecane-3-carboxylate (1.5 g) was dissolved in THF (7.5 ml) and the solution was cooled to −5° C. NaBH$_4$ (0.212 g) was subsequently added and the mixture was stirred at room temperature for 1 h (TLC control). When the reaction was complete, acetic acid was added to the mixture and the methanol was subsequently distilled off. The residue was taken up in water (50 ml) and the mixture was extracted with ethyl acetate (2×50 ml). The combined organic phases were dried (Na$_2$SO$_4$) and concentrated in vacuo. The crude product obtained in this way was purified by column chromatography (silica gel, 30% ethyl acetate/hexane). Yield: 1.2 g (80%)

Stage (vii): tert-Butyl 9-(pyridin-4-yloxy)-3-azaspiro[5.5]undecane-3-carboxylate 4-Chloropyridine hydrochloride (1.3 g) was added to sodium hydride (0.89 g) in DMSO (20 ml) and the mixture was stirred for 10 min. tert-Butyl 9-oxo-3-azaspiro[5.5]undecane-3-carboxylate (2.0 g) in DMSO (20 ml) was subsequently added slowly and the mixture was stirred overnight (TLC control: conversion approx. 30-35%). A catalytic amount of sodium iodide was added and the reaction mixture was stirred at 80° C. for 8 h (TLC control). Methanol and NaHCO$_3$ solution was added to the reaction mixture and the mixture was stirred for 20 min. It was then extracted with ethyl acetate and the extract was washed again with NaHCO$_3$ solution and cold water. The organic phase was dried (Na$_2$SO$_4$) and concentrated in vacuo. The crude product obtained in this way was purified by column chromatography (silica gel, 70% ethyl acetate/hexane). Yield: 1.0 g (40%)

Stage (viii): 9-(Pyridin-4-yloxy)-3-azaspiro[5.5]undecane dihydrochloride tert-Butyl 9-(pyridin-4-yloxy)-3-azaspiro[5.5]undecane-3-carboxylate (1 g, 2.886 mmol) was dissolved in methanol (2 ml), hydrogen chloride in methanol (1.25 mol/l, 11.5 ml) was added and the mixture was refluxed for 30 min. The solvent was removed in vacuo and the residue was dissolved in a small amount of ethanol. Acetone (approx. 25 ml) was subsequently added, the mixture was stirred at 0° C. for 30 min and the solid formed was finally filtered off with suction. Yield: 0.96 g (>99%)

Preparation of 9-(3,3-difluoroazetidin-1-yl)-3-azaspiro[5.5]undecane dihydrochloride

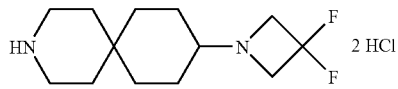

Stage (i): tert-Butyl 9-(3,3-difluoroazetidin-1-yl)-3-azaspiro[5.5]undecane-3-carboxylate tert-Butyl 9-oxo-3-azaspiro[5.5]undecane-3-carboxylate (for the synthesis, see above) (1 g, 3.74 mmol) was added to 3,3-difluoroazetidine hydrochloride (0.484 g, 3.74 mmol) and triethylamine (0.52 ml, 3.74 mmol) in 1,2-dichloroethane (15 ml). The mixture was stirred for 5 min and sodium triacetoxyborohydride (1.1 g, 5.23 mmol) was subsequently added and the mixture was stirred at room temperature for 3 d. Saturated sodium bicarbonate solution was added and after separation of the phases the aqueous phase was extracted with methylene chloride (2×). The combined organic phases were washed with saturated sodium chloride solution (1×), dried over magnesium sulfate and concentrated in vacuo. Yield: 1.26 g (98%)

Stage (ii): 9-(3,3-Difluoroazetidin-1-yl)-3-azaspiro[5.5]undecane dihydrochloride tert-Butyl 9-(3,3-difluoroazetidin-1-yl)-3-azaspiro[5.5]undecane-3-carboxylate (1.26 g, 3.66 mmol) was dissolved in hydrogen chloride in methanol (1.25 mol/l, 29 ml) and the solution was refluxed for 45 min. The solvent was removed in vacuo and the residue was dissolved in a small amount of ethanol. A solid was subsequently precipitated out by addition of acetone. The mixture was stirred at room temperature for 10 min, diethyl ether was then added and the mixture was stirred at room temperature for a further 30 min. The resulting precipitate was filtered out with suction, washed with diethyl ether and dried in vacuo. Yield: 1.1 g (95%)

Preparation of 2-(pyridin-4-yl)-2,7-diazaspiro[4.4]nonane dihydrochloride

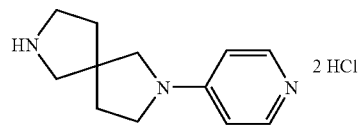

Stage (i): tert-Butyl 7-(pyridin-4-yl)-2,7-diazaspiro[4.4]nonane-2-carboxylate tert-Butyl 2,7-diaza-spiro[4.4]nonane-2-carboxylic acid (4.419 mmol, 1 eq) and N-ethyl-diisopropylamine (17.674 mmol, 4 eq) were dissolved in 2-propanol (8 ml), 4-chloropyridine (13.256 mmol, 3 eq) was added and the mixture was heated at 90° C. for 16 h. Saturated sodium bicarbonate solution (20 ml) was added and the phases were separated. The aqueous phase was extracted with ethyl acetate (4×20 ml) and the combined org. phases were washed with saturated sodium chloride solution, dried over magnesium sulfate and concentrated. After purification by column chromatography (silica gel, ethyl acetate/methylene chloride/methanol/ammonia (25 aq) (100:100:25:1), the desired product was obtained as a pale brown oil. Yield: 0.67 g (50%)

Stage (ii): 2-(Pyridin-4-yl)-2,7-diazaspiro[4.4]nonane dihydrochloride tert-Butyl 7-(pyridin-4-yl)-2,7-diazaspiro[4.4]nonane-2-carboxylate (2.208 mmol, 1 eq) was heated at the boiling temperature with hydrogen chloride in methanol (1.25 M, 6 eq) for 30 min. The methanol was concentrated in vacuo, the residue was dissolved in analytical grade ethanol (5 ml), and analytical grade acetone (25 ml) was added. The mixture was stirred at 0° C. for 30 min and a pale precipitate precipitated out. This was filtered out, washed with diethyl ether and dried under a high vacuum to obtain the desired product. Yield: 0.55 g (90%)

Preparation of 8-(pyridin-4-yl)-2,8-diazaspiro[4.5]decane dihydrochloride

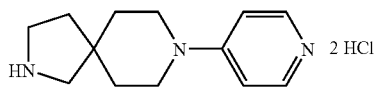

Stage (i): tert-Butyl 8-(pyridin-4-yl)-2,8-diazaspiro[4.5]decane-2-carboxylate tert-Butyl 2,8-diazaspiro[4.5]decane-2-carboxylate (10.403 mmol, 1 eq) and N-ethyl-diisopropylamine (41.608 mmol, 4 eq) were dissolved in 2-propanol (20 ml). 4-Chloropyridine (31.206 mmol, 3 eq) was added and the mixture was heated at 90° C. for 16 h. Saturated sodium bicarbonate solution (50 ml) was added and the phases were separated. The aqueous phase was extracted with ethyl acetate (4×50 ml) and the combined org. phases were washed with saturated sodium chloride solution (50 ml), dried over magnesium sulfate and concentrated. After purification by column chromatography (silica gel, ethyl acetate/methylene chloride/methanol/ammonia (25% aq) (100:100:25:1), the desired product was obtained as a yellow oil. Yield: 1.8 g (55%)

Stage (ii): 8-(Pyridin-4-yl)-2,8-diazaspiro[4.5]decane dihydrochloride tert-Butyl 8-(pyridin-4-yl)-2,8-diazaspiro[4.5]decane-2-carboxylate (5.671 mmol, 1 eq) was dissolved in analytical grade ethanol (20 ml) and acetyl chloride (28.355 mmol, 3 eq.) was then added at 0° C. The mixture was stirred at 25° C. for 16 h. Thereafter, the solvent was concentrated in vacuo and the residue was dried under a high vacuum to obtain the desired product. Yield: 1.48 g (90%)

Preparation of (1R,3s,5S)-8-(azetidin-3-yl)-3-pyridin-4-yloxy-8-azabicyclo[3.2.1]octane trihydrochloride

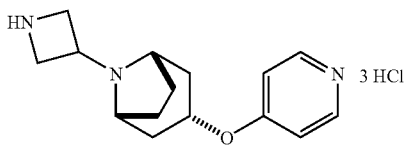

Stage (i): 3-[(1R,3s,5S)-3-Pyridin-4-yloxy-8-azabicyclo[3.2.1]octan-8-yl]-azetidine-1-carboxylic acid tert-butyl ester (1R,3s,5S)-3-(Pyridin-4-yloxy)-8-azabicyclo[3.2.1]octane dihydrochloride (for the synthesis see above) (2.535 mmol, 1 eq.) was dissolved in 1,2-dichloroethane (10 ml) and triethylamine (5.07 mmol, 2-eq.), and 1-Boc-3-azetidinone (2.535 mmol, 1 eq) was added. The mixture was stirred at room temperature for 5 min. Sodium triacetoxyborohydride (3.549 mmol, 1.4 eq) was then added in portions and the resulting reaction mixture was stirred at room temperature for 16 h. Saturated sodium bicarbonate solution (20 ml) and methylene chloride (50 ml) were added and the phases were separated. The aqueous phase was washed with methylene chloride (1×20 ml). The combined organic phases were washed with saturated sodium chloride solution (1×50 ml), dried over magnesium sulfate and concentrated under reduced pressure. The crude product was purified by column chromatography (silica gel, ethyl acetate/hexane/methanol 12:2:1) to obtain the desired product. Yield: 47%

Stage (ii): (1R,3s,5S)-8-(Azetidin-3-yl)-3-pyridin-4-yloxy-8-azabicyclo[3.2.1]octane trihydrochloride 3-[(1R,3s,5S)-3-Pyridin-4-yloxy-8-azabicyclo[3.2.1]octan-8-yl]-azetidine-1-carboxylic acid tert-butyl ester (1.168 mmol, 1 eq) was dissolved in hydrogen chloride in methanol (1.25 M, 10 eq) and the solution was heated at the boiling temperature for 30 min. After thin layer chromatography control, the methanol was concentrated under reduced pressure. The residue was taken up in ethanol/acetone (20 ml, 1:5) and a solid was precipitated out with diethyl ether (20 ml). This was filtered off with suction, washed with diethyl ether and dried under a high vacuum to give the desired product. Yield: 95%

Preparation of 9-(pyridin-3-yl)-9-(2-(pyrrolidin-1-yl)ethoxy)-3-azaspiro[5.5]undecane

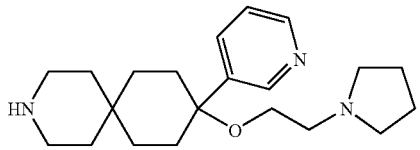

Step-1: tert-Butyl 9-hydroxy-9-(pyridin-3-yl)-3-azaspiro[5.5]undecane-3-carboxylate 3-Bromopyridine (22.47 mmol, 2 eq) was dissolved in diethyl ether (10 ml) and the solution was added dropwise to a solution of n-BuLi (24.7 mmol, 2.2 eq) in diethyl ether (70 ml) at −78° C. The resulting mixture was stirred for 30 min. tert-Butyl 9-oxo-3-azaspiro[5.5]undecane-3-carboxylate (for the synthesis see above) (11.23 mmol, 1 eq.) was dissolved in diethyl ether (10 ml), the solution was slowly added, and the reaction mixture was then stirred at −78° C. for 1 h. The reaction mixture was warmed to room temperature, ethyl acetate (150 ml) and water (80 ml) were added and the phases were separated. The aqueous phase was extracted with ethyl acetate (2×70 ml) and the combined organic phases were dried over magnesium sulfate and concentrated. The crude product was purified by column chromatography (2% methanol in methylene chloride). Yield: 19%

Step-2: tert-Butyl 9-(pyridin-3-yl)-9-(2-(pyrrolidin-1-yl)ethoxy)-3-azaspiro[5.5]undecane-3-carboxylate A mixture of tert-butyl 9-hydroxy-9-(pyridin-3-yl)-3-azaspiro[5.5]undecane-3-carboxylate (2.25 mmol, 1 eq), 1-(2-bromo-ethyl)-pyrrolidine hydrochloride (3.375 mmol, 1.5 eq), dry KOH powder (11.25 mmol, 5 eq) and catalytic amounts of 18-crown-6 in toluene (25 ml) was heated at the boiling temperature for 12 h. The toluene was concentrated under reduced pressure and the residue was taken up in water and the mixture was extracted with methylene chloride (3×60 ml). The combined organic phases were washed with dist. water (10 ml) and saturated sodium chloride solution (10 ml), dried over sodium sulfate and concentrated. The crude product was purified by column chromatography (4% methanol in methylene chloride). Yield: 52%

Stage (iii): 9-(Pyridin-3-yl)-9-(2-(pyrrolidin-1-yl)ethoxy)-3-azaspiro[5.5]undecane tert-Butyl 9-(pyridin-3-yl)-9-(2-(pyrrolidin-1-yl)ethoxy)-3-azaspiro[5.5]undecane-3-carboxylate (0.33 mmol, 1 eq) was dissolved in methylene chloride (3.5 ml). TFA (0.7 ml) was added at 0° C. and the mixture was stirred at 25° C. for 1 h. The solvent was concentrated to dryness under reduced pressure and the resulting desired product was employed in the next stage without further purification.

2. Sulfonyl Chlorides/PFP Esters

Preparation of 4-methoxy-2,6-dimethylbenzenesulfonyl chloride: Stage (ia) and perfluorophenyl 4-methoxy-2,6-dimethylbenzenesulfonate: Stage (ib)

Stage (ia): 4-Methoxy-2,6-dimethylbenzenesulfonyl chloride

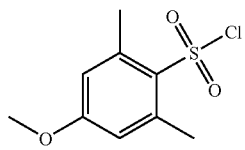

Chlorosulfonic acid (12 ml, 184 mmol) in methylene chloride (60 ml) was slowly added dropwise to a solution, cooled to 0° C., of 3,5-dimethylanisole (5 g, 36.71 mmol) in methylene chloride (60 ml) over the course of 10 min. The reaction mixture was stirred for a further 10 min and subsequently slowly added dropwise to ice-water (300 ml) and the mixture was stirred until the ice had melted. The phases were separated and the aqueous phase was extracted with methylene chloride (50 ml). The combined organic phases were washed with saturated sodium chloride solution (50 ml), dried ($Na_2SO_4$) and concentrated in vacuo. It may be noted that the ratio of anisole/chlorosulfuric acid can be reduced to 1/2.3 without losses with respect to the yield.

Stage (ib): Perfluorophenyl 4-methoxy-2,6-dimethylbenzenesulfonate

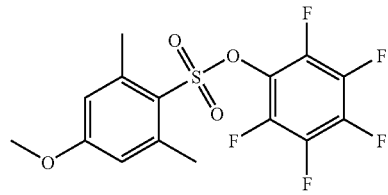

A solution of pentafluorophenol (6.75 g, 36.71 mmol) and triethylamine (10.2 ml, 73.4 mmol) in methylene chloride (50 ml) was stirred at room temperature for 30 min. A solution of the sulfonyl chloride prepared in methylene chloride (50 ml) was subsequently slowly added dropwise. The reaction mixture was stirred at room temperature for 1 h. Saturated sodium bicarbonate solution (50 ml) was added to the mixture and the organic phase was washed with saturated sodium chloride solution (50 ml), dried over sodium sulfate and concentrated in vacuo. The crude product was purified by column chromatography (silica gel) with hexane/diethyl ether/methylene chloride (20:1:1). Yield: 8.42 g (60%)

Synthesis of the Example Compounds According to the Invention

Example 32

(S)-1-(3-(1-(4-Methoxy-2,6-dimethylphenylsulfonyl)pyrrolidin-2-yl)propylsulfonyl)-4-(1-methylpiperidin-4-yl)piperazine

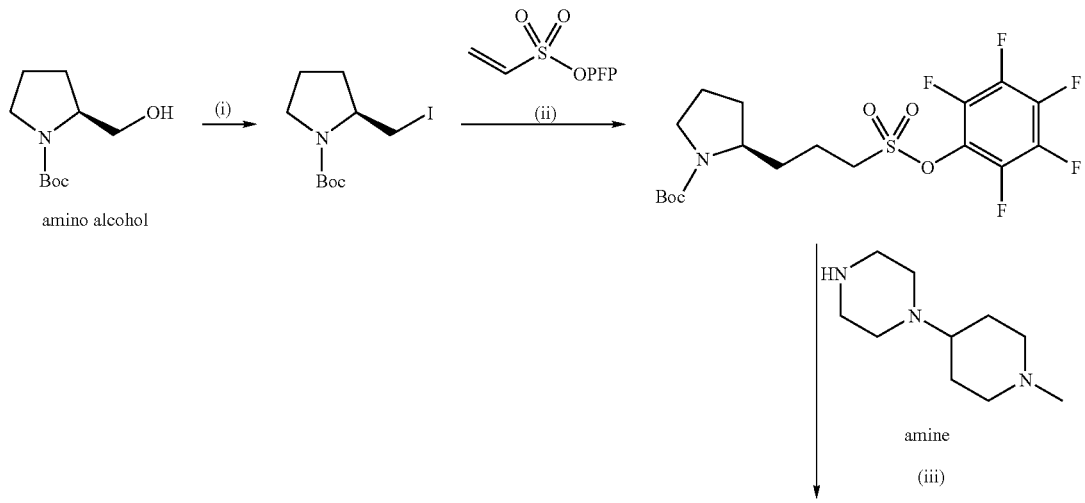

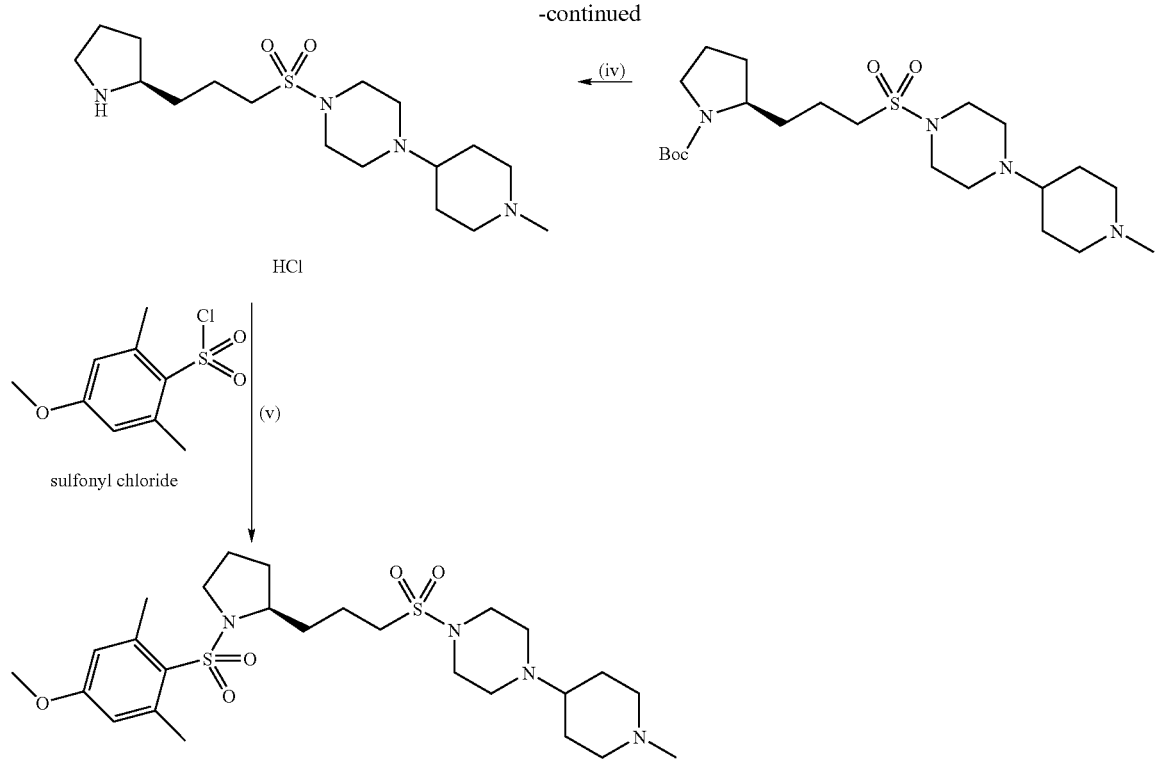

Stage (i): (S)-tert-Butyl 2-(iodomethyl)pyrrolidine-1-carboxylate (S)-(−)-N-Boc-prolinol (10 g, 49.7 mmol), imidazole (6.76 g, 99.4 mmol) and triphenylphosphine (19.5 g, 74.5 mmol) were dissolved in diethyl ether (210 ml) and acetonitrile (80 ml) and the solution was cooled to 0° C. under an inert gas. Iodine (17.7 g, 70 mmol) was added in portions at this temperature. The yellow suspension was stirred for 15 h, and warmed to room temperature during this procedure. Addition of sodium thiosulfate solution (50 ml, 5 mol/l), stir for 5 min, the phases were separated. The aqueous phase was extracted with diethyl ether (2×100 ml) and the combined organic phases were washed with copper sulfate solution (30 ml, 5%) and sodium chloride solution (30 ml, saturated), dried over sodium sulfate and concentrated in vacuo. The crude product was purified by column chromatography (silica gel) with hexane/diethyl ether (6:1). Yield: 10.57 g (68%)

Stage (ii): (S)-tert-Butyl 2-(3-(perfluorophenoxysulfonyl)propyl)pyrrolidine-1-carboxylate 1-Ethylpiperidine hypophosphite (30 g, 168 mmol) were weighed into the reaction flask under an inert gas, and methylene chloride (100 ml) was added. The solution was cooled with ice-water and 2,3,4,5,6-pentafluorophenyl 1-ethylenesulfonate (5.06 g, 18.5 mmol) [Org. Lett.; 2002; 4(15); 2549-2551] and (S)-tert-butyl 2-(iodomethyl)pyrrolidine-1-carboxylate (5.22 g, 16.8 mmol) was added at 10° C. Triethylborane solution (1.6 ml, 1 mol/l) was added and compressed air was then passed through the mixture for 5 sec. After stirring for min the addition of triethylborane solution-compressed air was repeated with the same amount. The cooling bath was removed, the mixture was stirred for 10 min and the reaction mixture was then washed with water (20 ml) and saturated sodium chloride solution (20 ml), dried over sodium sulfate and concentrated in vacuo. The crude product was purified by column chromatography (silica gel) with hexane/diethyl ether (2:1). Yield: 2.81 g (36%)

Stage (iii): (S)-tert-Butyl 2-(3-(4-(1-methylpiperidin-4-yl)piperazin-1-ylsulfonyl)propyl)pyrrolidine-1-carboxylate (S)-tert-Butyl 2-(3-(perfluorophenoxysulfonyl)propyl) pyrrolidine-1-carboxylate (2.8 g, 6.099 mmol) and 1-(1-methylpiperidin-4-yl)piperazine (1.676 g, 9.148 mmol) were dissolved in tetrahydrofuran (40 ml), 1,8-diazabicyclo[5.4.0] undec-7-ene (2.7 ml, 18.297 mmol) was added under an inert gas and the mixture was refluxed for 2 h. Ethyl acetate and saturated sodium bicarbonate solution (50 ml of each) were added, the phases were separated and the aqueous phase was extracted with ethyl acetate (2×50 ml). The combined organic phases were washed with saturated sodium bicarbonate solution (40 ml), dried over sodium sulfate and concentrated in vacuo. The crude product was purified by column chromatography (silica gel) with ethyl acetate/methanol/methylene chloride/ammonia (25% aq) (300:100:50:1). Yield: quantitative Stage (iv): (S)-1-(1-Methylpiperidin-4-yl)-4-(3-(pyrrolidin-2-yl)propylsulfonyl)piperazine hydrochloride Hydrogen chloride in methanol (5 ml, 1.25 mol/l) was added to (S)-tert-butyl 2-(3-(4-(1-methylpiperidin-4-yl)piperazin-1-ylsulfonyl)propyl)pyrrolidine-1-carboxylate (0.27 g, 0.589 mmol) and the mixture was refluxed. After 1 h ethyl acetate (10 ml) and diethyl ether (20 ml) were added to the suspension, the mixture was stirred in an ice bath for 1 h and the precipitate was filtered out with suction, washed with diethyl ether and dried in vacuo. Yield: 0.22 g (79%)

Stage (v): (S)-1-(3-(1-(4-Methoxy-2,6-dimethylphenylsulfonyl)pyrrolidin-2-yl)propylsulfonyl)-4-(1-methylpiperidin-4-yl)piperazine (Example 32)

(S)-1-(1-Methylpiperidin-4-yl)-4-(3-(pyrrolidin-2-yl)propylsulfonyl)piperazine trihydrochloride (0.3 g, 0.643 mmol) was dissolved in methylene chloride (5 ml) and triethylamine (0.4 ml, 2.894 mmol), 4-methoxy-2,6-trimethylbenzenesulfonic acid chloride (0.77 mmol) in methylene chloride (5 ml) was added and the mixture was stirred at room temperature for 15 h. Saturated sodium bicarbonate solution (10 ml) was added to the reaction mixture and the phases were separated. The aqueous phase was extracted with methylene chloride (20 ml) and the combined organic phases were dried over sodium sulfate and concentrated in vacuo. The crude product was purified by column chromatography (silica gel) with ethyl acetate/methylene chloride/methanol/ammonia (25 aq) (200:400:50:1). Yield: 0.17 g (47%). MS, m/z 557.2 (MH$^+$)

The example compounds listed in the following table were prepared from the corresponding educts closely in accordance with the process described for Example 32. The reaction temperatures and equivalent amounts of the reagents employed may deviate in analogous reactions. The particular course of the reaction was monitored by thin layer chromatography [stage (ii) to (v)] and the reaction times were adapted accordingly on the basis of this. The educts employed are commercially available or were prepared as described.

Re Stage (iv):

To remove the protective group, trifluoroacetic acid (5 eq) in methylene chloride (1 ml/0.1 mmol) was used in Example 15 as an alternative to hydrogen chloride in methanol. In order to remove the protective group with hydrogen chloride in methanol, the working up varied in some examples in that
(i) as an alternative to the addition of ethyl acetate/diethyl ether to the reaction solution for the precipitation (after concentration in vacuo), methyl ethyl ketone/diethyl ether/ethanol (5:5:1); methyl ethyl ketone/ethanol (10:1), diethyl ether/ethanol (10:1), ethyl acetate/diethyl ether (1:4) or other suitable solvents/solvent mixtures were also used;
(ii) in some cases the hydrochloride formed was filtered out with suction directly from the methanolic reaction solution and washed with diethyl ether, or
(iii) no precipitation of the hydrochloride was carried out, but the reaction mixture was dried in vacuo.

Re Stage (v):

(i) The particular amount of triethylamine employed was adapted to the stoichiometry of the amine hydrochloride (xHCl) or trifluoroacetate employed.
(ii) As an alternative to tetrahydrofuran, methylene chloride or pyridine were also used as solvents in some examples (the preferred solvent was methylene chloride).
(iii) In some examples the corresponding hydrochloride (xHCl) was subsequently precipitated in the presence of HCl in methanol or chlorotrimethylsilane in a suitable solvent or solvent mixture at temperatures of between 0° C. and room temperature.

| Example no. | Example compound | Amino alcohol employed in stage (I) | Amine employed in stage (III) | Sulfonyl chloride/ PFP ester employed in stage (v) | HCL preparation of the ex. compound/ comments | Yield (stage (v)) | Analysis (LC/MS) |
|---|---|---|---|---|---|---|---|
| 1 | | (R)-(+)-N-Boc-3-pyrrolidinol | 4-(2-Pyrrolidinoethyl)-piperidine | 2,4,6-Trimethylbenzenesulfonyl chloride | — | 99% | m/z = 526.2 [MH]$^+$ |
| 2 | | (R)-(+)-N-Boc-prolinol | 1-(4-Pyridyl)piperazine | Naphthalene-2-sulfonyl chloride | 1.2 eq of TMSCl MEK/ diethyl ether 1/1 5 ml/0.1 mmol | 58% | m/z = 529.2 [MH]$^+$ |
| 3 | | (R)-(+)-N-Boc-3-pyrrolidinol | 4-(2-Pyrrolidinoethyl)-piperidine | 1-Benzothiophene-3-sulfonyl chloride | — | 76% | m/z = 540.2 [MH]$^+$ |
| 4 | | (R)-1-(Boc)-2-azetidine-methanol | 4-(2-Pyrrolidinoethyl)-piperidine | 2,4,6-Trimethylbenzenesulfonyl chloride | 1.2 eq of TMSCl MEK/ diethyl ether 1/1 5 ml/0.1 mmol | 63% | m/z = 426.2 [MH]$^+$ |

-continued

| Example no. | Example compound | Amino alcohol employed in stage (I) | Amine employed in stage (III) | Sulfonyl chloride/ PFP ester employed in stage (v) | HCL preparation of the ex. compound/ comments | Yield (stage (v)) | Analysis (LC/MS) |
|---|---|---|---|---|---|---|---|
| 5 | 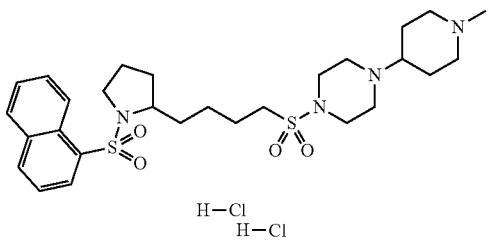 | N-Boc-2-(pyrrolidin-2-yl)ethanol | 1-(1-Methyl-4-piperidin-yl)piperazine | Naphthalene-1-sulfonyl chloride | 2.2 eq of TMSCl MEK/ diethyl ether 1/1 5 ml/0.1 mmol + ethanol | 88% | m/z = 563.2 [MH]+ |
| 6 | 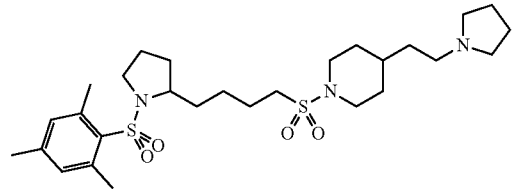 | N-Boc-2-(pyrrolidin-2-yl)ethanol | 4-(2-Pyrrolidinoethyl)-piperidine | 2,4,6-Trimethyl-benzene-sulfonyl chloride | — | 99% | m/z = 554.3 [MH]+ |
| 7 | 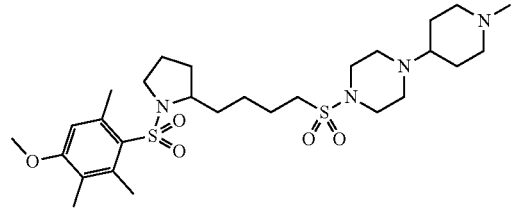 | N-Boc-2-(pyrrolidin-2-yl)ethanol | 1-(1-Methyl-4-piperidin-yl)piperazine | 4-Methoxy-2,3,6-trimethyl-benzene-sulfonyl chloride | — | 86% | m/z = 585.3 [MH]+ |
| 8 | 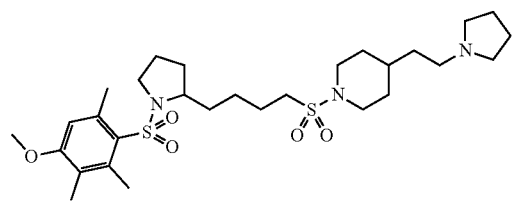 | N-Boc-2-(pyrrolidin-2-yl)ethanol | 4-(2-Pyrrolidinoethyl)-piperidine | 4-Methoxy-2,3,6-trimethyl-benzene-sulfonyl chloride | — | 99% | m/z = 584.3 [MH]+ |
| 9 | 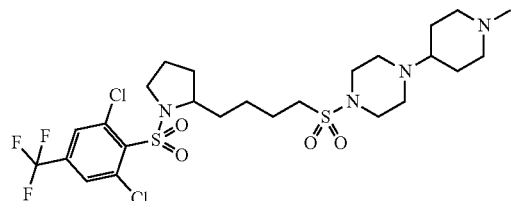 | N-Boc-2-(pyrrolidin-2-yl)ethanol | 1-(1-Methyl-4-piperidin-yl)piperazine | 2,6-Dichloro-4-(trifluoro-methyl)benzene-sulfonyl chloride | — | 59% | m/z = 649.1 [MH]+ |
| 10 | 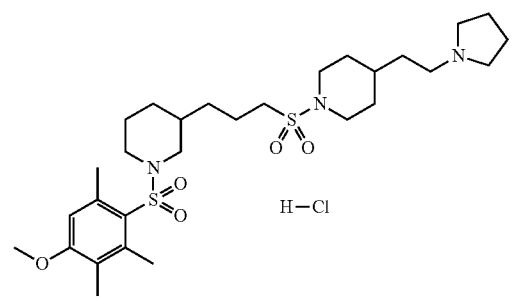 | N-Boc-piperidin-3-ylmethanol | 4-(2-Pyrrolidindoethyl)-piperidine | 4-Methoxy-2,3,6-trimethyl-benzene-sulfonyl chloride | 1.2 eq of TMSCl MEK/ diethyl ether 1/1 5 ml/0.1 mmmol | 85% | m/z = 584.3 [MH]+ |

-continued

| Example no. | Example compound | Amino alcohol employed in stage (I) | Amine employed in stage (III) | Sulfonyl chloride/ PFP ester employed in stage (v) | HCL preparation of the ex. compound/ comments | Yield (stage (v)) | Analysis (LC/MS) |
|---|---|---|---|---|---|---|---|
| 11 | | N-Boc-piperidin-3-ylmethanol | 4-(2-Pyrrolidinoethyl)-piperidine | 2,4,6-Trimethyl-benzene-sulfonyl chloride | 1.2 eq of TMSCl MEK/ diethyl ether 1/1 5 ml/0.1 mmol | 58% | m/z = 553.3 [MH]+ |
| 12 | | N-Boc-piperidin-4-ylmethanol | 4-(2-Pyrrolidinoethyl)-piperidine | 2,4,6-Trimethyl-benzene-sulfonyl chloride | — | 96% | m/z = 554.3 [MH]+ |
| 13 | | N-Boc-piperidin-4-ylmethanol | 1-(1-Methyl-4-piperidin-yl)piperazine | 2,4,6-Trimethyl-benzene-sulfonyl chloride | — | 80% | m/z = 555.3 [MH]+ |
| 14 | | N-Boc-4-hydroxy-piperidine | 4-(2-Pyrrolidinoethyl)-piperidine | 2,6-Dichloro-4-(trifluoromethyl)benzene-sulfonyl chloride | — | 27% | m/z = 634.1 [MH]+ |
| 15 | | N-Boc-issoxazolin-4-ol | 4-(2-Pyrrolidinoethyl)-piperidine | 4-Methoxy-2,3,6-trimethyl-benzene-sulfonyl chloride | — | 40% | m/z = 558.2 [MH]+ |
| 16 | | (R)-(+)-N-Boc-3-pyrrolidinol | 4-(2-Pyrrolidinoethyl)-piperidine | 4-Methoxy-2,3,6-trimethyl-benzene-sulfonyl chloride | 1.2 eq of TMSCl 5 MEK/ diethyl ether 1/1 ml/0.1 mmol | 93% | m/z = 556.2 [MH]+ |
| 17 | | (R)-(+)-N-Boc-3-pyrrolidinol | 4-(2-Pyrrolidinoethyl)-piperidine | 2,3-Dichloro-benzene-sulfonyl chloride | 1.2 eq of TMSCl MEK/ diethyl ether 1/1 5 ml/0.1 mmmol | 88% | m/z = 552.1 [MH]+ |

-continued

| Example no. | Example compound | Amino alcohol employed in stage (I) | Amine employed in stage (III) | Sulfonyl chloride/ PFP ester employed in stage (v) | HCL preparation of the ex. compound/ comments | Yield (stage (v)) | Analysis (LC/MS) |
|---|---|---|---|---|---|---|---|
| 18 | 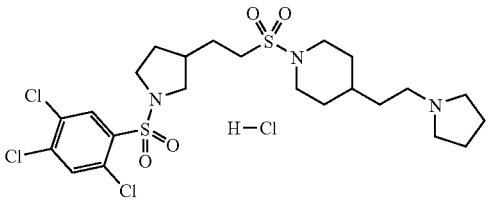 | (R)-(+)-N-Boc-3-pyrrolidinol | 4-(2-Pyrrolidinoethyl)-piperidine | 2,4,5-Trichloro-benzene-sulfonyl chloride | 1.2 eq of TMSCl MEK/ diethyl ether 1/1 5 ml/0.1 mmol | 95% | m/z = 586.1 [MH]+ |
| 19 | 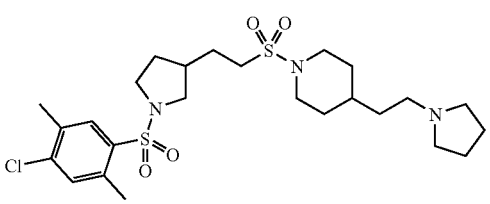 | (R)-(+)-N-Boc-3-pyrrolidinol | 4-(2-Pyrrolidinoethyl)-piperidine | 4-Chloro-2,5-dimethyl-benzene-sulfonyl chloride | — | 94% | m/z = 546.2 [MH]+ |
| 20 | 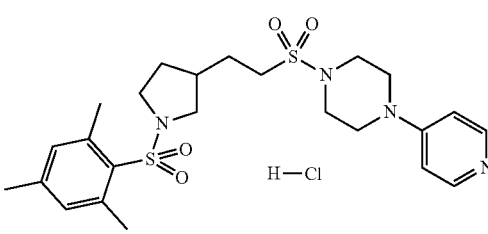 | (R)-(+)-N-Boc-3-pyrrolidinol | 1-(4-Pyridyl)piperazine | 2,4,6-Trimethyl-benzene-sulfonyl chloride | 2 eq of TMSCl MEK/ diethyl ether 1/1 5 ml/0.1 mmol | 55% | m/z = 507.2 [MH]+ |
| 21 | 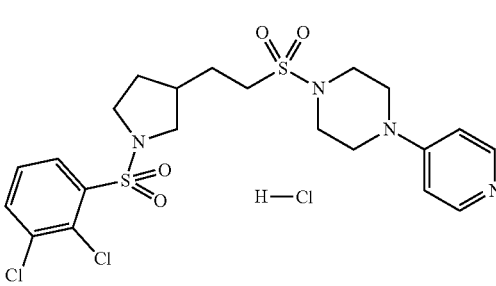 | (R)-(+)-N-Boc-3-pyrrolidinol | 1-(4-Pyridyl)piperazine | 2,3-Dichloro-benzene-sulfonyl chloride | 2 eq of TMSCl MEK/ diethyl ether 1/1 5ml/0.1 mmol | 62% | * |
| 22 | 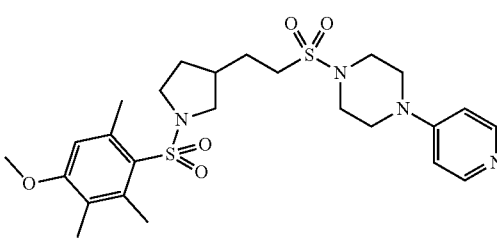 | (R)-(+)-N-Boc-3-pyrrolidinol | 1-(4-Pyridyl)piperazine | 4-Methoxy-2,3,6-trimethyl-benzene-sulfonyl chloride | — | 59% | m/z = 537.2 [MH]+ |
| 23 | 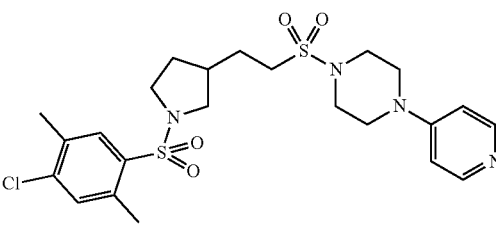 | (R)-(+)-N-Boc-3-pyrrolidinol | 1-(4-Pyridyl)piperazine | 4-Chloro-2,5-dimethyl-benzene-sulfonyl chloride | — | 75% | m/z = 527.1 [MH]+ |

| Example no. | Example compound | Amino alcohol employed in stage (I) | Amine employed in stage (III) | Sulfonyl chloride/ PFP ester employed in stage (v) | HCL preparation of the ex. compound/ comments | Yield (stage (v)) | Analysis (LC/ MS) |
|---|---|---|---|---|---|---|---|
| 24 | | (R)-(+)-N-Boc-3-pyrrolidinol | 1-(4-Pyridyl)piperazine | 3,4-Dichlorobenzenesulfonyl chloride | 2 eq of TMSCl MEK/diethyl ether 1/1 5 ml/0.1 mmol | 31% | m/z = 533.1 [MH]+ |
| 25 | | (R)-(+)-N-Boc-3-pyrrolidinol | 4-(2-Pyrrolidinoethyl)piperidin | Perfluorophenyl 4-methoxy-2,6-dimethylbenzenesulfonate | 1.2 eq of TMSCl MEK/diethyl ether 1/1 5 ml/0.1 mmol | 66% | m/z = 542.2 [MH]+ |
| 27 | | (S)-(−)-N-Boc-prolinol | 1-(1-Methyl-4-piperidinyl)piperazine | 2-Chloro-6-methylbenzenesulfonyl chloride | — | 97% | R$_t$ = 2.04 min; m/z = 547.1 [MH]+ |
| 28 | | (S)-(−)-N-Boc-prolinol | 1-(1-Methyl-4-piperidinyl)piperazine | 2,4,6-Trimethylbenzenesulfonyl chloride | — | 98% | R$_t$ = 2.5 min; m/z = 601.0 [MH]+ |
| 29 | | (S)-(−)-N-Boc-prolinol | 1-(1-Methyl-4-piperidinyl)piperazine | 4-Chloro-2,5-dimethylbenzenesulfonyl chloride | — | 90% | R$_t$ = 2.5 min; m/z = 561.1 [MH]+ |
| 30 | | (S)-(−)-N-Boc-prolinol | 1-(1-Methyl-4-piperidinyl)piperazine | Naphthalene-1-sulfonyl chloride | — | 97% | R$_t$ = 2.1 min; m/z = 549.2 [MH]+ |
| 31 | | (S)-(−)-N-Boc-prolinol | 1-(1-Methyl-4-piperidinyl)piperazine | 2,4-Dichlorobenzenesulfonyl chloride | — | 75% | R$_t$ = 2.3 min; m/z = 567.1 [MH]+ |

-continued

| Example no. | Example compound | Amino alcohol employed in stage (I) | Amine employed in stage (III) | Sulfonyl chloride/ PFP ester employed in stage (v) | HCL preparation of the ex. compound/ comments | Yield (stage (v)) | Analysis (LC/ MS) |
|---|---|---|---|---|---|---|---|
| 33 | | (S)-(−)-N-Boc-prolinol | 1-(1-Methyl-4-piperidin-yl)piperazine | 2,2-Diphenyl-ethane-sulfonyl chloride | — | 60% | $R_t$ = 2.6 min; m/z = 603.2 [MH]$^+$ |
| 34 | | (R)-(+)-N-Boc-prolinol | 1-(1-Methyl-4-piperidin-yl)piperazine | 4-Methoxy-2,6-dimethyl-benzene-sulfonyl chloride | — | 58% | $R_t$ = 2.0 min; m/z = 557.2 [MH]$^+$ |
| 35 | | (S)-(−)-N-Boc-prolinol | 1-(1-Methyl-4-piperidin-yl)piperazine | 3-(trifluoro-methyl)ben-zene-sulfonyl chloride | — | 59% | $R_t$ = 2.2 min; m/z = 567.2 [MH]$^+$ |
| 36 | | ((2S,4S)-N-Boc-4-fluoro-pyrrolidin-2-yl)methanol | 4-(Piperidin-4-yloxy)py-ridine dihydro-chloride | 4-Methoxy-2,6-dimethyl-benzene-sulfonyl chloride | — | 65% | $R_t$ = 3.0 min; m/z = 570.0 [MH]$^+$ |
| 40 | | (S)-(−)-N-Boc-prolinol | 2-(Piperazin-1-yl)thiazole | 4-Methoxy-2,3,6-trimethyl-benzene-sulfonic acid chloride | — | 78% | m/z = 557.2 [MH]$^+$ |
| 41 | | (R)-(+)-N-Boc-prolinol | 1-(1-Methyl-4-piperidin-yl)piperazine | 2,4,6-Trimethyl-benzene-sulfonyl chloride | 1.2 eq of TMSCl MEK/ diethyl ether 1/1 5 ml/0.1 mmol | 52% | m/z = 541.2 [MH]$^+$ |
| 42 | | N-Boc-2-(pyrrolidin-2-yl)ethanol | 1-(1-Methyl-4-piperidin-yl)piperazine | 2,4,6-Trimethyl-benzene-sulfonyl cholride | 2.2 eq of TMSCl MEK/ diethyl ether 1/1 5 ml/0.1 mmol + methanol | 65% | m/z = 555.3 [MH]$^+$ |

| Example no. | Example compound | Amino alcohol employed in stage (I) | Amine employed in stage (III) | Sulfonyl chloride/ PFP ester employed in stage (v) | HCL preparation of the ex. compound/ comments | Yield (stage (v)) | Analysis (LC/MS) |
|---|---|---|---|---|---|---|---|
| 43 | 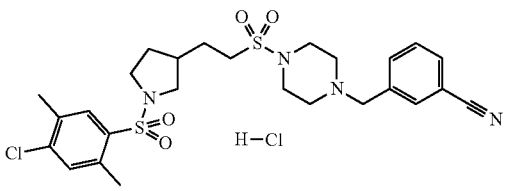 | (R)-(+)-N-Boc-3-pyrrolidinol | 1-(3-Cyanobenzyl)piperazine | 4-Chloro-2,5-dimethyl-benzene-sulfonyl chloride | 1.2 eq of TMSCl MEK/diethyl ether 1/1 5 ml/0.1 mmol | 84% | m/z = 565.1 [MH]+ |
| 44 | 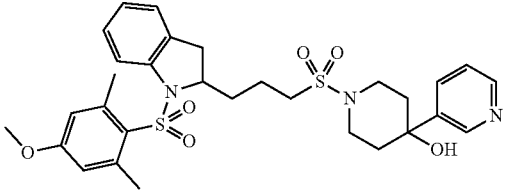 | N-Boc-indolin-2-ylmethanol | 4-(Pyridin-3-yl)piperidin-4-ol | 4-Methoxy-2,6-dimethyl-benzene-sulfonyl chloride | — | 30% | $R_t$ = 3.8 min; m/z = 600.2 [MH]+ |
| 45 | 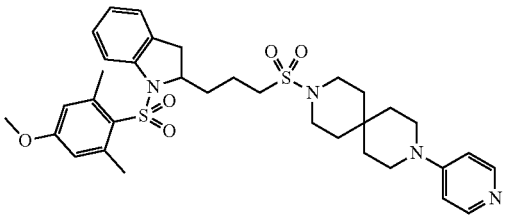 | N-Boc-indolin-2-ylmethanol | 3-(Pyridin-4-yl)-3,9-diazaspiro[5.5]undecane dihydrochloride | 4-Methoxy-2,6-dimethyl-benzene-sulfonyl chloride | — | 40% | $R_t$ = 3.9 min; m/z = 653.3 [MH]+ |
| 62 | 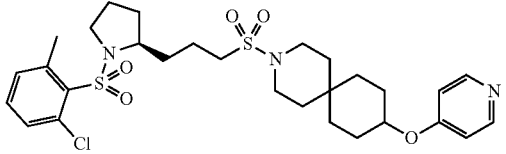 | (S)-(−)-N-Boc-prolinol | 9-Pyridin-4-yloxy)-3-azaspiro[5.5]undecane dihydrochloride | 2-Chloro-6-methyl-benzene-sulfonyl chloride | (a) | 56% | $R_t$ = 3.8 min; m/z = 610.4 [MH]+ |
| 63 | 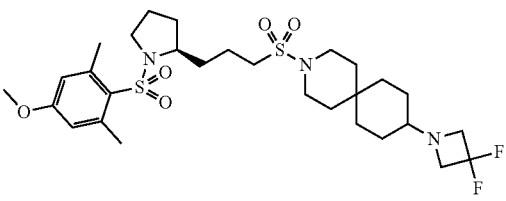 | (S)-(−)-N-Boc-prolinol | 9-(3,3-Difluoro-azetidin-1-yl)-3-azaspiro[5.5]undecane dihydrochloride | 4-Methoxy-2,6-dimethyl-benzene-sulfonyl chloride | (a) | 44% | $R_t$ = 3.7 min; m/z = 618.5 [MH]+ |
| 64 | 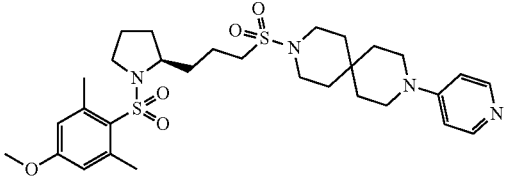 | (S)-(−)-N-Boc-prolinol | 3-(Pyridin-4-yl)-3,9-diazaspiro[5.5]undecane dihydrochloride | 4-Methoxy-2,6-dimthyl-benzene-sulfonyl chloride | (a) | 90% | $R_t$ = 3.6 min; m/z = 605.4 [MH]+ |
| 65 | 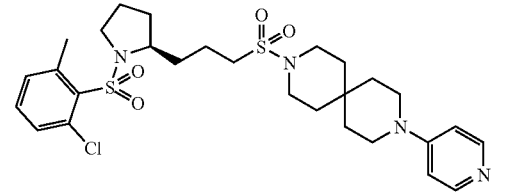 | (S)-(−)-N-Boc-prolinol | 3-(Pyridin-4-yl)-3,9-diazaspiro[5.5]undecane dihydrochloride | 2-Chloro-6-methyl-benzene-sulfonyl chloride | (a) | 75% | $R_t$ = 3.6 min; m/z = 595.3 [MH]+ |

-continued

| Example no. | Example compound | Amino alcohol employed in stage (I) | Amine employed in stage (III) | Sulfonyl chloride/ PFP ester employed in stage (v) | HCL preparation of the ex. compound/ comments | Yield (stage (v)) | Analysis (LC/MS) |
|---|---|---|---|---|---|---|---|
| 66 | 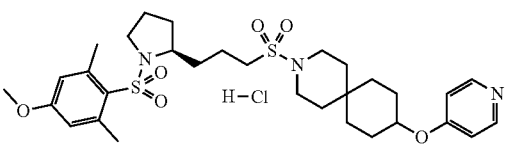 | (S)-(−)-N-Boc-prolinol | 9-(Pyridin-4-yloxy)-3-azaspiro[5.5]undecane dihydrochloride | 4-Methoxy-2,6-dimethyl-benzene-sulfonyl chloride | 2M HCl (2 eq) in diethyl ether acetone/ diethyl ether (a) | 41% | $R_t$ = 3.8 min; m/z = 620.5 [MH]$^+$ |
| 67 | 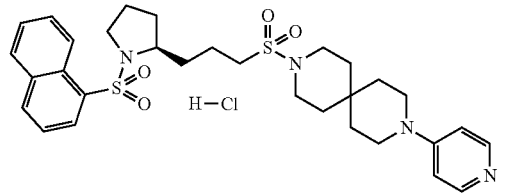 | (S)-(−)-N-Boc-prolinol | 3-(Pyridin-4-yl)-3,9-diazaspiro[5.5]undecane dihydrochloride | Naphthalene-1-sulfonyl chloride | 2M HCl (3 eq) in diethyl ether; MEK/ EtOH/ diethyl ether (a) | 61% | $R_t$ = 3.6 min; m/z = 597.3 [MH]$^+$ |
| 68 | 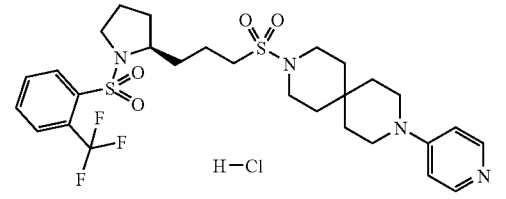 | (S)-(−)-N-Boc-prolinol | 3-(Pyridin-4-yl)-3,9-diazaspiro[5.5]undecane dihydrochloride | 3-(Trifluoromethyl)benzene-sulfonyl chloride | 2M HCl (3 eq) in diethyl ether; MEK/ EtOH/ diethyl ether (a) | 64% | $R_t$ = 3.5 min; m/z = 615.3 [MH]$^+$ |
| 75 | 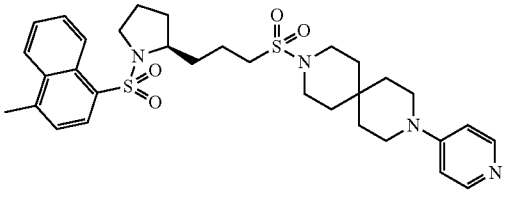 | (S)-(−)-N-Boc-prolinol | 3-(Pyridin-4-yl)-3,9-diazaspiro[5.5]undecane dihydrochloride | 4-Methyl-naphthalene-1-sulfonyl chloride | (a) | 73% | $R_t$ = 3.9 min; m/z = 611.3 [MH]$^+$ |
| 76 | 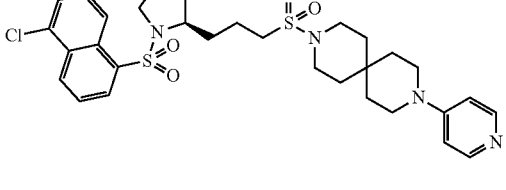 | (S)-(−)-N-Boc-prolinol | 3-(Pyridin-4-yl)-3,9-diazaspiro[5.5]undecane dihydrochloride | 5-Chloro-naphthalene-1-sulfonyl chloride | (a) | 82% | $R_t$ = 4.1 min; m/z = 631.3 [MH]$^+$ |
| 77 | 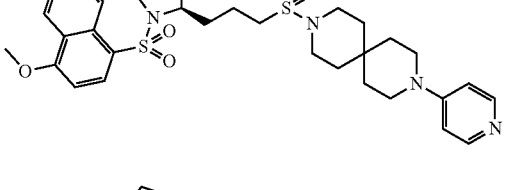 | (S)-(−)-N-Boc-prolinol | 3-(Pyridin-4-yl)-3,9-diazaspiro[5.5]undecane dihydrochloride | 4-Methoxy-naphthalene-1-sulfonyl chloride | (a) | 91% | $R_t$ = 3.8 min; m/z = 627.4 [MH]$^+$ |
| 78 | 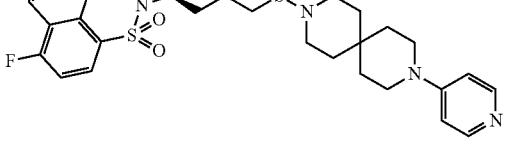 | (S)-(−)-N-Boc-prolinol | 3-(Pyridin-4-yl)-3,9-diazaspiro[5.5]undecane dihydrochloride | 4-Fluoro-naphthalene-1-sulfonyl chloride | (a) | 44% | $R_t$ = 3.8 min; m/z = 615.4 [MH]$^+$ |

-continued

| Example no. | Example compound | Amino alcohol employed in stage (I) | Amine employed in stage (III) | Sulfonyl chloride/ PFP ester employed in stage (v) | HCL preparation of the ex. compound/ comments | Yield (stage (v)) | Analysis (LC/MS) |
|---|---|---|---|---|---|---|---|
| 79 | | (S)-(−)-N-Boc-prolinol | 3-(Pyridin-4-yl)-3,9-diazaspiro[5.5]undecane dihydrochloride | 4-Chloronaphthalene-1-sulfonyl chloride | (a) | 63% | R$_t$ = 4.0 min; m/z = 631.3.3 [MH]$^+$ |
| 80 | | (S)-(−)-N-Boc-Prolinol | (1R,3S,5S)-8-(Azetidin-3-yl)-3-pyridin-4-yloxy-8-azabicyclo[3.2.1]octane trihydrochloride | 4-Methoxy-2,6-dimethyl-benzene-sulfonyl chloride | (a) | 43% | R$_t$ = 2.5 min; m/z = 633.4 [MH]$^+$ |
| 81 | | (S)-(−)-N-Boc-Prolinol | (1R,3S,5S)-8-(Azetidin-3-yl)-3-pyridin-4-yloxy-8-azabicyclo[3.2.1]octane trihydrochloride | 2-Chloro-6-methyl-benzene-sulfonyl chloride | (a) | 71% | R$_t$ = 2.4 min; m/z = 623.3 [MH]$^+$ |
| 82 | | (S)-(−)-N-Boc-Prolinol | 2-(Pyridin-4-yl)-2,7-diazaspiro[4.4]nonane dihydrochloride | 4-Methoxy-2,6-dimethyl-benzene-sulfonyl chloride | (a) | 83% | R$_t$ = 3.4 min; m/z = 577.3 [MH]$^+$ |
| 83 | | (S)-(−)-N-Boc-Prolinol | 2-(Pyridin-4-yl)-2,7-diazaspiro[4.4]nonane dihydrochloride | 2-Chloro-6-methyl-benzene-sulfonyl-chloride | (a) | 80% | R$_t$ = 3.4 min; m/z = 567.3 [MH]$^+$ |
| 84 | | (S)-(−)-N-Boc-Prolinol | 2-(Pyridin-4-yl)-2,7-diazaspiro[4.4]nonane dihydrochloride | 4-Methoxy-2,5-dimethyl-benzene-sulfonyl chloride | (a) | 94% | R$_t$ = 3.7 min; m/z = 577.4 [MH]$^+$ |
| 85 | | (S)-(−)-N-Boc-Prolinol | 8-(Pyridin-4-yl)-2,8-diazaspiro[4.5]decane dihydrochloride | 4-Methoxy-2,6-dimethyl-benzene-sulfonyl chloride | (a) | 79% | R$_t$ = 3.6 min; m/z = 591.4 [MH]$^+$ |

Example 21

* $^1$H NMR (600 MHz, DMSO-d$_6$) □ ppm 1.60 (m, 1H) 1.70-1.78 (m, 2H) 2.00-2.09 (m, 1H) 2.23-2.31 (m, 1H) 2.97 (t, J=9.06 Hz, 1H) 3.10-3.17 (m, 2H) 3.24-3.30 (m, 1H) 3.25-3.31 (m, 4H) 3.43 (td, J=8.88, 3.40 Hz, 1H) 3.52-3.58 (m, 1H) 3.79 (d, J=5.29 Hz, 4H) 7.24 (d, J=7.55 Hz, 2H) 7.57 (t, J=7.93 Hz, 1H) 7.94 (dd, J=7.93, 2.64 Hz, 2H) 8.30 (d, J=6.80 Hz, 2H) 13.71 (s, 1H)

(a) Alternative GWI stage (iii): The amine (free base or corresponding hydrochloride (xHCl)) (1.2 eq) was dissolved in THF or THF/DMF (5:2), N,N-diisopropylethylamine (3 eq) was added and the mixture was subsequently stirred at room temperature for 30 min. (S)-tert-Butyl 243-(perfluorophenoxysulfonyl)propyl)pyrrolidine-1-carboxylate (1 eq), dissolved in THF, was then added, followed by 1,8-diazabicyclo[5.4.0]undec-7-ene (2.5 eq) and the reaction mixture was stirred at room temperature for up to 3 d. The reaction mixture was concentrated in vacuo and the residue was taken up in saturated sodium bicarbonate solution and ethyl acetate. The phases were separated and the aqueous phase was extracted with ethyl acetate (2×). The combined organic phases were washed with saturated sodium chloride solution (1×), dried over sodium sulfate and concentrated in vacuo. The crude product was purified by column chromatography (silica gel).

| | Amine (R$^{10}$R$^{11}$NH) | Product (Boc-amine) | Yield |
|---|---|---|---|
| (a) | 4-(Piperidin-4-yloxy)pyridine dihydrochloride | (S)-tert-Butyl 2-(3-(4-(pyridin-4-yloxy)piperidin-1-ylsulfonyl)propyl)pyrrolidine-1-carboxylate | 43% (3.07 mmol) |
| (b) | (1R,3s,5S)-3-(Pyridin-4-yloxy)-8-azabicyclo[3.2.1]octane dihydrochloride | (S)-tert-Butyl 2-(3-((1R,3R,5S)-3-(pyridin-4-yloxy)-8-azabicyclo[3.2.1]octan-8-ylsulfonyl)propyl)pyrrolidine-1-carboxylate | 21% (2.03 mmol) |

Stage (ii): The Boc-amine just prepared (1 eq) was dissolved in methanol, acetyl chloride (5 eq) was added, while cooling with ice, and the mixture was stirred at room temperature for 16 h. The mixture was concentrated in vacuo.

| | Boc-amine employed in stage (ii) | Product (amine dihydrochloride) | Yield |
|---|---|---|---|
| (a) | (S)-tert-Butyl 2-(3-(4-(pyridin-4-yloxy)piperidin-1-ylsulfonyl)propyl)pyrrolidine-1-carboxylate | (S)-4-(1-(3-(Pyrrolidin-2-yl)propylsulfonyl)piperidin-4-yloxy)pyridine dihydrochloride | 97% (2.98 mmol) |
| (b) | (S)-tert-Butyl 2-(3-((1R,3R,5S)-3-(pyridin-4-yloxy)-8-azabicyclo[3.2.1]octan-8-ylsulfonyl)propyl)pyrrolidine-1-carboxylate | (1R,3R,5S)-3-(Pyridin-4-yloxy)-8-(3-((S)-pyrrolidin-2-yl)propylsulfonyl)-8-azabicyclo[3.2.1]octane dihydrochloride | >99% (2.11 mmol) |

Preparation of Further Examples Compounds According to the Invention from (S)-tert-butyl 2-(3-(perfluorophenoxysulfonyl)propyl)pyrrolidine-1-carboxylate

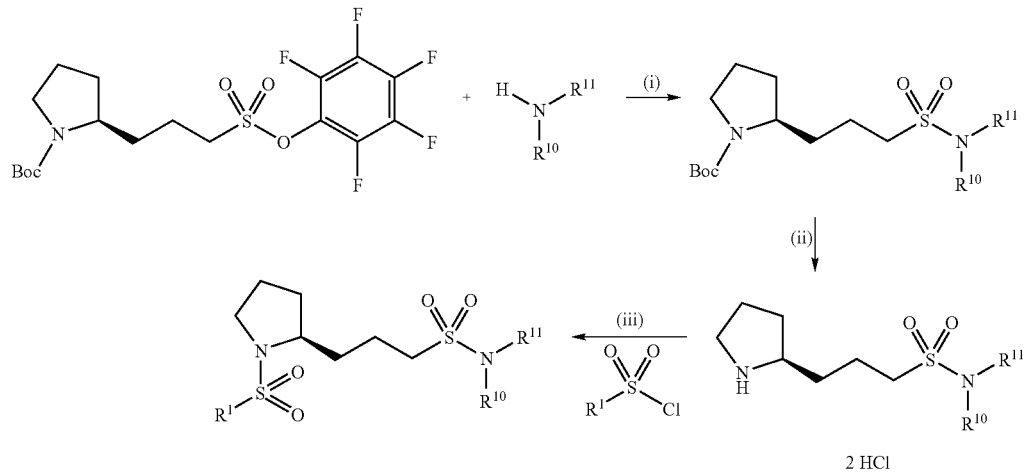

Stage (i): (S)-tert-Butyl 2-(3-(perfluorophenoxysulfonyl)propyl)pyrrolidine-1-carboxylate (see Example 32, stage (ii)) (1 eq) and amine (2 eq) were dissolved in tetrahydrofuran, 1,8-diazabicyclo[5.4.0]undec-7-ene (3 eq) was added under an inert gas and the mixture was refluxed for 1 h. Stirred at room temperature for 16 h. Ethyl acetate and saturated sodium bicarbonate solution were added, the phases were separated and the aqueous phase was extracted with ethyl acetate. The combined organic phases were washed with saturated sodium chloride solution, dried over sodium sulfate and concentrated in vacuo. The crude product was purified by column chromatography (silica gel, ethyl acetate/methanol/methylene chloride, 50:50:1).

Stage (iii), GWI-1: The corresponding amine dihydrochloride (~0.5 mmol) was dissolved in methylene chloride (3.0 ml) and pyridine (6.0 ml), the desired sulfonyl chloride (~0.9 mmol) was added and the mixture was stirred at room temperature for 15 h. The reaction mixture was diluted with ethyl acetate (50 ml), washed four times with saturated sodium bicarbonate solution (30 ml) and saturated sodium chloride solution (20 ml), dried over magnesium sulfate and concentrated in vacuo.

The crude product was purified by column chromatography (silica gel, ethyl acetate/hexane gradient 80:20 to 90:10).

Stage (iii), GWI-2: The corresponding amine dihydrochloride (~0.25 mmol; 1 eq) was dissolved in a mixture of methylene chloride (2.6 ml) and triethylamine (4 eq), the desired sulfonyl chloride (2 eq) was added and the mixture was stirred at room temperature for 15 h. Saturated sodium bicarbonate solution (3.0 ml) was added to the reaction mixture and the phases were separated. The organic phase was washed twice with saturated sodium bicarbonate solution (3.0 ml) and passed over a ready-made magnesium sulfate cartridge for drying, this was rinsed with 2.0 ml methylene chloride and the combined organic phases were concentrated in vacuo. The crude product was purified by column chromatography (silica gel, methylene chloride/methanol gradient 99:1 to 96:4).

The example compounds listed in the following table were prepared from the corresponding educts closely in accordance with the process just described. The reaction temperatures and equivalent amounts of the reagents employed may deviate in analogous reactions. The particular course of the reaction was monitored by thin layer chromatography and the reaction times were adapted accordingly on the basis of this.

| Example no. | Example compound | Amine dihydrochloride employed | Sulfonyl chloride employed | Yield (%) | Analysis (LC/MS) | Synthesized by/ comments |
|---|---|---|---|---|---|---|
| 46 | | (S)-4-(1-(3-(Pyrrolidin-2-yl)propyl-sulfonyl)piperidin-4-yloxy)pyridine dihydrochloride | 2-Chloro-6-methyl benzene-sulfonyl chloride | 26% (0.155 mmol) | $R_t = 3.1$ min; m/z = 542.2 $[MH]^+$ | GWI1 |
| 47 | | (S)-4-(1-(3-(Pyrrolidin-2-yl)propyl-sulfonyl)piperidin-4-yloxy)pyridine dihydrochloride | 4-Methoxy-2,6-dimethyl-benzene-sulfonyl chloride | 19% (0.109 mmol) | $R_t = 3.2$ min; m/z = 552.3 $[MH]^+$ | GWI1/(a) |
| 48 | | (S)-4-(1-(3-(Pyrrolidin-2-yl)propyl-sulfonyl)piperidin-4-yloxy)pyridine dihydrochloride | 2-(Trifluoromethyl) benzene-sulfonyl chloride | 40% (0.094 mmol) | $R_t = 3.4$ min; m/z = 562.3 $[MH]^+$ | GWI2 |
| 49 | | (S)-4-(1-(3-(Pyrrolidin-2-yl)propyl-sulfonyl)piperidin-4-yloxy)pyridine dihydrochloride | Naphthalene-2-sulfonyl chloride | 56% (0.130 mmol) | $R_t = 3.5$ min; m/z = 544.3 $[MH]^+$ | GWI2 |
| 50 | | (S)-4-(1-(3-(Pyrrolidin-2-yl)propyl-sulfonyl)piperidin-4-yloxy)pyridine dihydrochloride | Naphthalene-1-sulfonyl chloride | 97% (0.228 mmol) | $R_t = 3.5$ min; m/z = 544.3 $[MH]^+$ | GWI2 |
| 51 | | (S)-4-(1-(3-(Pyrrolidin-2-yl)propyl-sulfonyl)piperidin-4-yloxy)pyridine dihydrochloride | 2,4-Dichloro-benzene-1-sulfonyl chloride | 85% (0.199 mmol) | $R_t = 3.6$ min; m/z = 582.2 $[MH]^+$ | GWI2 |
| 52 | | (S)-4-(1-(3-(Pyrrolidin-2-yl)propyl-sulfonyl)piperidin-4-yloxy)pyridine dihydrochloride | 2,3-Dichloro-benzene-1-sulfonyl chloride | 78% (0.184 mmol) | $R_t = 3.5$ min; m/z = 562.2 $[MH]^+$ | GWI2 |

-continued

| Example no. | Example compound | Amine dihydrochloride employed | Sulfonyl chloride employed | Yield (%) | Analysis (LC/MS) | Synthesized by/ comments |
|---|---|---|---|---|---|---|
| 53 | | (S)-4-(1-(3-(Pyrrolidin-2-yl)propyl-sulfonyl)piperidin-4-yloxy)pyridine dihydrochloride | 4-Chloro-2,5-Dimethyl-benzene-sulfonyl chloride | 66% (0.154 mmol) | $R_t$ = 3.7 min; m/z = 556.3 [MH]$^+$ | GWI2 |
| 54 | | (1R,3R,5S)-3-(Pyridin-4-yloxy)-8-(3-((S)-pyrrolidin-2-yl)propylsulfonyl)-8-azabicyclo[3.2.1]octane dihydrochloride | 4-Methoxy-2,6-dimethyl-benzene-sulfonyl chloride | 41% (0.106 mmol) | $R_t$ = 3.6 min; m/z = 578.4 [MH]$^+$ | GWI2 |
| 55 | | (1R,3R,5S)-3-(Pyridin-4-yloxy)-8-(3-((S)-pyrrolidin-2-yl)propylsulfonyl)-8-azabicyclo[3.2.1]octane dihydrochloride | 2-Chloro-6-methyl-benzene-sulfonyl chloride | 69% (0.180 mmol) | $R_t$ = 3.5 min; m/z = 568.3 [MH]$^+$ | GWI2 |
| 56 | | (1R,3R,5S)-3-(Pyridin-4-yloxy)-8-(3-((S)-pyrrolidin-2-yl)propylsulfonyl)-8-azabicyclo[3.2.1]octane dihydrochloride | 2-(Trifluoro-methyl)benzene-sulfonyl chloride | 70% (0.184 mmol) | $R_t$ = 3.2 min; m/z = 588.3 [MH]$^+$ | GWI2 |
| 57 | | (1R,3R,5S)-3-(Pyridin-4-yloxy)-8-(3-((S)-pyrrolidin-2-yl)propylsulfonyl)-8-azabicyclo[3.2.1]octane dihydrochloride | Naphthalene-2-sulfonyl chloride | 53% (0.137 mmol) | $R_t$ = 3.7 min; m/z = 570.3 [MH]$^+$ | GWI2 |
| 58 | | (1R,3R,5S)-3-(Pyridin-4-yloxy)-8-(3-((S)-pyrrolidin-2-yl)propylsulfonyl)-8-azabicyclo[3.2.1]octane dihydrochloride | Naphthalene-1-sulfonyl chloride | 63% (0.165 mmol) | $R_t$ = 3.5 min; m/z = 570.3 [MH]$^+$ | GWI2 |
| 59 | | (1R,3R,5S)-3-(Pyridin-4-yloxy)-8-(3-((S)-pyrrolidin-2-yl)propylsulfonyl)-8-azabicyclo[3.2.1]octane dihydrochloride | 2,4-Dichloro-benzene-1-sulfonyl chloride | 70% (0.183 mmol) | $R_t$ = 3.7 min; m/z = 588.3 [MH]$^+$ | GWI2 |

-continued

| Example no. | Example compound | Amine dihydrochloride employed | Sulfonyl chloride employed | Yield (%) | Analysis (LC/MS) | Synthesized by/ comments |
|---|---|---|---|---|---|---|
| 60 | | (1R,3R,5S)-3-(Pyridin-4-yloxy)-8-(3-((S)-pyrrolidin-2-yl)propylsulfonyl)-8-azabicyclo[3.2.1]octane dihydrochloride | 2,3-Dichloro-benzene-1-sulfonyl chloride | 60% (0.156 mmol) | $R_t$ = 3.6 min; m/z = 588.3 [MH]$^+$ | GWI2 |
| 61 | | (1R,3R,5S)-3-(Pyridin-4-yloxy)-8-(3-((S)-pyrrolidin-2-yl)propylsulfonyl)-8-azabicyclo[3.2.1]octane dihydrochloride | 4-Chloro-2,5-Dimethyl-benzene-sulfonyl chloride | 58% (0.151 mmol) | $R_t$ = 3.9 min; m/z = 582.3 [MH]$^+$ | GWI2 |
| 69 | | (S)-4-(1-(3-(Pyrrolidin-2-yl)propyl-sulfonyl)piperidin-4-yloxy)pyridine dihydrochloride | 2,2-Dimethyl-chroman-6-sulfonyl chloride | 62% (0.159 mmol) | $R_t$ = 3.7 min; m/z = 578.3 [MH]$^+$ | GWI2 |
| 70 | | (S)-4-(1-(3-(Pyrrolidin-2-yl)propyl-sulfonyl)piperidin-4-yloxy)pyridine dihydrochloride | (3-Chloro-phenyl)-methane-sulfonyl chloride | 34% (0.087 mmol) | $R_t$ = 3.2 min; m/z = 542.2 [MH]$^+$ | GWI2 |
| 71 | | (S)-4-(1-(3-(Pyrrolidin-2-yl)propyl-sulfonyl)piperidin-4-yloxy)pyridine dihydrochloride | 2-Chloro-4-(trifluoro-methyl)benzene-sulfonyl chloride | 61% (0.158 mmol) | $R_t$ = 3.6 min; m/z = 596.2 [MH]$^+$ | GWI2 |
| 72 | | (S)-4-(1-(3-(Pyrrolidin-2-yl)propyl-sulfonyl)piperidin-4-yloxy)pyridine dihydrochloride | 2,6-Dichloro-4-(trifluoro-methyl)benzene-sulfonyl chloride | 70% (0.179 mmol) | $R_t$ = 3.8 min; m/z = 630.2 [MH]$^+$ | GWI2 |
| 73 | | (S)-4-(1-(3-(Pyrrolidin-2-yl)propyl-sulfonyl)piperidin-4-yloxy)pyridine dihydrochloride | 4-Fluoro-2,6-dimethyl-benzene-1-sulfonyl chloride | 52% (0.133 mmol) | $R_t$ = 3.4 min; m/z = 540.3 [MH]$^+$ | GWI2 |

(a) Working up: The reaction mixture was concentrated in vacuo, and three time the residue was taken up in methylene chloride (5 ml) and toluene (2 ml) and the mixture concentrated in vacuo. The residue was taken up in saturated sodium bicarbonate solution (10 ml) and the mixture was extracted three times with methylene chloride (20 ml), and the combined organic phases were dried over magnesium sulfate and concentrated in vacuo.

Example 26

1-(3-(1-(4-Methoxy-2,6-dimethylphenylsulfonyl)
piperidin-2-yl)propylsulfonyl)-4-(1-methylpiperidin-
4-yl)piperazine

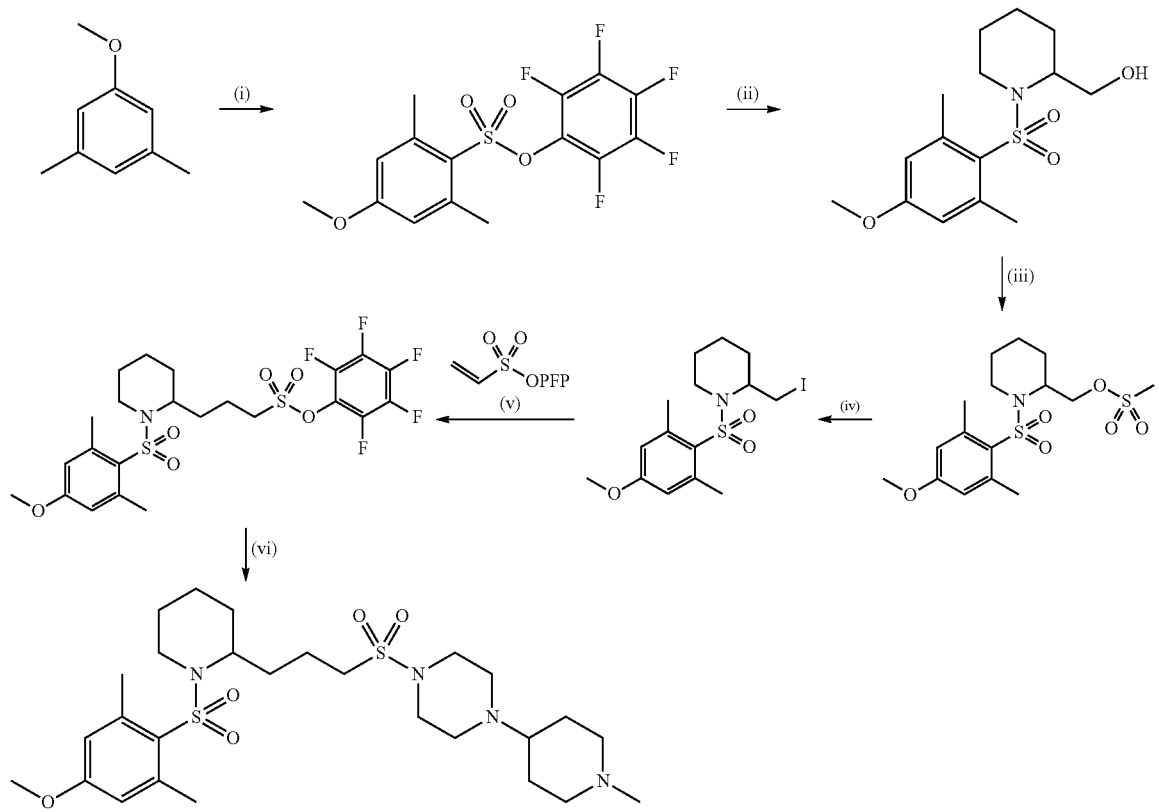

Stage (i): Perfluorophenyl
4-methoxy-2,6-dimethylbenzenesulfonate 3,5-Dimethylanisole (3 g, 22.026 mmol) was initially introduced into methylene chloride (60 ml) and the mixture was cooled, and a solution of chlorosulfuric acid (7.3 ml, 110.13 mmol) in methylene chloride (60 ml) was slowly added dropwise at 0° C. After stirring in a cooling bath for 10 min, the reaction solution was added dropwise to 300 ml of ice-water, the phases were separated, the aqueous phase was extracted with methylene chloride (60 ml) and the combined organic phases were washed with saturated sodium chloride solution (50 ml), dried over sodium sulfate and concentrated in vacuo. During this operation, pentafluorophenol (4.05 g, 22.026 mmol) was dissolved in methylene chloride (50 ml) and triethylamine (6.1 ml, 44.053 mmol) and the solution was stirred for 30 min. The freshly prepared sulfonyl chloride, concentrated on a rotary evaporator, was dissolved in methylene chloride (50 ml) and the solution was slowly added dropwise. After the mixture had been stirred at room temperature for 1 h, saturated sodium bicarbonate solution (40 ml) was added, the phases were separated and the organic phase was washed with saturated sodium chloride solution (40 ml), dried over sodium sulfate and concentrated in vacuo. The crude product was purified by column chromatography (silica gel) with hexane/diethyl ether/methylene chloride (20:1:2). Yield: 6.06 g (71%)

Stage (ii): (1-(4-Methoxy-2,6-dimethylphenylsulfo-
nyl)piperidin-2-yl)methanol

Perfluorophenyl 4-methoxy-2,6-dimethylbenzenesulfonate (1 g, 2.616 mmol), 2-(hydroxymethyl)-piperidine (1.61 g, 13.079 mmol) and tetrabutylammonium chloride (1.45 g, 5.231 mmol) were dissolved in N,N-dimethylformamide (10 ml) and the solution was stirred at 110° C. for 1 h. The solvent was removed in vacuo, the residue was dissolved in ethyl acetate and the solution was washed with ammonium chloride solution (10%, 20 ml), dried over sodium sulfate and concentrated in vacuo. The crude product was purified by column chromatography (silica gel) with diethyl ether/hexane/methylene chloride (1:1:1). Yield: 0.63 g (76%)

Stage (iii): (1-(4-Methoxy-2,6-dimethylphenylsulfo-
nyl)piperidin-2-yl)methyl methanesulfonate Sodium hydride (0.346 g, 8.679 mmol, 60%), washed with hexane and dried with an inert gas, was initially introduced into N,N-dimethylformamide (10 ml) under an inert gas, (1-(4-methoxy-2,6-dimethylphenylsulfonyl)piperidin-2-yl) methanol (1.36 g, 4.34 mmol) was added and the mixture was then stirred at room temperature for 30 min. Triethylamine (1.8 ml, 13.019 mmol) was added, the reaction mixture was cooled with ice-water, and methanesulfonyl chloride (0.838 ml, 10.849 mmol) in N,N-dimethylformamide (10 ml) was slowly added dropwise. After stirring at room temperature for 1 h, 5 ml of water were added and the solvent was removed in vacuo. The residue was taken up in saturated sodium bicarbonate solution (20 ml) and ethyl acetate (50 ml), the phases were separated and the aqueous phase was extracted with ethyl acetate (2×50 ml). The combined organic phases were washed with saturated sodium chloride solution (40 ml), dried over sodium sulfate and concentrated in vacuo. The crude product was purified by column chromatography (silica gel) with diethyl ether/hexane/methylene chloride (1:1:1). Yield: 1.66 g (97%)

Stage (iv): 2-(Iodomethyl)-1-(4-methoxy-2,6-dimethylphenylsulfonyl)piperidine (1-(4-Methoxy-2,6-dimethylphenylsulfonyl)piperidin-2-yl)methyl methanesulfonate (0.25 g, 0.639 mmol) and sodium iodide (0.383 g, 2.554 mmol) were dissolved in acetone (7 ml) and the solution was heated at 120° C. in a microwave oven (CEM Discover; 100 watt) for 1 h. The solvent was removed in vacuo, the residue was dissolved in sodium thiosulfate solution (20 ml, 5 mmol/l) and diethyl ether (40 ml), the phases were separated and the aqueous phase was extracted with diethyl ether (2×20 ml). The combined organic phases were dried over sodium sulfate and concentrated in vacuo. The crude product was purified by column chromatography (silica gel) with hexane/diethyl ether/methylene chloride (3:1:1). Yield: 0.2 g (74%)

Stage (v): Perfluorophenyl 3-(1-(4-methoxy-2,6-dimethylphenylsulfonyl)piperidin-2-yl)propane-1-sulfonate 1-Ethylpiperidine hypophosphite (1.184 g, 6.614 mmol) were weighed into the reaction flask under an inert gas, and methylene chloride (10 ml) was added. The solution was cooled with ice-water, and 2,3,4,5,6-pentafluorophenyl 1-ethylenesulfonate (0.218 g, 0.794 mmol) [Org. Lett.; 2002; 4(15); 2549-2551] and 2-(iodomethyl)-1-(4-methoxy-2,6-dimethylphenylsulfonyl)piperidine (0.28 g, 0.661 mmol) was added at 0° C. Triethylborane solution (0.03 ml, 1 mol/l) was added to the reaction mixture and compressed air was then passed through the mixture for 10 sec. After stirring for 5 min the addition of triethylborane solution-compressed air was repeated with the same amount. After thin layer chromatography control, the addition of triethylborane soln.-compressed air was repeated again with the same amount. The reaction mixture was washed with cooled water (10 ml) and cooled saturated sodium bicarbonate soln. (10 ml), dried over sodium sulfate and concentrated in vacuo. The crude product was purified by column chromatography (silica gel) with hexane/diethyl ether/methylene chloride (6:1:1) Yield: 50 mg (13%)

Stage (vi): 1-(3-(1-(4-Methoxy-2,6-dimethylphenylsulfonyl)piperidin-2-yl)propylsulfonyl)-4-(1-methylpiperidin-4-yl)piperazine (Example 26)

Perfluorophenyl 3-(1-(4-methoxy-2,6-dimethylphenylsulfonyl)piperidin-2-yl)propane-1-sulfonate (40 mg, 0.07 mmol) and 1-(1-methyl-4-piperidinyl)piperazine (25 mg, 0.14 mmol) were dissolved in tetrahydrofuran (10 ml), 1,8-diazabicyclo[5.4.0]undec-7-ene (0.03 ml, 0.21 mmol) was added under an inert gas and the mixture was refluxed for 1 h and stirred at room temperature for 15 h. Methylene chloride and saturated sodium bicarbonate solution (10 ml of each) were added, the phases were separated and the aqueous phases were extracted with methylene chloride (20 ml). The combined organic phases were dried over sodium sulfate and concentrated in vacuo. The crude product was purified by column chromatography (silica gel) with ethyl acetate/methanol/ammonia (25 aq) (200:100:1). Yield: 18 mg (45%). MS, m/z=571.3 [MH]$^+$ Example 39

1-(4-Methoxy-2,3,6-trimethylphenylsulfonyl)-3-(2-(4-(2-(pyrrolidin-1-yl)ethyl)piperidin-1-ylsulfonyl)ethyl)piperidine

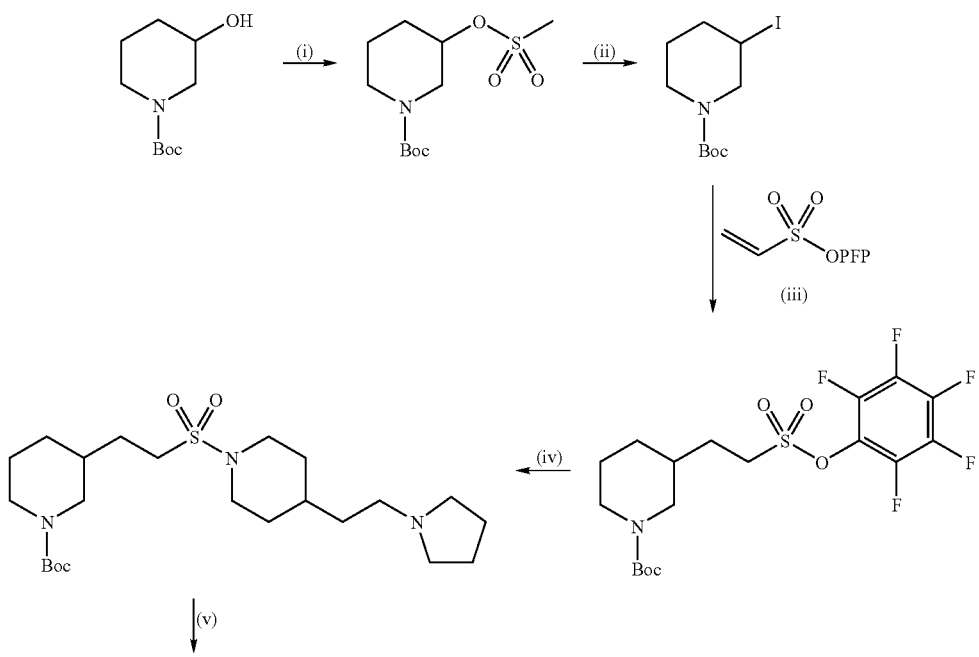

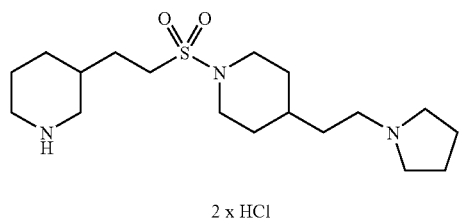

2 x HCl (vi) →

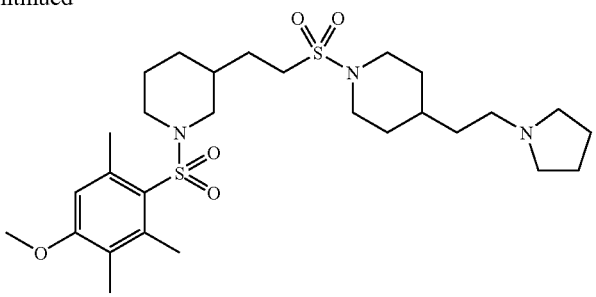

Stage (i): tert-Butyl 3-(methylsulfonyloxy)piperidine-1-carboxylate

1-Boc-3-hydroxypiperidine (0.5 g, 2.49 mmol) was dissolved in tetrahydrofuran (5 ml), triethylamine (0.75 g, 7.46 mmol) was added and the mixture was cooled. Methanesulfonic acid chloride (0.23 ml, 3 mmol) was added, the mixture was stirred in an ice bath for 10 min, saturated sodium bicarbonate solution (10 ml) was then added, as well as ethyl acetate (10 ml). Phase separation, the aqueous phase was extracted with ethyl acetate (2×20 ml) and the combined organic phases were washed with saturated sodium chloride solution (20 ml), dried over sodium sulfate and concentrated in vacuo. Yield: 0.54 g (77%)

Stage (ii): tert-Butyl 3-iodopiperidine-1-carboxylate tert-Butyl 3-(methylsulfonyloxy)piperidine-1-carboxylate (0.54 g, 1.94 mmol) and sodium iodide (0.87 g, 5.8 mmol) were dissolved in acetone (10 ml) and the solution was refluxed under an inert gas for 6 h and then stirred at room temperature for 15 h. After thin layer chromatography control, the reaction mixture was heated in three portions in a microwave oven (CEM Discover): 10 min 100° C. 150 watt, 15 min 150° C. 200 watt, 20 min 100° C. 150 watt. After thin layer chromatography control, the three portions were combined, sodium thiosulfate solution (20 ml, 5 mmol/l) was added, the phases were separated and the aqueous phase was extracted with ethyl acetate (2×20 ml). The combined organic phases were washed with saturated sodium chloride solution (10 ml), dried over sodium sulfate and concentrated in vacuo. The crude product was purified by column chromatography (silica gel) with hexane/diethyl ether (3:1). Yield: 0.14 g (23%)

Stage (iii): tert-Butyl 3-(2-(perfluorophenoxysulfonyl)ethyl)piperidine-1-carboxylate 1-Ethylpiperidine hypophosphite (7.49 g, 41.8 mmol) were weighed into the reaction flask under an inert gas, and methylene chloride (38 ml) was added. The solution was cooled with ice-water, and 2,3,4,5,6-pentafluorophenyl 1-ethylenesulfonate (1.38 g, 5.02 mmol) [Org. Lett.; 2002; 4(15); 2549-2551] and tert-butyl 3-iodopiperidine-1-carboxylate (1.3 g, 4.18 mmol) was added at 0° C. Triethylborane solution (0.21 ml, 1 mol/l) was added to the reaction mixture and compressed air was then passed through the mixture for 10 sec. After stirring for 5 min the addition of triethylborane solution-compressed air was repeated with the same amount. Stir for 5 min, the addition of triethylborane solution-compressed air was then repeated with the same amount. The reaction mixture was washed with water (20 ml), sodium bicarbonate solution (20 ml, saturated 50% diluted) and saturated sodium chloride solution (20 ml), dried over sodium sulfate and concentrated in vacuo. The crude product was purified by column chromatography (silica gel) with hexane/diethyl ether (3:1). Yield: 0.5 g (26%)

Stage (iv): tert-Butyl 3-(2-(4-(2-(pyrrolidin-1-yl)ethyl)piperidin-1-ylsulfonyl)ethyl)piperidine-1-carboxylate tert-Butyl 3-(2-(perfluorophenoxysulfonyl)ethyl)piperidine-1-carboxylate (0.5 g, 1.09 mmol) and 4-(2-pyrrolidinoethyl)piperidine (0.4 g, 2.18 mmol) were dissolved in tetrahydrofuran (10 ml), 1,8-diazabicyclo[5.4.0]undec-7-ene (0.5 ml, 3.27 mmol) was added under an inert gas and the mixture was refluxed for 2 h. Ethyl acetate and saturated sodium bicarbonate solution (20 ml of each) were added, the phases were separated and the aqueous phase was extracted with ethyl acetate (2×30 ml). The combined organic phases were washed with saturated sodium chloride solution (20 ml), dried over sodium sulfate and concentrated in vacuo. The crude product was purified by column chromatography (silica gel) with ethyl acetate/methanol/ammonia (25% aq) (300:100:1). Yield: 0.32 g (64%)

Stage (v): 1-(2-(Piperidin-3-yl)ethylsulfonyl)-4-(2-(pyrrolidin-1-yl)ethyl)piperidine dihydrochloride tert-Butyl 3-(2-(4-(2-(Pyrrolidin-1-yl)ethyl)piperidin-1-ylsulfonyl)ethyl)piperidine-1-carboxylate (0.26 g, 0.57 mmol) was dissolved in methanol (10 ml), hydrogen chloride in methanol (4.5 ml, 1.25 mol/l) was added and the mixture was refluxed. After 1 h the mixture was concentrated in vacuo, the residue was taken up in ethanol (5 ml) and a precipitate was precipitated out with diethyl ether. The suspension was stirred in an ice bath for 1 h and the precipitate was filtered off with suction, washed with ether and dried in vacuo. Yield: 0.19 g (77%)

Stage (vi): 1-(4-Methoxy-2,3,6-trimethylphenylsulfonyl)-3-(2-(4-(2-(pyrrolidin-1-yl)ethyl)piperidin-1-ylsulfonyl)ethyl)piperidine (Example 39)

1-(2-(Piperidin-3-yl)ethylsulfonyl)-4-(2-(pyrrolidin-1-yl)ethyl)piperidine dihydrochloride (0.15 g, 0.35 mmol) was dissolved in tetrahydrofuran (10 ml) under an inert gas, and triethylamine (0.15 ml, 1.05 mmol) and 4-methoxy-2,3,6-trimethylbenzenesulfonyl chloride (0.1 g, 0.42 mmol) were added. The mixture was refluxed for 2 h, saturated sodium bicarbonate solution (10 ml) was then added and the phases were separated. The aqueous phase was extracted with ethyl acetate (20 ml) and the combined organic phases were washed with saturated sodium chloride solution (20 ml), dried over sodium sulfate and concentrated in vacuo. The crude product was purified by column chromatography (silica gel) with ethyl acetate/methanol/ammonia (25% aq) (300:100:1) and the hydrochloride was precipitated from an ethanol/ethereal solution with 1.2 eq of trimethylchlorosilane. Yield: 0.15 g (70%). MS, m/z=570.3 [MH]$^+$

Example 37

1-(1-Methylpiperidin-4-yl)-4-((1-(3-(trifluoromethyl)phenylsulfonyl)piperidin-2-yl)methylsulfonyl)piperazine

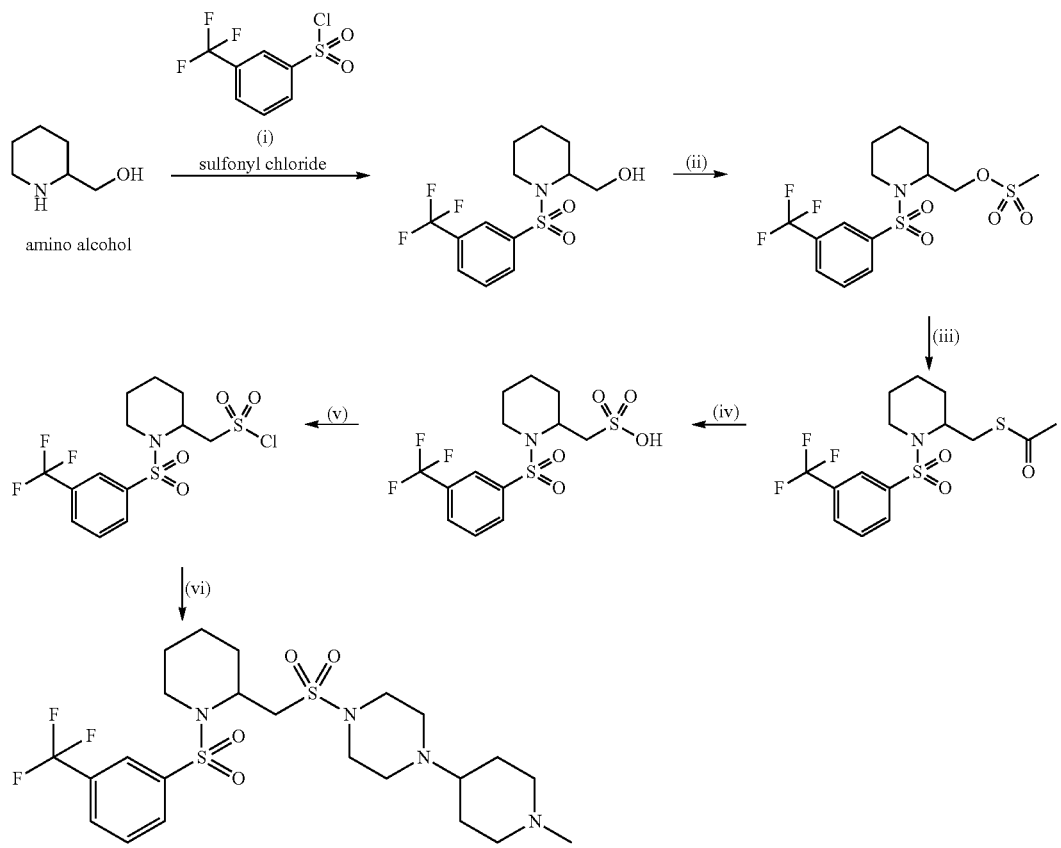

Stage (i): (1-(3-(Trifluoromethyl)phenylsulfonyl)piperidin-2-yl)methanol 3-(Trifluoromethyl)benzenesulfonic acid chloride (1 eq), dissolved in methylene chloride (65 ml), was added dropwise to a cooled solution (0° C.) of 2-piperidinemethanol (40 mmol, 1.1 eq) in methylene chloride (160 ml) and triethylamine (2.5 eq). When the addition was complete, the cooling bath was removed and the reaction mixture was stirred at room temperature until, according to thin layer chromatography control, the reaction was complete (90 min). Hydrogen chloride solution (0.5 mol/l, 75 ml) was added, the mixture was stirred for 15 min, the phases were separated and the organic phase was washed with water, dried over sodium sulfate and concentrated in vacuo. Yield: 28%

Stage (ii): (1-(3-(Trifluoromethyl)phenylsulfonyl)piperidin-2-yl)methyl methanesulfonate Methanesulfonyl chloride (1 eq), dissolved in methylene chloride (2 ml/mmol) was added dropwise to a cooled solution (0° C.) of (1-(3-(trifluoromethyl)phenyl-sulfonyl)piperidin-2-yl)methanol (1.1 eq) in methylene chloride (4 ml/mmol) and triethylamine (2.5 eq). When the addition was complete, the cooling bath was removed and the reaction mixture was stirred at room temperature until, according to thin layer chromatography control, the reaction was complete. Hydrogen chloride solution (0.5 mol/l, 2 ml/mmol) was added, the mixture was stirred for 15 min, the phases were separated and the organic phase was washed with water, dried over sodium sulfate and concentrated in vacuo. Yield: 43%

Stage (iii): S-(1-(3-(Trifluoromethyl)phenylsulfonyl)piperidin-2-yl)methyl ethanethioate (1-(3-(Trifluoromethyl)phenylsulfonyppiperidin-2-yl)methyl methanesulfonate (0.24 g, 0.598 mmol) was dissolved in N,N-dimethylformamide (dry, 1 ml), and tetrabutylammonium bromide (19 mg, 0.059 mmol) and potassium thioacetate (103 mg, 0.897 mmol) were added. The reaction mixture was heated to 50° C. and stirred at this temperature for 16 h. After cooling to room temperature, hydrolysis was carried out with water and the mixture was extracted with ethyl acetate (3×50 ml). The combined organic phases were washed with water and saturated sodium chloride solution, dried over sodium sulfate and concentrated in vacuo. The crude product was purified by column chromatography (silica gel) with hexane/ethyl acetate (9:1). Yield: 40%

Stage (iv): (1-(3-(Trifluoromethyl)phenylsulfonyl) piperidin-2-yl)methanesulfonic acid S-(1-(3-(Trifluoromethyl)phenylsulfonyl)piperidin-2-yl) methyl ethanethioate (0.1 g, 0.263 mmol) was dissolved in methylene chloride (1 ml) and water (0.1 ml), the solution was cooled and chlorine gas was passed in until the reaction mixture became yellow in color. In order to remove excess chlorine gas, the reaction mixture was flushed with argon, then diluted with methylene chloride and washed with water and saturated sodium chloride solution. It was dried over sodium sulfate and concentrated in vacuo. The crude product was employed in the next stage without purification.

Stage (v): (1-(3-(Trifluoromethyl)phenylsulfonyl) piperidin-2-yl)methanesulfonyl chloride (1-(3-(Trifluoromethyl)phenylsulfonyl)piperidin-2-yl) methanesulfonic acid was dissolved in benzene (3 ml), thionyl chloride (0.034 ml) was added and the mixture was refluxed for 4 h. After cooling, the reaction mixture was concentrated in vacuo and the crude product was employed in the next stage without purification.

Stage (vi): 1-(1-Methylpiperidin-4-yl)-4-((1-(3-(trifluoromethyl)phenylsulfonyl)piperidin-2-yl)methylsulfonyl)piperazine (Example 37)

1-(1-Methyl-4-piperidinyl)piperazine (1.126 mmol) was dissolved in methylene chloride (7 ml), the solution was cooled in an ice bath and triethylamine (2.8 mmol) and (1-(3-(trifluoromethyl)phenylsulfonyl)piperidin-2-yl)methanesulfonic acid chloride (dissolved in methylene chloride (3 ml)) were added. The mixture was stirred for 16 h, during which it was allowed to warm slowly to room temperature. The reaction mixture was diluted with methylene chloride and washed with water and the organic phase was dried over sodium sulfate and concentrated in vacuo. The crude product was purified by column chromatography (silica gel) with methylene chloride/methanol (19:1). Yield: 30%. MS, $R_t$=2.4 min, m/z=553.0 [MH]$^+$ The example compound listed in the following table was prepared from the corresponding educts closely in accordance with the process described for Example 37.

In Example 38, after the column chromatography (after stage (vi)), a hydrochloride was precipitated from a 1,4-dioxane solution with hydrogen chloride in 1,4-dioxane.

| Example no. | Example compound product-stage (vi) | Amino alcohol employed in stage (I) | Sulfonyl chloride employed in stage (I) | Yield (%) [stage (vi)] | MS, m/z (MH$^+$) |
|---|---|---|---|---|---|
| 38 | 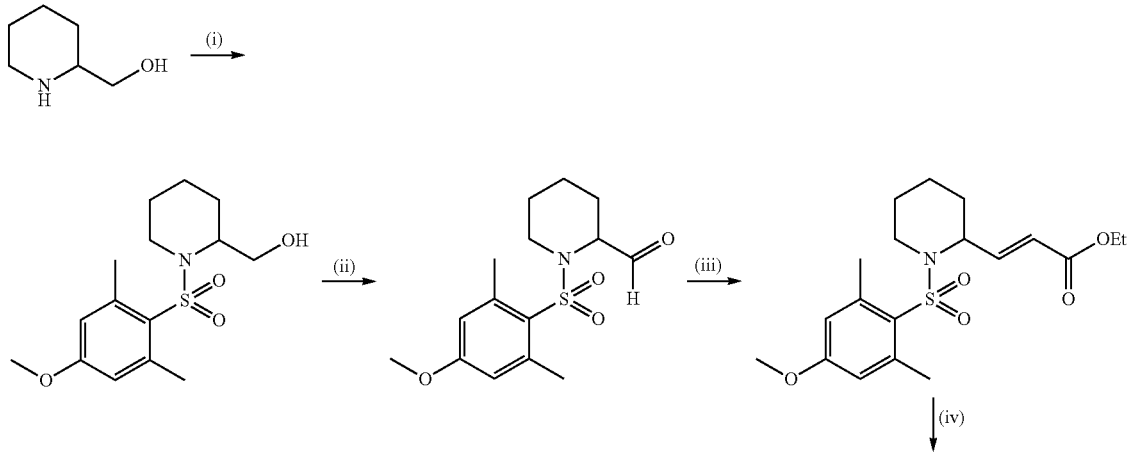 | 2-(Piperidin-2-yl)ethanol | 4-Chloro-2,5-dimethylbenzenesulfonyl chloride | 18 | $R_t$ = 2.8 min; m/z = 561.1 [MH]$^+$ |

Example 74

3-(3-(1-(4-Methoxy-2,6-dimethylphenylsulfonyl) piperidin-2-yl)propylsulfonyl)-9-(pyridin-4-yl)-3,9-diazaspiro[5.5]undecane

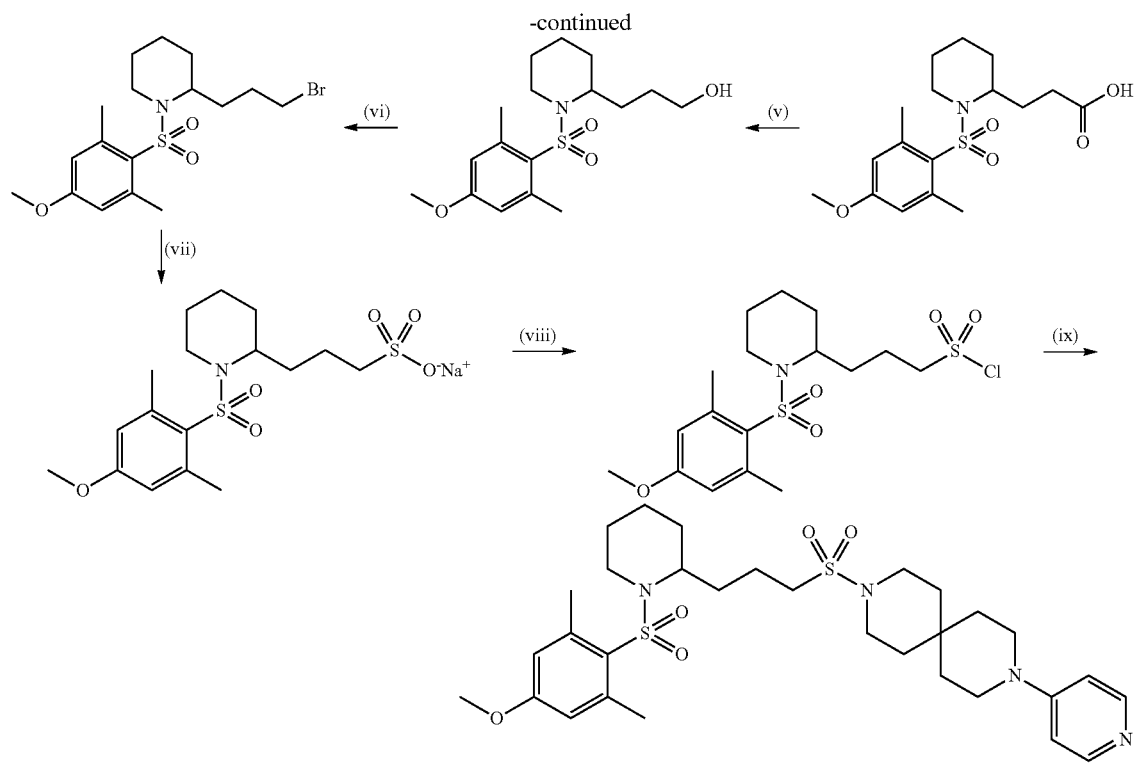

Stage (i): (1-(4-Methoxy-2,6-dimethylphenylsulfonyl)piperidin-2-yl)methanol

A solution of triethylamine (2.5 eq) and 4-methoxy-2,6-dimethylbenzenesulfonyl chloride (13.04 mmol, 1 eq) in MC (10 ml) was added dropwise to a solution of piperidin-2-ylmethanol (13.04 mmol) in MC (30 ml) at 0° C. and the mixture was stirred at 0° C. for 30 min. It was then stirred at room temperature for 14 h, MC (50 ml) was subsequently added to the mixture and the mixture was washed with water and sat. sodium chloride solution. The organic phase was dried (Na$_2$SO$_4$) and concentrated in vacuo. The crude product obtained in this way was purified by column chromatography. Yield: 3.2 g (79%)

Stage (ii): (1-(4-Hydroxy-2,6-dimethylphenylsulfonyl)piperidine-2-carbaldehyde 1-(4-Methoxy-2,6-dimethylphenylsulfonyl)piperidin-2-yl)methanol (6.39 mmol) was converted into the corresponding aldehyde (crude yield 2.1 g—employed in the following stage without further purification) under standard Swern oxidation conditions.

Stage (iii): (E)-Ethyl 3-(1-(4-methoxy-2,6-dimethylphenylsulfonyl)piperidin-2-yl)acrylate A solution of Wittig salt (6.95 mmol, 1.2 eq) in THF (20 ml) was added to a suspension of sodium hydride (6.95 mmol, 1.2 eq) in THF (20 ml) at 0° C. and the mixture was stirred for 30 min. A solution of 1-(4-hydroxy-2,6-dimethylphenyl-sulfonyl)piperidine-2-carbaldehyde (5.79 mmol) in THF (10 ml) was subsequently added and the mixture was stirred for a further 30 min. The reaction mixture was then warmed to room temperature and stirred for 12 h. Water was added and the mixture was diluted with ethyl acetate and washed with water and sat. sodium chloride solution. The organic phase was dried (Na$_2$SO$_4$) and concentrated in vacuo. The resulting crude product was purified by column chromatography (silica gel). Yield: 72.5%

Stage (iv): Ethyl 3-(1-(4-methoxy-2,6-dimethylphenylsulfonyl)piperidin-2-yl)propanoate A degassed solution of (E)-ethyl 3-(1-(4-methoxy-2,6-dimethylphenylsulfonyl)-piperidin-2-yl)acrylate (4.19 mmol) in MeOH was hydrogenolysed with Pd(OH)$_2$ (0.4 g) as the catalyst. The resulting crude product was employed in the following stage without further purification.

Stage (v): 3-(1-(4-Methoxy-2,6-dimethylphenylsulfonyl)piperidin-2-yl)propan-1-ol A solution of ethyl 3-(1-(4-methoxy-2,6-dimethylphenyl-sulfonyl)piperidin-2-yl)propanoate (3.39 mmol. 1 eq) in THF (10 ml) was slowly to a suspension of LAH (7.47 mmol, 2.2 eq) in THF (7.5 ml) at 0° C. and the mixture was stirred for 30 min. The mixture was subsequently warmed to room temperature and stirred for 1 h. A water/THF mixture was then added, the mixture was filtered over Celite and the filtrate was concentrated in vacuo. The crude product (0.88 g) was employed in the following stage without further purification.

Stage (vi): 2-(3-Bromopropyl)-1-(4-methoxy-2,6-dimethylphenylsulfonyl)piperidine PBr$_3$ (2.64 mmol, 1.5 eq) was added to a solution of 3-(1-(4-methoxy-2,6-dimethylphenylsulfonyl)piperidin-2-yl)propan-1-ol (1.76 mmol, 1 eq) in DMF (6 ml) at 0° C. and the mixture was stirred for 30 min. Water (20 ml) was subsequently added and the mixture was extracted with ethyl acetate. The organic phase was washed with water and sat.

sodium chloride solution, dried (Na$_2$SO$_4$) and concentrated in vacuo. The crude product obtained in this way was purified by column chromatography (silica gel). Yield: 25%

Stage (vii) & (viii): 3-(1-(4-Methoxy-2,6-dimethylphenylsulfonyl)piperidin-2-yl)propane-1-sulfonyl chloride (vii) A solution of Na$_2$SO$_4$ (0.53 mmol, 1.2 eq) in water (4 ml) was added to 2-(3-bromopropyl)-1-(4-methoxy-2,6-dimethylphenylsulfonyl)piperidine (0.45 mmol, 1 eq) in EtOH (4 ml) and the resulting mixture was refluxed for 4 h and then concentrated in vacuo.

(viii) The residue was taken up in toluene (6 ml) and SO$_2$Cl$_2$ (3 ml) was added. The mixture was then refluxed for 3 h and subsequently concentrated in vacuo. The crude product was used in the following stage without further purification.

Stage (ix): 3-(3-(1-(4-Methoxy-2,6-dimethylphenylsulfonyl)piperidin-2-yl)-propylsulfonyl)-9-(pyridin-4-yl)-3,9-diazaspiro[5.5]undecane (Example 74)

3-(1-(4-Methoxy-2,6-dimethylphenylsulfonyl)piperidin-2-yl)propane-1-sulfonyl chloride (1.3 mmol, 1 eq) in MC (5 ml) was added to a solution of 3-(pyridin-4-yl)-3,9-diazaspiro[5.5]undecane (1.56 mmol, 1.2 eq) and DIPEA (5.2 eq) at 0° C. and the mixture was stirred for 30 min. The reaction mixture was subsequently warmed to room temperature and stirred for 12 h. The reaction mixture was diluted with methylene chloride and washed with water and sat. sodium chloride solution. The organic phase was dried (Na$_2$SO$_4$) and concentrated in vacuo. The crude product obtained in this way was purified by column chromatography (silica gel). Yield: 0.4 g (50%). MS, R$_t$=3.8 min, m/z=614.9 [MH]$^+$.

Example 86

3-(3-(1-(2-Chloro-6-methylphenylsulfonyl)piperidin-2-yl)propylsulfonyl)-9-(pyridin-4-yl)-3,9-diazaspiro[5.5]undecane

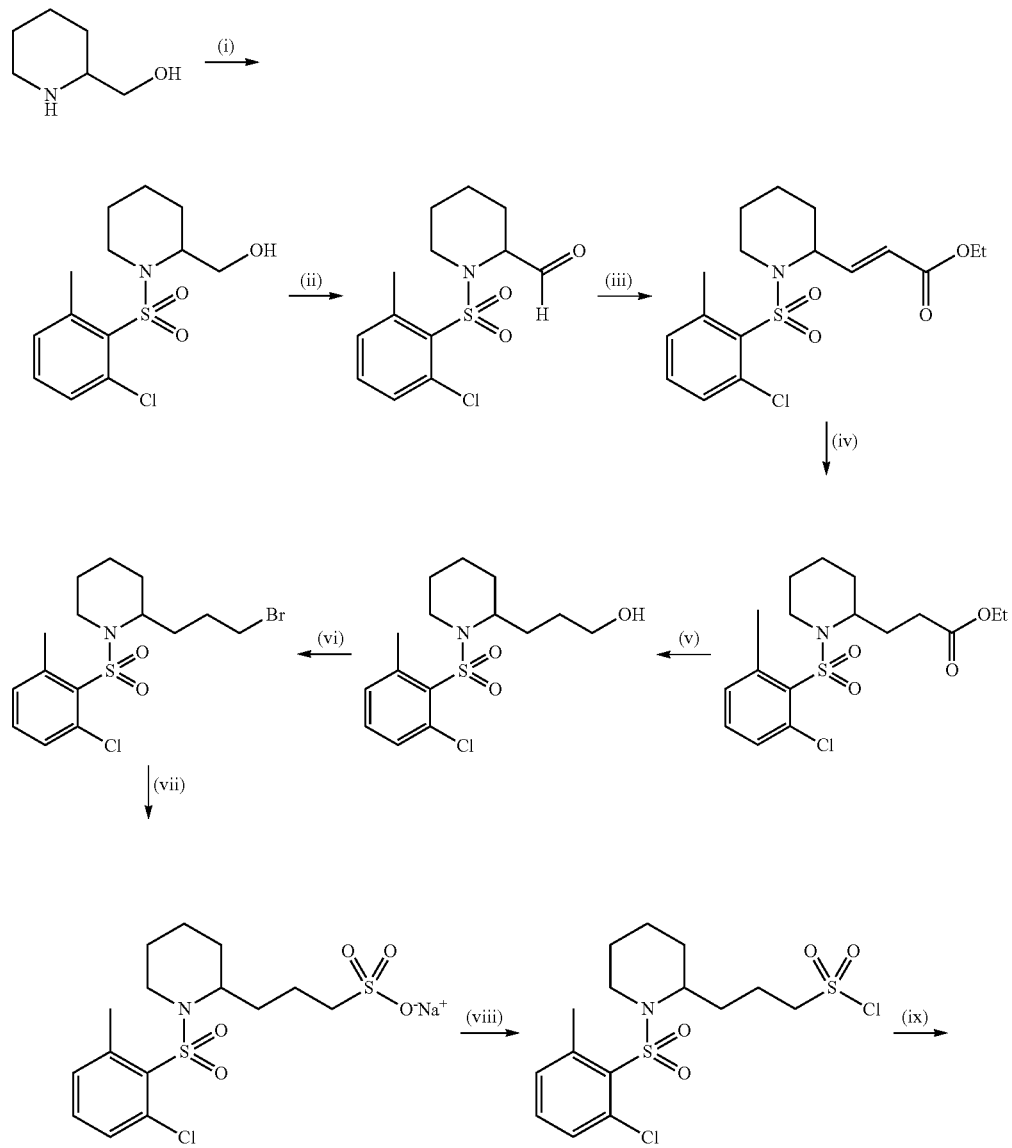

-continued

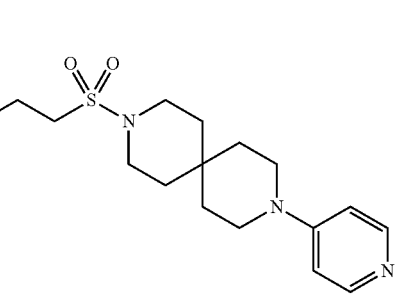

Stage (i): (1-(2-Chloro-6-methylphenylsulfonyl)piperidin-2-yl)methanol

Piperidin-2-yl-methanol (17.39 mmol, 1 eq) was dissolved in methylene chloride (20 ml) and triethylamine (43.47 mmol, 2.5 eq) at 0° C. and a solution of 2-chloro-6-methylbenzenesulfonyl chloride (17.39 mmol, 1 eq) in methylene chloride (65 ml) was added dropwise. The reaction solution was stirred at room temperature for 90 min. 0.5 M HCl (75 ml) was then added and the mixture was stirred for a further 15 min. The organic phase was washed with water (10 ml), dried over sodium sulfate and concentrated to dryness under reduced pressure. Yield: 90%

Stage (ii): 1-(2-Chloro-6-methylphenylsulfonyl)piperidine-2-carbaldehyde

Oxalyl chloride (3.3 mmol, 2 eq.) was dissolved in methylene chloride and DMSO (4 eq) was added under argon at −78° C. and the reaction mixture was then stirred at this temperature for 15 min. (1-(2-Chloro-6-methylphenylsulfonyl)-piperidin-2-yl)methanol (1.65 mmol) was dissolved in methylene chloride (15 ml) and the solution was added dropwise to the reaction solution at −78° C. The resulting mixture was stirred for 1 h. Triethylamine (8.25 mmol, 5 eq) was then added and the reaction solution was warmed to room temperature and stirred for 1 h. It was then diluted with methylene chloride (10 ml) and washed with saturated ammonium chloride solution (10 ml), water (2×20 ml) and saturated sodium chloride solution (10 ml). The organic phase was dried over sodium sulfate and the filtrate was concentrated to dryness under reduced pressure. The crude product was employed in the next stage without further purification. Yield: 80%

Stage (iii): (E)-Ethyl 3-(1-(2-chloro-6-methylphenylsulfonyl)piperidin-2-yl)acrylate NaH (60% strength, 60 mg) was suspended in THF (5 ml) at 0° C., triethyl phosphonoacetate (1.29 mmol, 1.3 eq) in THF (2 ml) was then added and the mixture was stirred at room temperature for 30 min. The reaction mixture was cooled again to 0° C. and 1-(2-chloro-6-methylphenylsulfonyl)piperidine-2-carbaldehyde (0.99 mmol, 1 eq) in THF (2 ml) was added dropwise. The resulting reaction mixture was stirred at room temperature for 16 h. The reaction was hydrolysed with an ice-cold sodium chloride solution (2 ml) and the mixture was extracted with ethyl acetate. The organic phase was washed with water (10 ml) and saturated sodium chloride solution (2×15 ml), dried over sodium sulfate and concentrated. The crude product was purified by column chromatography (50% ethyl acetate in hexane). Yield: 59%

Stage (iv): Ethyl 3-(1-(2-chloro-6-methylphenylsulfonyl)piperidin-2-yl)propanoate (E)-Ethyl 3-(1-(2-chloro-6-methylphenylsulfonyl)piperidin-2-ypacrylate (1 g) was dissolved in methanol (25 ml), the mixture was degassed with argon and 10% Pd/C (500 mg) was then added. The resulting reaction mixture was hydrogenated under normal pressure for 1 h. After thin layer chromatography control, the reaction mixture was filtered over Celite and the residue was washed with methanol. The filtrate was concentrated to dryness under reduced pressure. Yield: 90%

Stage (v): 3-(1-(2-Chloro-6-methylphenylsulfonyl)piperidin-2-yl)propan-1-01

LAH (5.36 mmol, 2 eq) was initially introduced into THF (10 ml) at 0° C., a solution of ethyl 3-(1-(2-chloro-6-methylphenylsulfonyl)piperidin-2-yl)propanoate (5.36 mmol, 2 eq) in THF (10 ml) was slowly added and the mixture was then stirred at room temperature for 1 h. The reaction was hydrolysed with THF/water (1:1), the mixture was filtered over Celite and the filtrated was concentrated to dryness under reduced pressure.

Stage (vi): 2-(3-Bromopropyl)-1-(2-chloro-6-methylphenylsulfonyl)-piperidine $PBr_3$ (3.8 mmol, 1.5 eq) was added dropwise to a solution of 3-(1-(2-chloro-6-methylphenylsulfonyl)piperidin-2-yl)propan-1-ol (2.53 mmol, 1 eq) in DMF (6 ml) at 0° C. and the mixture was stirred for 30 min. The reaction mixture was diluted with water (20 ml) and extracted with ethyl acetate (2×20 ml). The combined organic phases were washed with water (30 ml) and saturated sodium chloride solution (20 ml), dried over sodium sulfate and concentrated. The crude product was purified by column chromatography (30% ethyl acetate in hexane). Yield: 25%

Stage (vii) & (viii): 3-(1-(2-Chloro-6-methylphenylsulfonyl)piperidin-2-yl)propane-1-sulfonyl chloride 2-(3-Bromopropyl)-1-(2-chloro-6-methylphenylsulfonyl)piperidine (0.93 mmol, 1 eq) was dissolved in ethanol (8 ml), a solution of $Na_2SO_3$ (1.16 mmol) in water (4 ml) was added and the mixture was heated at the boiling temperature for 4 h. The reaction mixture was then reduced to dryness, the residue was taken up in toluene (15 ml) and $SO_2Cl_2$ (6 ml) was added. The resulting reaction mixture was heated under reflux for 3 h and was then concentrated to dryness. The crude product was employed in the next stage without further purification. Yield: 40%

Stage (ix): 3-(3-(1-(2-Chloro-6-methylphenylsulfonyl)piperidin-2-yl)propylsulfonyl)-9-(pyridin-4-yl)-3,9-diazaspiro[5.5]undecane 3-(1-(2-Chloro-6-methylphenylsulfonyl)piperidin-2-yl)propane-1-sulfonyl chloride (0.43 mmol, 1 eq) was dissolved in methylene chloride (5 ml) and a solution of 3-(pyridin-4-yl)-3,9-diazaspiro[5.5]undecane (0.43 mmol, 1 eq) and DIPEA (2.15 mmol, 5 eq) in methylene chloride was added at 0° C. The resulting mixture was stirred for 30 min and then warmed to room temperature and stirred for a further 12 h. It was then diluted with methylene chloride (20 ml) and the organic phase was washed with water (10 ml) and saturated sodium chloride solution (10 ml), dried over sodium sulfate and concentrated. The crude product was purified by column chromatography (10% methanol in methylene chloride). Yield: 50%. MS, $R_t$=3.9 min, m/z=609.3 [MH]$^+$.

Example 87

3-(3-(1-(4-Methoxy-2,6-dimethylphenylsulfonyl) piperidin-2-yl)propylsulfonyl)-9-(pyridin-3-yl)-9-(2-(pyrrolidin-1-yl)ethoxy)-3-azaspiro[5.5]undecane Stage (i): (1-(4-Methoxy-2,6-dimethylphenylsulfonyl)piperidin-2-yl)methanol Piperidin-2-yl-methanol (60.77 mmol, 1 eq) was dissolved in methylene chloride (150 ml) and triethylamine (151.92 mmol, 2.5 eq) at 0° C. and a solution of 4-methoxy-2,6-dimethyl-benzenesulfonyl chloride (60.77 mmol, 1 eq) in methylene chloride (50 ml) was added dropwise at 0° C. The reaction solution was stirred at room temperature for 14 h. The reaction solution was then diluted with methylene chloride (200 ml) and the organic phase was washed with saturated sodium chloride solution (2×50 ml), dried over sodium sulfate and concentrated. The crude product was purified by column chromatography (5-20% ethyl acetate in hexane). Yield: 63%

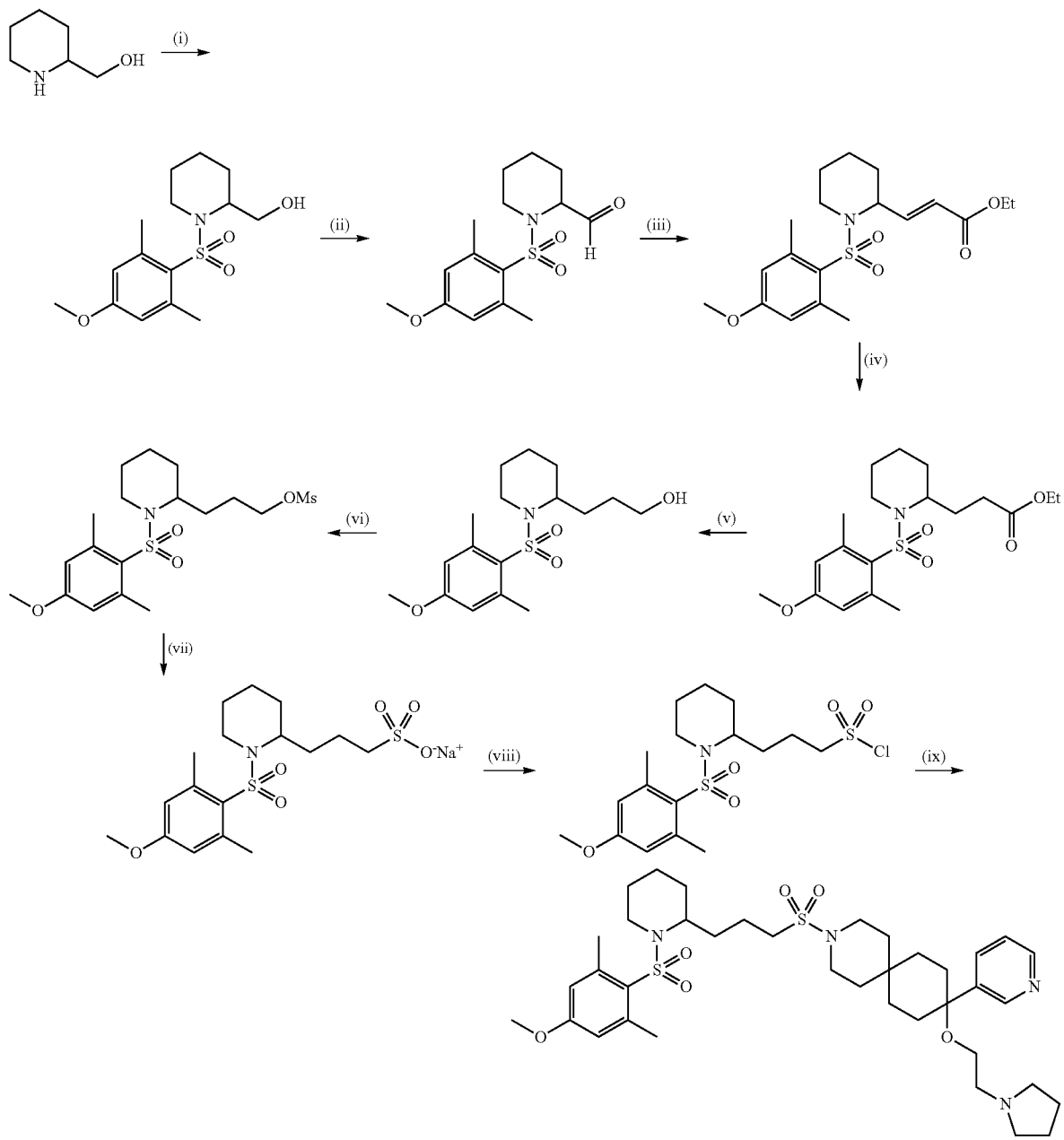

Stage (ii): 1-(4-Methoxy-2,6-dimethylphenylsulfonyl)piperidine-2-carbaldehyde DMSO (12.76 mmol, 4 eq.) was dissolved in methylene chloride (10 ml), oxalyl chloride (6.38 mmol, 2 eq) was added under nitrogen at −78° C. and the mixture was then stirred at this temperature for 30 min. (1-(4-Methoxy-2,6-dimethylphenylsulfonyl)piperidin-2-yl)methanol (3.1 mmol, 1 eq) was dissolved in methylene chloride (10 ml), the solution was added dropwise to the reaction solution at −78° C. and this was then stirred for 30 min. Triethylamine (12.76 mmol, 5 eq) was added and the reaction solution was warmed to room temperature and stirred for 1 h. Water (20 ml) was added to the reaction mixture and the mixture was extracted with methylene chloride (3×60 ml). The organic phase was dried over sodium sulfate and filtered and the filtrate was concentrated to dryness under reduced pressure. The crude product was employed in the next stage without further purification. Yield: 90%

Stage (iii): (E)-Ethyl 3-(1-(4-methoxy-2,6-dimethylphenylsulfonyl)piperidin-2-yl)acrylate A solution of triethyl phosphonoacetate (3.8 mmol, 1.2 eq) in THF (12 ml) was added dropwise to a suspension of NaH (3.8 mmol, 1.2 eq) in THF (12 ml) at 0° C. and the mixture was stirred for 30 min. 1-(4-Methoxy-2,6-dimethylphenylsulfonyl)piperidine-2-carbaldehyde (3.2 mmol) in THF (6 ml) was then added and the mixture was stirred for a further 30 min. The reaction mixture was warmed to room temperature and stirred for 12 h. Hydrolysis was then carried out with water and the mixture was extracted with ethyl acetate. The organic phase was washed with water (20 ml) and saturated sodium chloride solution (20 ml), dried over sodium sulfate and concentrated. The crude product was purified by column chromatography (5-20% ethyl acetate in hexane). Yield: 40%

Stage (iv): Ethyl 3-(1-(4-methoxy-2,6-dimethylphenylsulfonyl)piperidin-2-yl)propanoate (E)-Ethyl 3-(1-(4-methoxy-2,6-dimethylphenylsulfonyl)piperidin-2-yl)acrylate (1.28 mmol) was dissolved in methanol (20 ml), the mixture was degassed with argon and Pd(OH)$_2$ (125 mg) was added. Hydrogenation was then carried out under normal pressure for 4-6 h. After thin layer chromatography control, the reaction mixture was filtered over Celite and the residue was rinsed with methanol. The filtrate was concentrated to dryness under reduced pressure. Yield: 89%

Stage (v): 341-(4-Methoxy-2,6-dimethylphenylsulfonyl)piperidin-2-yl)-propan-1-ol LAH (2.52 mmol, 2.2 eq) was initially introduced into THF (5 ml) at 0° C. and a solution of ethyl 3-(1-(4-methoxy-2,6-dimethylphenylsulfonyl)piperidin-2-yl)propanoate (1.14 mmol, 1 eq) in THF (5 ml) was slowly added. The mixture was stirred at room temperature for 30 min. The reaction was hydrolysed with aqueous Na$_2$SO$_4$ solution, the mixture was filtered over Celite and the filtrate was concentrated to dryness under reduced pressure. Yield: 100%

Stage (vi): 3-(1-(4-Methoxy-2,6-dimethylphenylsulfonyl)piperidin-2-yl)propyl methanesulfonate 3-(1-(4-Methoxy-2,6-dimethylphenylsulfonyl)piperidin-2-yl)propan-1-ol (1.19 mmol, 1 eq) was dissolved in methylene chloride (5 ml), and triethylamine (2.99 mmol, 2.5 eq) and methanesulfonic acid chloride (1.43 mmol, 1.2 eq) were added at 0° C. The mixture was stirred at room temperature for 1 h. The reaction mixture was then diluted with methylene chloride (20 ml), washed with water (10 ml) and saturated sodium chloride solution (8 ml), dried over sodium sulfate and concentrated. The crude product was employed in the next stage without further purification. Yield: 89%

Stage (vii) & (viii): 3-(1-(4-Methoxy-2,6-dimethylphenylsulfonyl)piperidin-2-yl)propane-1-sulfonyl chloride 3-(1-(4-Methoxy-2,6-dimethylphenylsulfonyl)piperidin-2-yl)propyl methanesulfonate (1.07 mmol, 1 eq) was dissolved in ethanol (7 ml), a solution of Na$_2$SO$_3$ (1.28 mmol, 2 eq) in water (7 ml) was added and the mixture was heated at the boiling temperature for 4 h. The reaction mixture was reduced to dryness, the residue was taken up in toluene/DMF (15 ml/0.1 ml) and SO$_2$Cl$_2$ (0.5 ml) was added. The resulting reaction mixture was heated under reflux for 4 h and was then concentrated to dryness. The residue was taken up in ethyl acetate (30 ml), washed with water (10 ml) and saturated sodium chloride solution (10 ml), dried over sodium sulfate and concentrated. The crude product was purified by column chromatography (2-15% ethyl acetate in hexane). Yield: 22%

Step-9: 3-(3-(1-(4-Methoxy-2,6-dimethylphenylsulfonyl)piperidin-2-yl)propyl-sulfonyl)-9-(pyridin-3-yl)-9-(2-(pyrrolidin-1-yl)ethoxy)-3-azaspiro[5.5]undecane 9-(Pyridin-3-yl)-9-(2-(pyrrolidin-1-yl)ethoxy)-3-azaspiro[5.5]undecane (0.26 mmol, 1 eq) was dissolved in methylene chloride (3 ml) at 0° C., triethylamine (1.04 mmol, 4 eq) was added, and 3-(1-(4-methoxy-2,6-dimethylphenylsulfonyl)piperidin-2-yl)propane-1-sulfonyl chloride (0.26 mmol, 1 eq), dissolved in methylene chloride (2 ml) was added to the mixture. After 1 h at room temperature, the mixture was diluted with methylene chloride (20 ml). The organic phase was washed with water (10 ml) and saturated sodium chloride solution (10 ml), dried over sodium sulfate and concentrated under reduced pressure. The crude product was purified by column chromatography (1-5% methanol in methylene chloride). Yield: 47%. MS, R$_f$=3.6 min, m/z=731.5 [MH]$^+$.

Pharmacological Data

The pharmacological data were determined as described above. The following data are given in the table below by way of example:

| Example | B1R antagonism, rat [10 µM] % inhibition | B1R antagonism, human [10 µM] % inhibition |
|---|---|---|
| 1 |  | 83 |
| 2 | 84 | 102 |
| 3 |  | 55 |
| 4 | 13 | 76 |
| 5 | 56 | 49 |
| 6 | 44 | 61 |
| 7 | 58 | 38 |
| 8 | 46 | 59 |
| 9 | 30 | 58 |
| 10 | 10 | 63 |
| 11 | 26 | 65 |
| 12 |  | 52 |
| 13 |  | 53 |
| 14 |  | 58 |

-continued

| Example | B1R antagonism, rat [10 µM] % inhibition | B1R antagonism, human [10 µM] % inhibition |
|---|---|---|
| 15 | 18 | 97 |
| 16 | 13 | 97 |
| 17 | 12 | 58 |
| 18 | 11 | 65 |
| 19 | 13 | 77 |
| 20 | 75 | 103 |
| 21 | 73 | 97 |
| 22 | 95 | 103 |
| 23 | 78 | 102 |
| 24 | 33 | 62 |
| 25 | 90 | 103 |
| 26 | 98 | 96 |
| 27 | 93 | 108 |
| 28 | 91 | 104 |
| 29 | 46 | 87 |
| 30 | 48 | 56 |
| 31 | 64 | 89 |
| 32 | 99 | 105 |
| 33 | 36 | 98 |
| 34 | 96 | 99 |
| 35 | 91 | 23 |
| 36 | 89 | 95 |
| 37 | 40 | 53 |
| 38 | 47 | 101 |
| 39 | 27 | 44 |
| 40 |  | 50 |
| 41 | 7 | 50 |
| 42 | 26 | 50 |
| 43 | 50 | 11 |
| 44 | 105 | 82 |
| 45 | 102 | 98 |
| 46 | 99 | 80 |
| 47 | 95 | 95 |
| 48 | 75 | 81 |
| 49 | 36 | 30 |
| 50 | 71 | 58 |
| 51 | 93 | 74 |
| 52 | 87 | 71 |
| 53 | 86 | 74 |
| 54 | 98 | 100 |
| 55 | 98 | 98 |
| 56 | 99 | 95 |
| 57 | 54 | 25 |
| 58 | 94 | 56 |
| 59 | 96 | 94 |
| 60 | 100 | 89 |
| 61 | 97 | 75 |
| 62 | 104 | 84 |
| 63 | 102 | 99 |
| 64 | 99 | 99 |
| 65 | 97 | 99 |
| 66 | 102 | 100 |
| 67 | 97 | 98 |
| 68 | 96 | 100 |
| 69 | 12 | 33 |
| 70 | 32 | 26 |
| 71 | 39 | 30 |
| 72 | 45 | 38 |
| 73 | 99 | 89 |
| 74 | 95 | 99 |
| 75 | 100 | 96 |
| 76 | 95 | 95 |
| 77 | 97 | 81 |
| 78 | 93 | 91 |
| 79 | 96 | 77 |
| 80 | 102 | 99 |
| 81 | 98 | 96 |
| 82 | 103 | 100 |
| 83 | 104 | 99 |
| 84 | 82 | 96 |
| 85 | 101 | 99 |
| 86 | 101 | 99 |
| 87 | 102 | 100 |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:

1. A substituted disulfonamide compound corresponding to the formula (I)

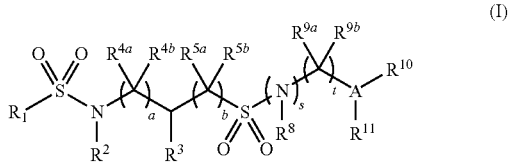

wherein
a represents 0, 1 or 2;
b represents 0, 1, 2, 3 or 4;
$R^1$ represents an aryl or heteroaryl group or an aryl or heteroaryl group bonded via a $C_{1-3}$-alkylene group, wherein the aryl or heteroaryl group optionally may be fused with a 4-, 5-, 6- or 7-membered carbocyclic or heterocyclic ring, wherein said carbocyclic or heterocyclic ring may be saturated or mono- or polyunsaturated, but not aromatic, and optionally may be substituted on one or more of its carbon ring members by one or more substituents independently selected from the group consisting of F, Cl, Br, I, —$CF_3$, —O—$CF_3$, and $C_{1-6}$-alkyl, and wherein the heterocyclic ring may contain one or more hetero atoms or hetero atom groups independently selected from the group consisting of N, $NR^{50}$, O, S, S=O or S(=O)$_2$; wherein
$R^{50}$ denotes H, a $C_{1-6}$-alkyl, —C(=O)—$R^{51}$, $C_{3-8}$-cycloalkyl, aryl or heteroaryl group, or a $C_{3-8}$-cycloalkyl, aryl or heteroaryl group bonded via a $C_{1-3}$-alkylene group, and
$R^{51}$ denotes a $C_{1-6}$-alkyl, $C_{3-8}$cycloalkyl, aryl or heteroaryl group, or a $C_{3-8}$-cycloalkyl, aryl or heteroaryl group bonded via a $C_{1-3}$-alkylene group;
$R^2$ and $R^3$, together with the —N—$(CR^{4a}R^{4b})_a$—CH— group joining them, form a saturated 4-, 5- or 6-membered heterocyclic ring which optionally may be substituted on one or more of its carbon ring members by one or more substituents independently selected from the group consisting of F, Cl, Br, I, —$CF_3$, —O—$CF_3$ and —SH and optionally may be fused with a benzo group;
$R^{4a}$, $R^{4b}$, $R^{5a}$ and $R^{5b}$ each independently represent H, F, Cl, Br, I, —$CF_3$, —$OCF_3$, OH, SH, O—$C_{1-6}$-alkyl, $C_{1-6}$-alkyl, $C_{3-8}$-cycloalkyl, aryl or heteroaryl; or a $C_{3-8}$-cycloalkyl, aryl or heteroaryl group bonded via a $C_{1-6}$-alkylene group or $C_{2-6}$-alkenylene group;
s is 0 or 1;
t is 0, 1, 2 or 3;
$R^8$ represents H, a $C_{1-6}$-alkyl, $C_{3-8}$cycloalkyl, aryl or heteroaryl group, or a $C_{3-8}$-cycloalkyl, aryl or heteroaryl group bonded via a $C_{1-6}$-alkylene group;
$R^{9a}$ and $R^{9b}$ each independently denote H, F, Cl, OH, $C_{1-6}$-alkyl, O—$C_{1-6}$-alkyl, $C_{3-8}$-cycloalkyl, aryl or heteroaryl, or a $C_{3-8}$-cycloalkyl, aryl or heteroaryl group bonded via a $C_{1-6}$-alkylene group;
A represents N or CH;
with the proviso that if s is 1 and t is 0, then A represents CH; and
with the proviso that if s and t are each 0, then A represents N;

$R^{10}$ and $R^{11}$ together with A, represent a spirocyclic or cyclic group corresponding to formula (II) or formula (III):

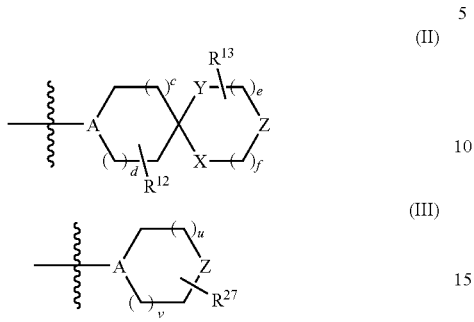

(II)

(III)

wherein c, d, e, f, u and v each independently denote 0, 1 or 2;

$R^{12}$, $R^{13}$ and $R^{27}$ each independently represent 0 to 4 substituents independently selected from the group consisting of F, Cl, OH, =O, $C_{1-6}$-alkyl, O—$C_{1-6}$-alkyl, $C_{3-8}$-cycloalkyl, aryl, heteroaryl and $C_{3-8}$-cycloalkyl, aryl or heteroaryl group bonded via a $C_{1-6}$-alkylene group; or two substituents $R^{27}$ together represent a $C_{1-3}$-alkylene bridge, so that the ring in formula (III) assumes a bicyclically bridged form; or two adjacent substituents $R^{13}$ form a fused aryl or heteroaryl ring; or two adjacent substituents $R^{27}$ form a fused aryl or heteroaryl ring;

X represents $CR^{14a}R^{14b}$, $NR^{15}$ or O;

Y represents $CR^{16a}R^{16b}$, $NR^{17}$ or O;

with the proviso that X is not $NR^{15}$ if Y is $NR^{17}$; and with the proviso that X and Y are not simultaneously O;

wherein $R^{14a}$, $R^{14b}$, $R^{16a}$ and $R^{16b}$ each independently denote H, F, Cl, OH, $C_{1-6}$-alkyl, O—$C_{1-6}$-alkyl, $C_{3-8}$-cycloalkyl, aryl or heteroaryl, or a $C_{3-8}$-cycloalkyl, aryl or heteroaryl group bonded via a $C_{1-6}$-alkylene group; or $R^{14a}$ and $R^{14b}$ may together represent =O; or $R^{16a}$ and $R^{16b}$ may together represent =O;

$R^{15}$ and $R^{17}$ each independently represent H, $C_{1-6}$-alkyl, $C_{3-8}$-cycloalkyl, aryl or heteroaryl, or a $C_{3-8}$-cycloalkyl, aryl or heteroaryl group bonded via a $C_{1-6}$-alkylene group;

Z in formula (II) represents $CR^{18a}R^{18}b$, $NR^{19}$ or O; or

Z in formula (II), if X represents O, and f is 0, denotes —(C($R^{124}$)—C($R^{125}$))—, wherein $R^{124}$ and $R^{125}$ together with the carbon atoms joining them, form a condensed on aryl or heteroaryl group; or Z in formula (II), if X represents O and f is 0, denotes =N($CR^{126}$))—, wherein the N atom is bonded to the O atom via a single bond, and $R^{126}$ represents H, $C_{1-6}$-alkyl, $C_{3-8}$cycloalkyl, aryl or heteroaryl, or a $C_{3-8}$-cycloalkyl, aryl or heteroaryl group bonded via a $C_{1-6}$-alkylene group;

Z in formula (III) represents $CR^{18a}R^{18b}$, $NR^{19}$, O, S, S(=O) or S(=O)$_2$; wherein $R^{18a}$ represents H, $C_{1-6}$-alkyl, $C_{3-8}$cycloalkyl, aryl or heteroaryl, or a $C_{3-8}$-cycloalkyl, aryl or heteroaryl group bonded via a $C_{1-6}$-alkylene group, or $R^{18a}$ represents a group corresponding to formula (IV)

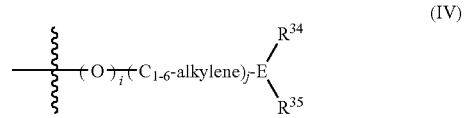

(IV)

wherein i and j each independently are 0 or 1;

E represents N or CH, with the proviso that if i is 1 and j is 0, then E represents CH;

$R^{34}$ and $R^{35}$ each independently denote H, $C_{1-6}$-alkyl, $C_{3-8}$-cycloalkyl, aryl or heteroaryl, or an aryl, heteroaryl or $C_{3-8}$-cycloalkyl group bonded via a $C_{1-3}$-alkylene group; or $R^{34}$ and $R^{35}$ together with E, form a 5- or 6-membered aryl or heteroaryl group; or $R^{34}$ and $R^{35}$ together with E, form a saturated heterocyclic ring corresponding to formula (V)

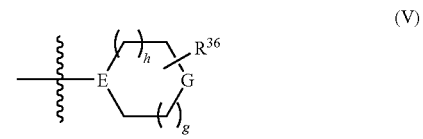

(V)

wherein h and g each independently are 0, 1 or 2;

G represents $CR^{37a}R^{37b}$, $NR^{38}$, O, S, S=O or S(=O)$_2$, with the proviso that if E represents CH, G is not $CR^{37a}R^{37b}$; wherein $R^{37a}$ and $R^{37b}$ each independently denote H, F, Cl, Br, I, OH, SH, =O, O—$C_{1-6}$-alkyl, $C_{1-6}$-alkyl, $C_{3-8}$-cycloalkyl, aryl or heteroaryl, or a $C_{3-8}$-cycloalkyl, aryl or heteroaryl group bonded via a $C_{1-6}$-alkylene group; and $R^{38}$ represents H, $C_{1-6}$-alkyl, $C_{3-8}$-cycloalkyl, aryl or heteroaryl or an aryl, heteroaryl or $C_{3-8}$-cycloalkyl group bonded via a $C_{1-3}$-alkylene group;

$R^{36}$ represents 0 to 4 substituents independently selected from the group consisting of F, Cl, Br, I, OH, SH, =O, O—$C_{1-6}$-alkyl, $C_{1-6}$-alkyl, $C_{3-8}$-cycloalkyl, aryl, heteroaryl and a $C_{3-8}$-cycloalkyl, aryl or heteroaryl group bonded via a $C_{1-6}$-alkylene group; or two adjacent substituents $R^{36}$ together represent a fused aryl or heteroaryl group;

$R^{18b}$ represents H, OH, $C_{1-6}$-alkyl, $C_{3-8}$-cycloalkyl, O—$C_{1-6}$-alkyl, O—($C_{3-8}$-cycloalkyl), ($C_{1-6}$-alkylene)-O—$C_{1-6}$-alkyl, ($C_{1-6}$-alkylene)-O—($C_{3-8}$-cycloalkyl), aryl, heteroaryl, O-aryl or O-heteroaryl, or an aryl, O-aryl, heteroaryl or O-heteroaryl group bonded via a $C_{1-6}$-alkylene group; or $R^{18b}$ represents a group corresponding to formula (VI)

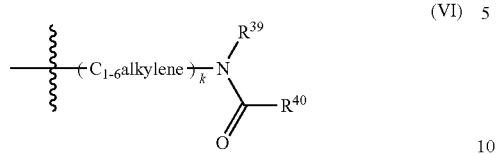

wherein k is 0 or 1;

$R^{39}$ represents H, $C_{1-6}$-alkyl, $C_{3-8}$-cycloalkyl, aryl or heteroaryl, or a $C_{3-8}$-cycloalkyl, aryl or heteroaryl group bonded via a $C_{1-3}$-alkylene group;

$R^{40}$ represents $C_{1-6}$-alkyl, $C_{3-8}$cycloalkyl, aryl or heteroaryl, or a $C_{3-8}$-cyclo-alkyl, aryl or heteroaryl group bonded via a $C_{1-6}$-alkylene group; or $R^{39}$ and $R^{40}$, together with the N—C(=O) group joining them, form a ring corresponding to formula (VII)

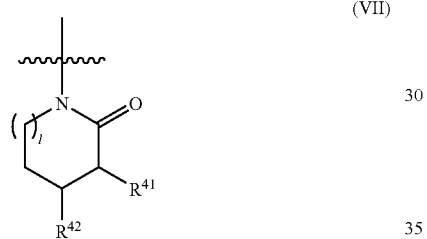

wherein l is 0, 1 or 2; and $R^{41}$ and $R^{42}$, together with the carbon atoms joining them, form a fused aryl or heteroaryl group;

$R^{19}$ represents H, or $(P)_z$—$R^{22}$, wherein z is 0 or 1; and

P represents (C=O), S(=O)$_2$ or C(=O)—N($R^{24}$), wherein the N atom in the group C(=O)—N($R^{24}$) is linked to $R^{22}$, wherein $R^{24}$ represents H, $C_{1-6}$-alkyl, $C_{3-8}$-cycloalkyl or an aryl, heteroaryl or $C_{3-8}$-cycloalkyl group bonded via a $C_{1-3}$-alkylene group; and $R^{22}$ represents a $C_{1-6}$-alkyl, aryl or heteroaryl group, or an aryl or heteroaryl group bonded via a $C_{1-6}$-alkylene group; or $R^{22}$ represents a group corresponding to formula (VIII), wherein

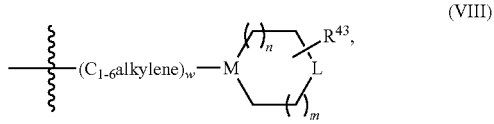

n is 0, 1 or 2;

m is 0, 1 or 2;

w is 0 or 1;

M represents CH or N;

with the proviso that if P represents C(=O)—N$R^{24}$ and w is 0, then M represents CH; and with the proviso that if z and w are both 0, then M represents CH;

L represents $CR^{44a}R^{44b}$, $NR^{45}$, O, S, S=O or S(=O)$_2$; wherein $R^{44a}$ and $R^{44b}$ each independently represent H, F, Cl, Br, I, OH, $C_{1-6}$-alkyl, O—$C_{1-6}$-alkyl, $C_{3-8}$-cycloalkyl, aryl or heteroaryl, or a $C_{3-8}$-cycloalkyl, aryl or heteroaryl group bonded via a $C_{1-6}$-alkylene group; or $R^{44a}$ and $R^{44b}$ may together represent =O; and $R^{45}$ represents H, a $C_{1-6}$-alkyl, $C_{3-8}$-cycloalkyl, aryl or heteroaryl group, or an aryl, heteroaryl or $C_{3-8}$-cycloalkyl group bonded via a $C_{1-3}$-alkylene group;

$R^{43}$ represents 0 to 4 substituents independently selected from the group consisting of F, Cl, OH, =O, $C_{1-6}$-alkyl, O—$C_{1-6}$-alkyl, $C_{3-8}$-cycloalkyl, aryl, heteroaryl and a $C_{3-8}$-cycloalkyl, aryl or heteroaryl group bonded via a $C_{1-6}$-alkylene group; or two adjacent groups $R^{43}$ together represent a fused aryl or heteroaryl group;

wherein the abovementioned $C_{1-6}$-alkyl, $C_{1-3}$-alkylene, $C_{1-6}$-alkylene, $C_{2-6}$-alkenylene, $C_{2-6}$-alkynylene, $C_{3-6}$-cycloalkyl, $C_{3-8}$-cycloalkyl, aryl and heteroaryl groups may each be unsubstituted or substituted one or more times by identical or different substituents, and the abovementioned $C_{1-6}$-alkyl, $C_{1-3}$-alkylene, $C_{1-6}$-alkylene, $C_{2-6}$-alkenylene and $C_{2-6}$-alkynylene groups may each be branched or unbranched;

or a physiologically acceptable salt thereof.

2. A compound as claimed in claim 1, wherein said compound is in the form of an isolated stereoisomer.

3. A compound as claimed in claim 1, wherein said compound is in the form of a mixture of stereoisomers in any mixing ratio.

4. A compound as claimed in claim 3, wherein said mixture is a racemic mixture.

5. A compound as claimed in claim 1, wherein $R^1$ represents phenyl, naphthyl, chromanyl, indolyl, benzofuranyl, benzothiophenyl, benzooxazolyl, benzooxadiazolyl, pyrrolyl, furanyl, thienyl, pyridinyl, pyridazinyl, pyrimidinyl, pyrazinyl, imidazothiazolyl, carbazolyl, dibenzofuranyl, dibenzothiophenyl, or a phenyl or naphthyl bonded via a $C_{1-3}$-alkylene group, wherein the abovementioned aryl or heteroaryl groups may each be unsubstituted or substituted one or more times by identical or different substituents independently selected from the group consisting of —O—$C_{1-3}$-alkyl, $C_{1-6}$-alkyl, F, Cl, Br, I, $CF_3$, $OCF_3$, OH, SH, phenyl, phenoxy, naphthyl, furyl, thienyl and pyridinyl, and the abovementioned alkylene groups may each be unsubstituted or substituted one or more times by identical or different substituents independently selected from the group consisting of —O—$C_{1-3}$-alkyl, F, Cl, Br, I, $CF_3$, $OCF_3$, OH, SH, phenyl, phenoxy, naphthyl, furyl, thienyl and pyridinyl.

6. A compound as claimed in claim 5, wherein $R^1$ represents an optionally substituted phenyl, naphthyl, chromanyl, benzothiophenyl, benzooxadiazolyl, thienyl, pyridinyl, imidazothiazolyl, or dibenzofuranyl group, or a phenyl group bonded via a $C_{1-3}$-alkylene group.

7. A compound as claimed in claim 1, wherein in formula (I) the partial structure (Ac I)

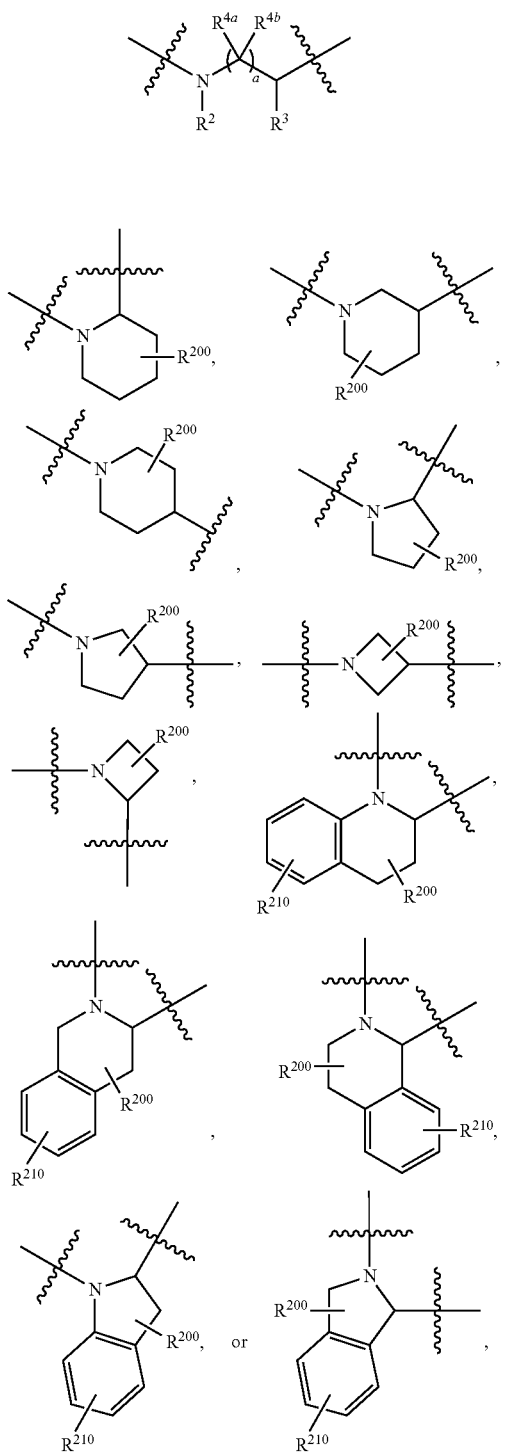

represents wherein $R^{200}$ represent 0-4 substituents independently selected from the group consisting of F, Cl, —$CF_3$ and —O—$CF_3$, or two adjacent $R^{200}$ groups together form a fused aryl or heteroaryl group; and $R^{210}$ represents 0-4 substituents independently selected from the group consisting of —O—$C_{1-3}$-alkyl, $C_{1-6}$-alkyl, F, Cl, Br, I, $CF_3$, $OCF_3$, OH, SH, phenyl, naphthyl, furyl, thienyl and pyridinyl.

8. A compound as claimed in claim 7, wherein $R^{200}$ represents F or $CF_3$, or two adjacent $R^{200}$ groups together form a benzo group; and $R^{210}$ represents 0-4 substituents independently selected from the group consisting of methyl, methoxy, $CF_3$, $OCF_3$, F, Cl and Br.

9. A compound as claimed in claim 1, wherein in formula (I) the partial structure:

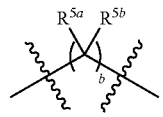

represents a —$CH_2$—, —$(CH_2)_2$—, —$(CH_2)_3$— or —$(CH_2)_4$— group.

10. A compound as claimed in claim 1, wherein $R^8$ represents H, $C_{1-6}$-alkyl, $C_{3-6}$-cycloalkyl, —$CH_2CF_3$, phenyl, benzyl, phenylethyl, phenylpropyl, or $C_{3-6}$-cycloalkyl bonded via a $C_{1-3}$-alkylene group, in each case unsubstituted or substituted one or more times by identical or different substituents.

11. A compound as claimed in claim 1, wherein $R^{9a}$ and $R^{9b}$ each independently represent H, F, methyl, ethyl, isopropyl, $CF_3$, methoxy, cyclopropyl, phenyl, benzyl, phenylethyl or a cycloalkyl or —$CF_3$ bonded via a $C_{1-3}$-alkylene group, in each case unsubstituted or substituted one or more times by identical or different substituents.

12. A compound as claimed in claim 1, wherein (a1) formula (II) assumes the following partial structure IIa:

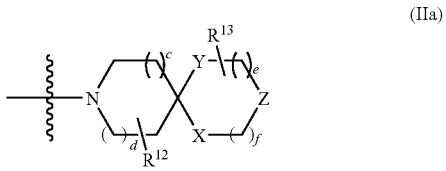

(IIa)

or (a2) formula (III) assumes one of the following partial structures (IIIa) or (IIIb):

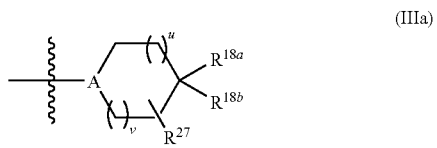

(IIIa)

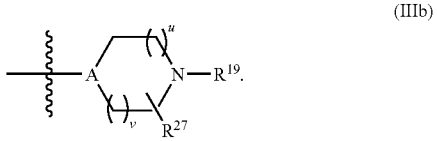

(IIIb)

13. A compound as claimed in claim 12, wherein
(a1) the partial structure of formula (IIa) assumes the following partial structure (IIb):

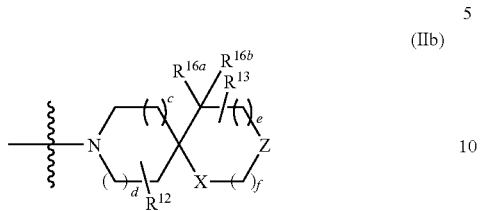

or
(a2) the partial structures of formulas (IIIc) and (IIIb) assume one of the following partial structures (IIIc), (IIId) or (IIIe):

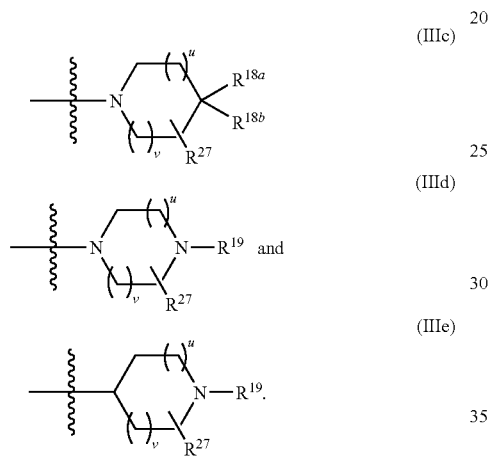

14. A compound as claimed in claim 13, wherein
(a1) the partial structure of formula (IIa) assumes the partial structure (IIb);
$R^8$ represents H, $C_{1-6}$-alkyl or $C_{3-6}$-cycloalkyl, in each case unsubstituted or substituted one or more times by identical or different substituents, and
$R^{9a}$ and $R^{9b}$ in each case represent H;
or
(a2) the partial structures of formulas (IIIa) and (IIIb) assume one of the partial structures (IIIc) or (IIId), and s and t each are 0;
or
(a3) the partial structures of formulas (IIa) and (IIIb) assume one of the partial structures (IIIc) or (IIId), and two $R^{27}$ substituents together represent a $C_{1-3}$-alkylene bridge, so that the ring shown in the part structure (IIIc) or (IIId) assumes a bicyclically bridged form, and
s and t each are 0;
or
(a4) the partial structures of formulas (IIIa) and (IIIb) assume one of the partial structures (IIIc) or (IIIe);
s is 1;
t is 1, 2 or 3, and
$R^8$ represents H, $C_{1-6}$-alkyl or $C_{3-6}$-cycloalkyl, in each case unsubstituted or substituted one or more times by identical or different substituents.

15. A compound as claimed in claim 14, wherein
(a1) the partial structure (IIb) assumes the following part structure (IIc):

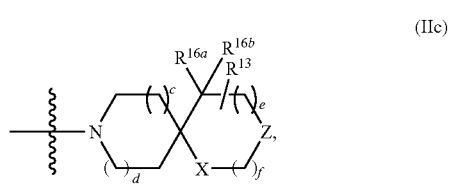

wherein s and t each are 0; or
(a2) the partial structures (IIIc) or (IIId) assume one of the following partial structures (IIIf) or (IIIg):

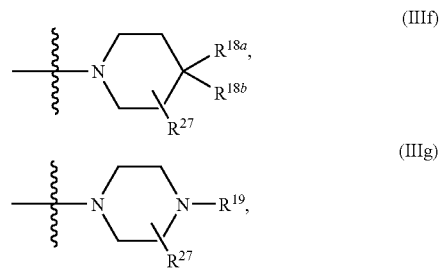

wherein
$R^{27}$ represents H or methyl, or two adjacent $R^{27}$ substituents form a fused aryl or heteroaryl ring;
or
(a3) the partial structures (IIIc) or (IIId) represent one of the following groups A to H:

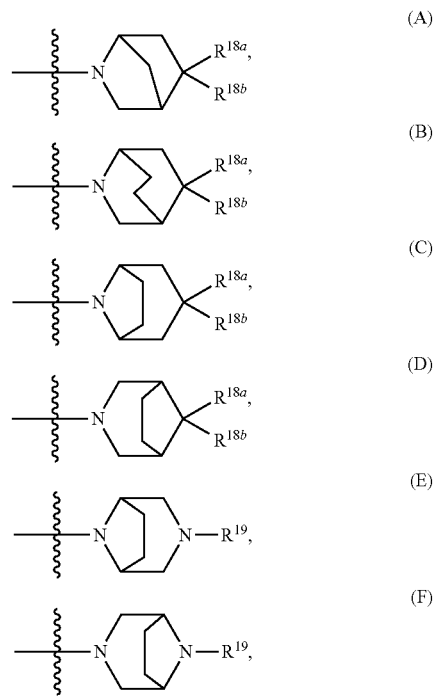

-continued

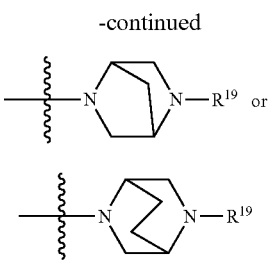

or
(a4) the partial structures (IIIc) or (IIIe) represent a group corresponding to one of the formulas (IIIh) or (IIIi):

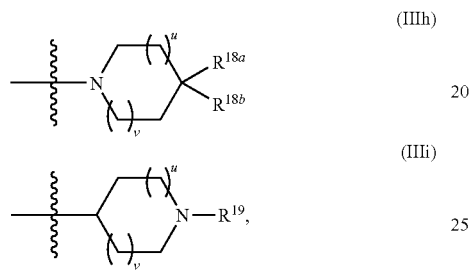

and $R^{9a}$ and $R^{9b}$ each represent H.

16. A compound as claimed in claim 15, wherein
(a1) in the partial structure (IIc),
$R^{16a}$ and $R^{16b}$ each denote H or together form =O; and
$R^{13}$ represents H, aryl or heteroaryl; or
two $R^{13}$ substituents together form =O; or
two adjacent $R^{13}$ substituents form a fused aryl or heteroaryl group;
or
(a2) in the partial structures (IIIf) or (IIIg),
$R^{18a}$ represents H, $C_{1-6}$-alkyl, $C_{3-8}$-cycloalkyl, —NH($C_{1-6}$-alkyl), —N($C_{1-6}$-alkyl)$_2$, phenyl, pyridyl, imidazolyl, triazolyl, pyrimidyl, thiazolyl or thienyl, in each case unsubstituted or substituted one or more times; or phenyl, pyridyl, imidazolyl, triazolyl, pyrimidyl, thiazolyl or thienyl bonded via an —(O)$_{0-1}$—$C_{1-6}$-alkylene group, in each case unsubstituted or substituted one or more times; or
$R^{18a}$ represents a group corresponding to formula (VIIa)

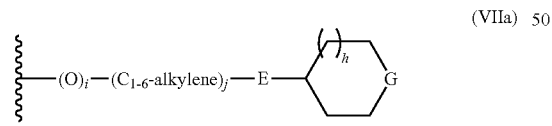

wherein
i is 0 or 1;
j is 0 or 1;
h is 0 or 1;
E represents N or CH; with the proviso that if i is 1 and j is 0, then E represents CH;
G represents $CR^{37a}R^{37b}$ or $NR^{38}$, wherein
$R^{37a}$ and $R^{37b}$ each independently represent H, F or $C_{1-6}$-alkyl, in each case unsubstituted or substituted one or more times by identical or different substituents; and
$R^{38}$ represents H, $C_{1-6}$-alkyl, $C_{3-6}$-alkyl or pyridyl;

$R^{18b}$ represents H, OH, $C_{1-6}$-alkyl, phenyl, pyridyl, imidazolyl, triazolyl, pyrimidyl, thiazolyl or thienyl, in each case unsubstituted or substituted one or more times by identical or different substituents, or phenyl, pyridyl, imidazolyl, triazolyl, pyrimidyl, thiazolyl or thienyl, O-phenyl or O-pyridyl bonded via a $C_{1-6}$-alkylene group, in each case unsubstituted or substituted one or more times by identical or different substituents; or phenyl, pyridyl or thienyl bridged via $C_{1-6}$-alkylene-NH(C=O), in each case unsubstituted or substituted one or more times by identical or different substituents;

$R^{19}$ represents H, $C_{1-6}$-cycloalkyl, or $C_{1-6}$-alkyl bonded via (C=O)$_{0-1}$, phenyl, pyridyl, thienyl, thiazolyl, triazolyl, pyrimidinyl or imidazolyl; in each case unsubstituted or substituted one or more times by identical or different substituents; or phenyl, pyridyl, thienyl, thiazolyl, pyrimidinyl, triazolyl or imidazolyl bonded via a $C_{1-6}$-alkylene group; in each case unsubstituted or substituted one or more times by identical or different substituents; or
a group corresponding to formula (VIIIa)

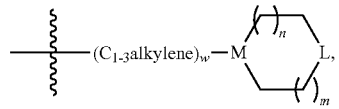

wherein
w is 0 or 1;
n is 0 or 1;
m is 0 or 1;
M represents CH or N, with the proviso that if w is 0, then M represents CH;
L represents $CR^{44a}R^{44b}$ or $NR^{45}$; wherein
$R^{44a}$ and $R^{44b}$ each independently represent H, F or $C_{1-6}$-alkyl, in each case unsubstituted or substituted one or more times by identical or different substituents; and
$R^{45}$ represents H, $C_{1-6}$-alkyl, $C_{3-6}$-alkyl or pyridyl;
or
(a3) the partial structures (IIIc) or (IIId) represent one of the following groups H: to H:

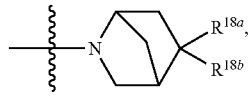
(A)

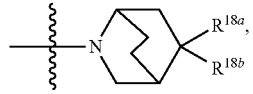
(B)

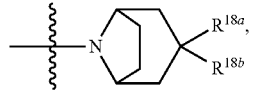
(C)

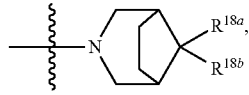
(D)

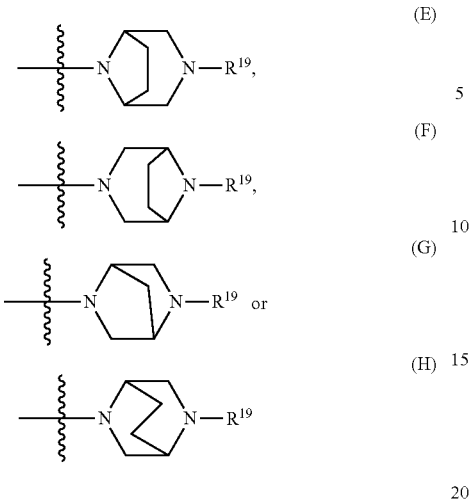

and wherein
- $R^{18a}$ represents H, $C_{1-6}$-alkyl, $C_{3-8}$-cycloalkyl, $N(C_{1-6}$-alkyl$)_2$, $NH(C_{1-6}$-alkyl), azetidinyl, pyrrolidinyl, piperidinyl, 4-($C_{1-6}$-alkyl)-piperazinyl, phenyl or pyridyl, in each case unsubstituted or substituted one or more times by identical or different substituents; or $N(C_{1-6}$-alkyl$)_2$, $NH(C_{1-6}$-alkyl), azetidinyl, pyrrolidinyl, piperidinyl, 4-($C_{1-6}$-alkyl)-piperazinyl, phenyl, imidazolyl, triazolyl or pyridyl bonded via a $-(O)_{0-1}-C_{1-6}$-alkylene group, in each case unsubstituted or substituted one or more times by identical or different substituents;
- $R^{18b}$ represents H, OH, $C_{1-6}$-alkyl, phenyl or pyridyl, in each case unsubstituted or substituted one or more times by identical or different substituents; or phenyl or pyridyl bonded via a $C_{1-6}$-alkylene group, in each case unsubstituted or substituted one or more times by identical or different substituents; and
- $R^{19}$ represents H, $C_{3-8}$-cycloalkyl, phenyl, pyridyl, thienyl, imidazolyl, thiazolyl or triazolyl, in each case unsubstituted or substituted one or more times by identical or different substituents; phenyl, pyridyl, thienyl, imidazolyl, thiazolyl, or triazolyl bonded via a $C_{1-6}$-alkylene group or a (C=O) group, in each case unsubstituted or substituted one or more times by identical or different substituents;

or (a4) in the partial structures (IIIh) or (IIIi)
- $R^{18a}$ represents H, $C_{1-6}$-alkyl, $C_{3-8}$-cycloalkyl, $N(C_{1-6}$-alkyl$)_2$, $NH(C_{1-6}$-alkyl), azetidinyl, pyrrolidinyl, piperidinyl, 4-($C_{1-6}$-alkyl)-piperazinyl, phenyl or pyridyl, in each case unsubstituted or substituted one or more times by identical or different substituents; or $N(C_{1-6}$-alkyl$)_2$, $NH(C_{1-6}$-alkyl), azetidinyl, pyrrolidinyl, piperidinyl, 4-($C_{1-6}$-alkyl)-piperazinyl, phenyl, imidazolyl, triazolyl, or pyridyl bonded via a $-(O)_{0-1}-C_{1-6}$-alkylene group, in each case unsubstituted or substituted one or more times by identical or different substituents;
- $R^{18b}$ represents H, OH, $C_{1-6}$-alkyl, phenyl or pyridyl, in each case unsubstituted or substituted one or more times by identical or different substituents; or phenyl or pyridyl bonded via a $C_{1-6}$-alkylene group, in each case unsubstituted or substituted one or more times by identical or different substituents; and
- $R^{19}$ represents H, $C_{1-6}$-alkyl, $C_{3-8}$-cycloalkyl, phenyl, pyridyl, thienyl, imidazolyl, thiazolyl, or triazolyl, in each case unsubstituted or substituted one or more times by identical or different substituents; or phenyl or pyridyl bonded via a $C_{1-6}$-alkylene group or (C=O) group, in each case unsubstituted or substituted one or more times by identical or different substituents.

17. A compound as claimed in claim 16, wherein
(a1) the partial structure of formula (IIc) assumes one of the following partial structures:

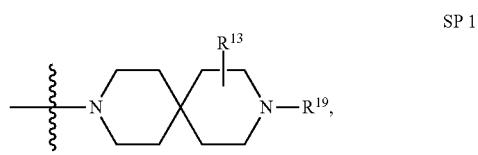

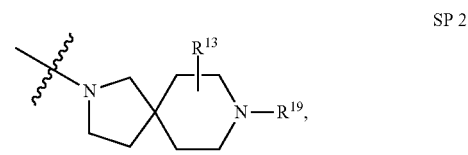

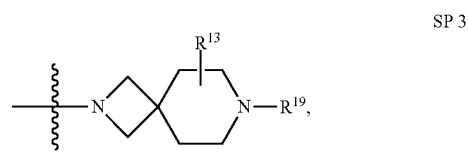

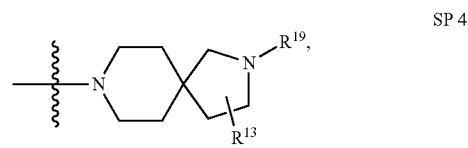

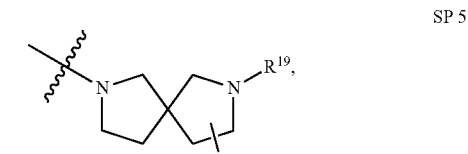

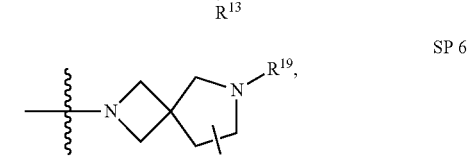

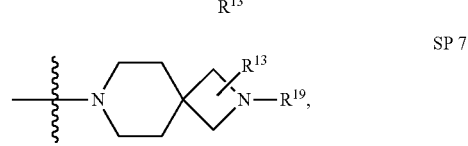

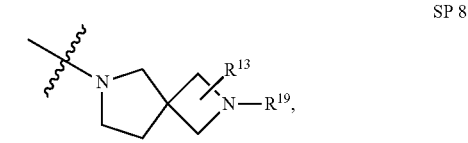

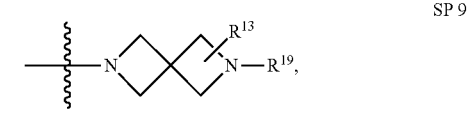

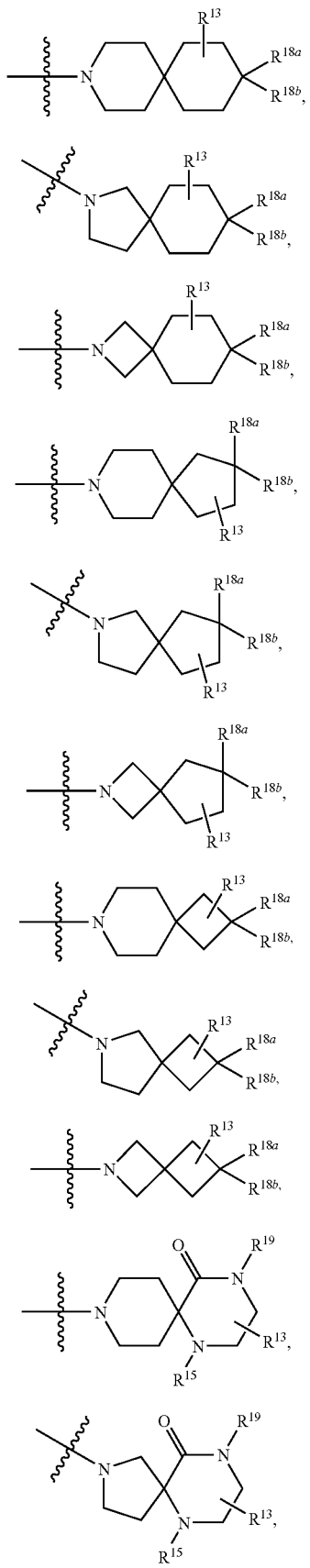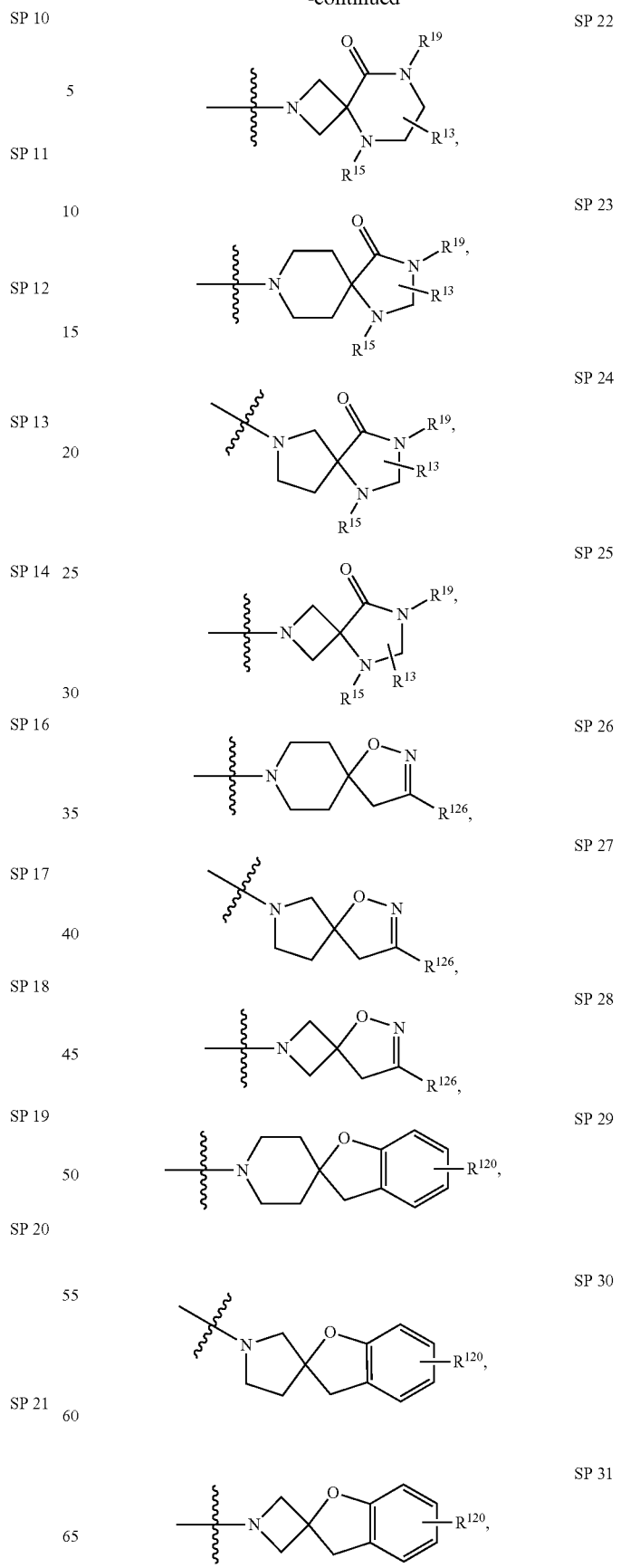

-continued

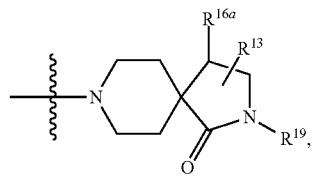
SP 32

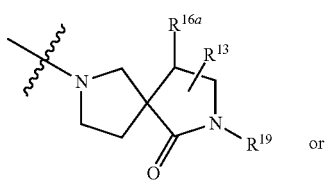
SP 33 or

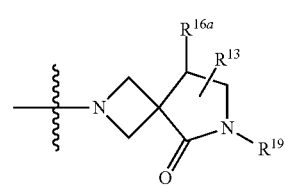
SP 34 wherein
$R^{13}$ represents H or phenyl, unsubstituted or substituted one or more times by identical or different substituents; or two $R^{13}$ substituents together form =O; or two adjacent $R^{13}$ substituents together form a fused aryl or heteroaryl group, in each case unsubstituted or substituted one or more times by identical or different substituents;

$R^{15}$ represents H, $C_{1-6}$-alkyl, $C_{3-8}$-cycloalkyl, phenyl, pyridyl, in each case unsubstituted or substituted one or more times by identical or different substituents; or phenyl or pyridyl bonded via a $C_{1-6}$-alkylene group, in each case unsubstituted or substituted one or more times by identical or different substituents;

$R^{16a}$ represents H, $C_{1-6}$-alkyl, phenyl or pyridyl, in each case unsubstituted or substituted one or more times by identical or different substituents;

$R^{18a}$ represents H, $C_{1-6}$-alkyl $C_{3-8}$-cycloalkyl, $N(C_{1-6}$-alkyl)$_2$, NH($C_{1-6}$-alkyl), azetidinyl, pyrrolidinyl, piperidinyl, 4-($C_{1-6}$alkyl)-piperazinyl, phenyl or pyridyl, in each case unsubstituted or substituted one or more times by identical or different substituents; or $N(C_{1-6}$-alkyl)$_2$, NH($C_{1-6}$-alkyl), azetidinyl, pyrrolidinyl, piperidinyl, 4-($C_{1-6}$-alkyl)-piperazinyl, phenyl, imidazolyl, triazolyl, or pyridyl bonded via a —(O)$_{0/1}$—$C_{1-6}$-alkylene group, in each case unsubstituted or substituted one or more times by identical or different substituents;

$R^{18b}$ represents H, OH, $C_{1-6}$-alkyl, phenyl or pyridyl, in each case unsubstituted or substituted one or more times by identical or different substituents; or phenyl or pyridyl bonded via a $C_{1-6}$-alkylene group, in each case unsubstituted or substituted one or more times by identical or different substituents;

$R^{19}$ represents H, $C_{1-6}$-alkyl, $C_{3-8}$-cycloalkyl, phenyl, pyridyl, thienly, imidazolyl, thiazolyl, or triazolyl, in each case unsubstituted or substituted one or more times by identical or different substituents; or phenyl or pyridyl bonded via a $C_{1-6}$-alkylene group or (C=O) group, in each case unsubstituted or substituted one or more times by identical or different substituents;

$R^{120}$ represents H, F, Cl, OH, OCH$_3$, O—CF$_3$, $C_{1-6}$-alkyl, CF$_3$, or phenyl, unsubstituted or substituted one or more times; and $R^{126}$ represents H, $C_{1-6}$-alkyl, $C_{3-6}$cycloalkyl, phenyl or pyridyl, or $C_{3-6}$-cycloalkyl, phenyl or pyridyl bonded via a $C_{1-3}$-alkylene group, in each case unsubstituted or substituted one or more times by identical or different substituents.

18. A compound as claimed in claim 1, wherein in formula (I) the following part structure (B):

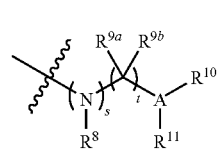
(B)

is selected from the group consisting of:
wherein
h is 0 or 1;
g is 0 or 1;
m is 0 or 1;

(B.1.)

(B.2.)

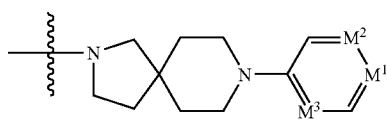
(B.3.)

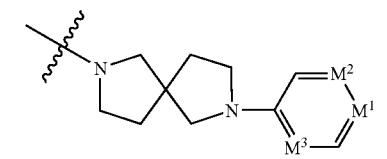
(B.4)

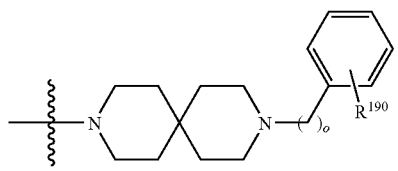
(B.5.)

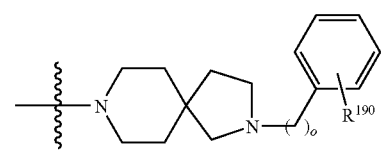
(B.6.)

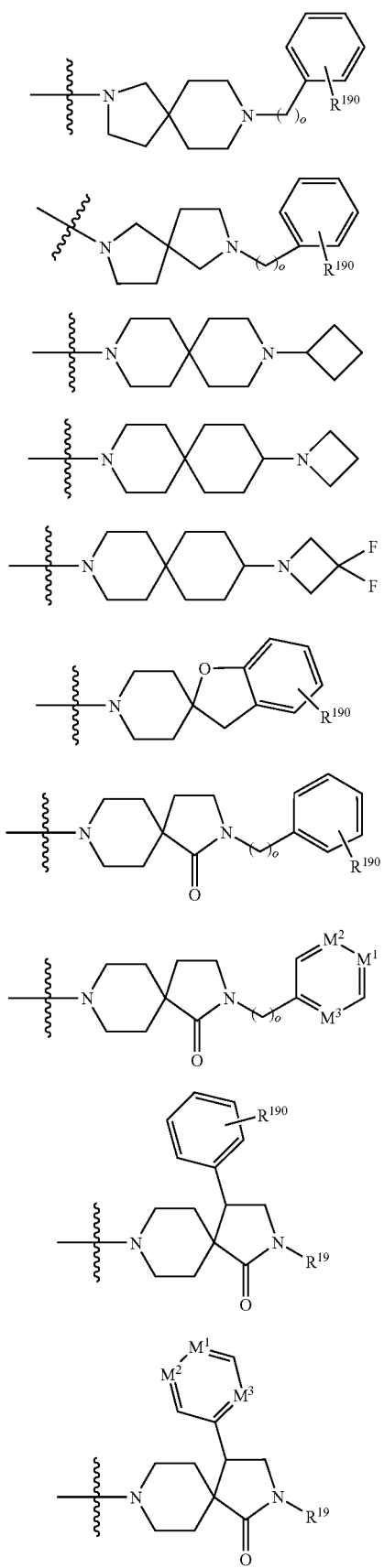
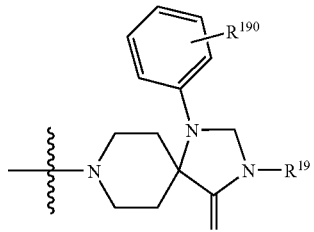
(B.17.)
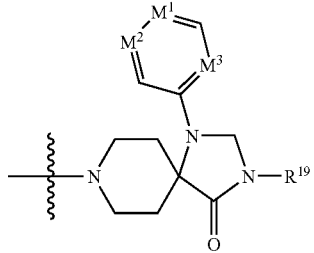
(B.18.)
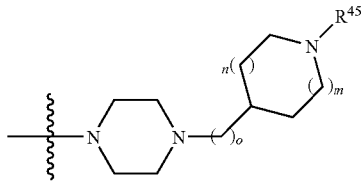
(B.19.)
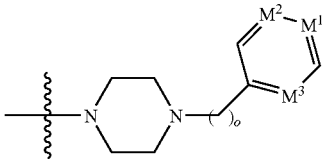
(B.20.)
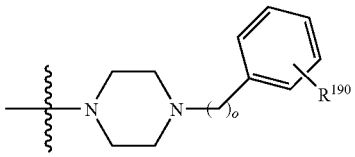
(B.21.)
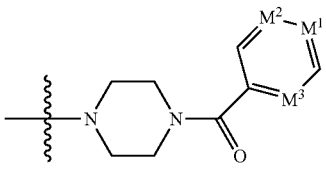
(B.22.)
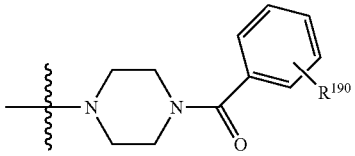
(B.23.)
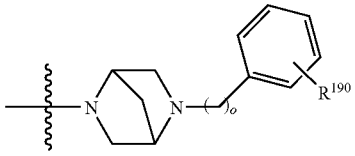
(B.24.)

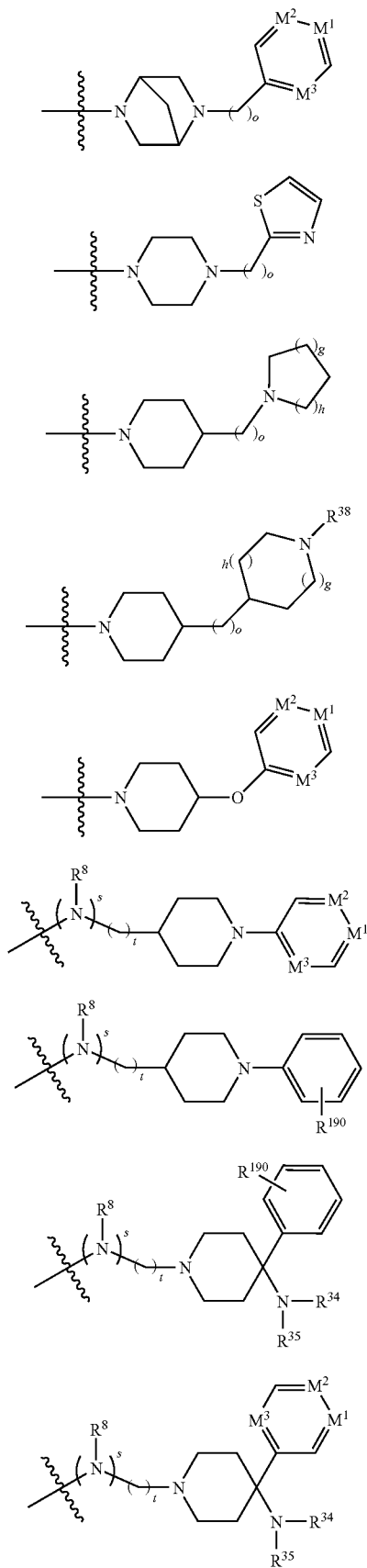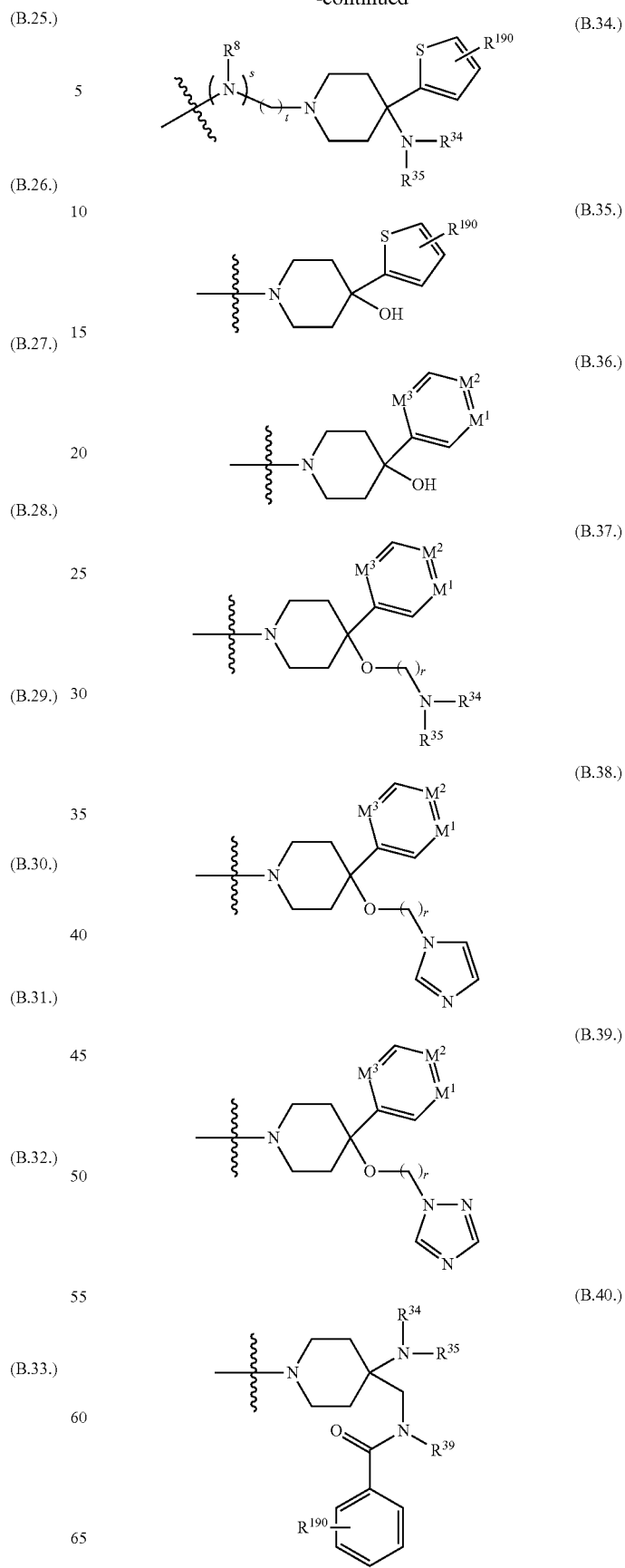

-continued (B.41.)
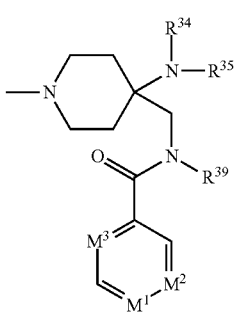

(B.42.)
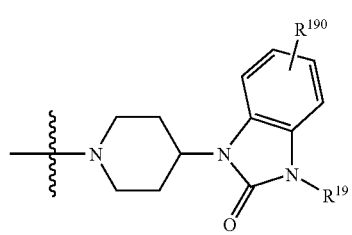

(B.43.)
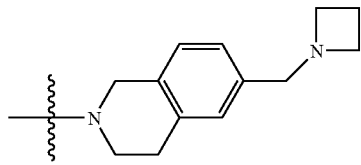

(B.44.)
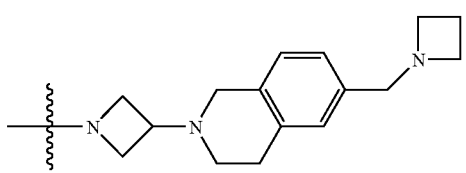

(B.45.)
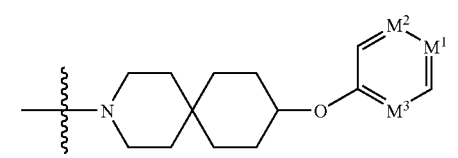

(B.46.)
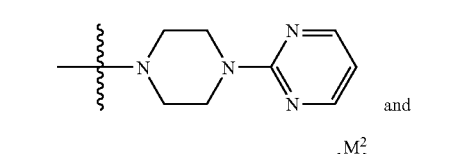
and (B.47.)
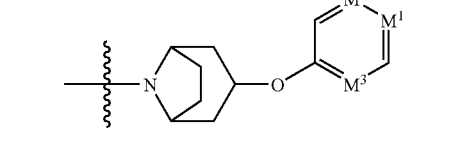

n is 0 or 1;
o is 1, 2 or 3;
r is 1, 2 or 3;
s is 0 or 1;
t is 0, 1, 2 or 3, with the proviso that if s is 0, then t is also 0;
$M^1$, $M^2$ and $M^3$ each represent N or CH, wherein one of $M^1$, $M^2$ and $M^3$ represents N, and the other two each represent CH;
$R^8$ represents H, $C_{1-6}$alkyl, $C_{3-6}$cycloalkyl, in each case unsubstituted or substituted one or more times by identical or different substituents;
$R^{19}$ is H, $C_{1-6}$alkyl, or $C_{3-6}$cycloalkyl, in each case unsubstituted or substituted one or more times by identical or different substituents;

$R^{34}$ and $R^{35}$ each independently represent methyl or ethyl, or together with the N atom joining them form an azetidinyl, pyrrolidinyl, piperidinyl, or 4-($C_{1-6}$alkyl)-piperazinyl group, in each case unsubstituted or substituted one or more times by identical or different substituents;
$R^{38}$ represents H, $C_{1-6}$-alkyl, $C_{3-6}$-cycloalkyl, or pyridyl;
$R^{39}$ is selected from H, $C_{1-6}$alkyl or $C_{3-6}$cycloalkyl, in each case unsubstituted or substituted one or more times by identical or different substituents;
$R^{45}$ represents H, $C_{3-6}$-cycloalkyl or pyridyl; and
$R^{190}$ represents 0-4 substituents independently selected from the group consisting of F, Cl, O—$CF_3$, $CF_3$ and CN.

19. A compound as claimed in claim 1, selected from the group consisting of:

| | |
|---|---|
| 1 | 1-(2-(1-(Mesitylsulfonyl)pyrrolidin-3-yl)ethylsulfonyl)-4-(2-(pyrrolidin-1-yl)ethyl)piperidine |
| 2 | (R)-1-(3-(1-(Naphthalen-2-ylsulfonyl)pyrrolidin-2-yl)propylsulfonyl)-4-(pyridin-4-yl)piperazine hydrochloride |
| 3 | 1-(2-(1-(Benzo[b]thiophen-3-ylsulfonyl)pyrrolidin-3-yl)ethylsulfonyl)-4-(2-(pyrrolidin-1-yl)ethyl)piperidine |
| 4 | (S)-1-(3-(1-(Mesitylsulfonyl)azetidin-2-yl)propylsulfonyl)-4-(2-(pyrrolidin-1-yl)ethyl)piperidine hydrochloride |
| 5 | 1-(1-Methylpiperidin-4-yl)-4-(4-(1-(naphthalen-1-ylsulfonyl)pyrrolidin-2-yl)butylsulfonyl)piperazine dihydrochloride |
| 6 | 1-(4-(1-(Mesitylsulfonyl)pyrrolidin-2-yl)butylsulfonyl)-4-(2-(pyrrolidin-1-yl)ethyl)piperidine |
| 7 | 1-(4-(1-(4-Methoxy-2,3,6-trimethylphenylsulfonyl)pyrrolidin-2-yl)butylsulfonyl)-4-(1-methylpiperidin-4-yl)piperazine |
| 8 | 1-(4-(1-(4-Methoxy-2,3,6-trimethylphenylsulfonyl)pyrrolidin-2-yl)butylsulfonyl)-4-(2-(pyrrolidin-1-yl)ethyl)piperidine |
| 9 | 1-(4-(1-(2,6-Dichloro-4-(trifluoromethyl)phenylsulfonyl)pyrrolidin-2-yl)butylsulfonyl)-4-(1-methylpiperidin-4-yl)piperazine |
| 10 | 1-(4-Methoxy-2,3,6-trimethylphenylsulfonyl)-3-(3-(4-(2-(pyrrolidin-1-yl)ethyl)piperidin-1-ylsulfonyl)propyl)piperidine hydrochloride |
| 11 | 1-(Mesitylsulfonyl)-3-(3-(4-(2-(pyrrolidin-1-yl)ethyl)piperidin-1-ylsulfonyl)propyl)piperidine hydrochloride |
| 12 | 1-(Mesitylsulfonyl)-4-(3-(4-(2-(pyrrolidin-1-yl)ethyl)piperidin-1-ylsulfonyl)propyl)piperidine |
| 13 | 1-(3-(1-(Mesitylsulfonyl)piperidin-4-yl)propylsulfonyl)-4-(1-methylpiperidin-4-yl)piperazine |
| 14 | 1-(2,6-Dichloro-4-(trifluoromethyl)phenylsulfonyl)-4-(2-(4-(2-(pyrrolidin-1-yl)ethyl)piperidin-1-ylsulfonyl)ethyl)piperidine |
| 15 | 2-(4-Methoxy-2,3,6-trimethylphenylsulfonyl)-4-(2-(4-(2-(pyrrolidin-1-yl)ethyl)piperidin-1-ylsulfonyl)ethyl)isoxazolidine |
| 16 | 1-(2-(1-(4-Methoxy-2,3,6-trimethylphenylsulfonyl)pyrrolidin-3-yl)ethylsulfonyl)-4-(2-(pyrrolidin-1-yl)ethyl)piperidine hydrochloride |
| 17 | 1-(2-(1-(2,3-Dichlorophenylsulfonyl)pyrrolidin-3-yl)ethylsulfonyl)-4-(2-(pyrrolidin-1-yl)ethyl)piperidine hydrochloride |
| 18 | 4-(2-(Pyrrolidin-1-yl)ethyl)-1-(2-(1-(2,4,5-trichlorophenylsulfonyl)pyrrolidin-3-yl)ethylsulfonyl)piperidine hydrochloride |
| 19 | 1-(2-(1-(4-Chloro-2,5-dimethylphenylsulfonyl)pyrrolidin-3-yl)ethylsulfonyl)-4-(2-(pyrrolidin-1-yl)ethyl)piperidine |
| 20 | 1-(2-(1-(Mesitylsulfonyl)pyrrolidin-3-yl)ethylsulfonyl)-4-(pyridin-4-yl)piperazine hydrochloride |
| 21 | 1-(2-(1-(2,3-Dichlorophenylsulfonyl)pyrrolidin-3-yl)ethylsulfonyl)-4-(pyridin-4-yl)piperazine hydrochloride |
| 22 | 1-(2-(1-(4-Methoxy-2,3,6-trimethylphenylsulfonyl)pyrrolidin-3-yl)ethylsulfonyl)-4-(pyridin-4-yl)piperazine |
| 23 | 1-(2-(1-(4-Chloro-2,5-dimethylphenylsulfonyl)pyrrolidin-3-yl)ethylsulfonyl)-4-(pyridin-4-yl)piperazine |
| 24 | 1-(2-(1-(3,4-Dichlorophenylsulfonyl)pyrrolidin-3-yl)ethylsulfonyl)-4-(pyridin-4-yl)piperazine hydrochloride |
| 25 | 1-(2-(1-(4-Methoxy-2,6-dimethylphenylsulfonyl)pyrrolidin-3-yl)ethylsulfonyl)-4-(2-(pyrrolidin-1-yl)ethyl)piperidine hydrochloride |
| 26 | 1-(3-(1-(4-Methoxy-2,6-dimethylphenylsulfonyl)piperidin-2-yl)propylsulfonyl)-4-(1-methylpiperidin-4-yl)piperazine |
| 27 | (S)-1-(3-(1-(2-Chloro-6-methylphenylsulfonyl)pyrrolidin-2-yl)propylsulfonyl)-4-(1-methylpiperidin-4-yl)piperazine |
| 28 | (S)-1-(1-Methylpiperidin-4-yl)-4-(3-(1-(2,4,6-trichlorophenylsulfonyl)pyrrolidin-2-yl)propylsulfonyl)piperazine |
| 29 | (S)-1-(3-(1-(4-Cloro-2,5-dimethylphenylsulfonyl)pyrrolidin-2-yl)propylsulfonyl)-4-(1-methylpiperidin-4-yl)piperazine |

| | |
|---|---|
| 30 | (S)-1-(1-Methylpiperidin-4-yl)-4-(3-(1-(naphthalen-1-ylsulfonyl)pyrrolidin-2-yl)propylsulfonyl)piperazine |
| 31 | (S)-1-(3-(1-(2,4-Dichlorophenylsulfonyl)pyrrolidin-2-yl)propylsulfonyl)-4-(1-methylpiperidin-4-yl)piperazine |
| 32 | (S)-1-(3-(1-(4-Methoxy-2,6-dimethylphenylsulfonyl)pyrrolidin-2-yl)propylsulfonyl)-4-(1-methylpiperidin-4-yl)piperazine |
| 33 | (S)-1-(3-(1-(2,2-Diphenylethylsulfonyl)pyrrolidin-2-yl)propylsulfonyl)-4-(1-methylpiperidin-4-yl)piperazine |
| 34 | (R)-1-(3-(1-(4-Methoxy-2,6-dimethylphenylsulfonyl)pyrrolidin-2-yl)propylsulfonyl)-4-(1-methylpiperidin-4-yl)piperazine |
| 35 | (S)-1-(1-Methylpiperidin-4-yl)-4-(3-(1-(3-(trifluoromethyl)phenylsulfonyl)pyrrolidin-2-yl)propylsulfonyl)piperazine |
| 36 | 4-(1-(3-((2R,4S)-4-Fluoro-1-(4-methoxy-2,6-dimethylphenylsulfonyl)pyrrolidin-2-yl)propylsulfonyl)piperidin-4-yloxy)pyridine |
| 37 | 1-(1-Methylpiperidin-4-yl)-4-((1-(3-(trifluoromethyl)phenylsulfonyl)piperidin-2-yl)methylsulfonyl)piperazine |
| 38 | 1-(2-(1-(4-Chloro-2,5-dimethylphenylsulfonyl)piperidin-2-yl)ethylsulfonyl)-4-(1-methylpiperidin-4-yl)piperazine dihydrochloride |
| 39 | 1-(4-Methoxy-2,3,6-trimethylphenylsulfonyl)-3-(2-(4-(2-(pyrrolidin-1-yl)ethyl)piperidin-1-ylsulfonyl)ethyl)piperidine hydrochloride |
| 40 | (S)-2-(4-(3-(1-(4-Methoxy-2,3,6-trimethylphenylsulfonyl)pyrrolidin-2-yl)propylsulfonyl)piperazin-1-yl)thiazole |
| 41 | (R)-1-(3-(1-(Mesitylsulfonyl)pyrrolidin-2-yl)propylsulfonyl)-4-(1-methylpiperidin-4-yl)piperazine dihydrochloride |
| 42 | 1-(4-(1-(Mesitylsulfonyl)pyrrolidin-2-yl)butylsulfonyl)-4-(1-methylpiperidin-4-yl)piperazine dihydrochloride |
| 43 | 3-((4-(2-(1-(4-Chloro-2,5-dimethylphenylsulfonyl)pyrrolidin-3-yl)ethylsulfonyl)piperazin-1-yl)methyl)benzonitrile hydrochloride |
| 44 | 1-(3-(1-(4-Methoxy-2,6-dimethylphenylsulfonyl)indolin-2-yl)propylsulfonyl)-4-(pyridin-3-yl)piperidin-4-ol |
| 45 | 1-(4-Methoxy-2,6-dimethylphenylsulfonyl)-2-(3-(9-(pyridin-4-yl)-3,9-diazaspiro[5.5]undecan-3-ylsulfonyl)propyl)indoline |
| 46 | (S)-4-(1-(3-(1-(2-Chloro-6-methylphenylsulfonyl)pyrrolidin-2-yl)propylsulfonyl)piperidin-4-yloxy)pyridine |
| 47 | (S)-4-(1-(3-(1-(4-Methoxy-2,6-dimethylphenylsulfonyl)pyrrolidin-2-yl)propylsulfonyl)piperidin-4-yloxy)pyridine |
| 48 | (S)-4-(1-(3-(1-(2-(Trifluoromethyl)phenylsulfonyl)pyrrolidin-2-yl)propylsulfonyl)piperidin-4-yloxy)pyridine |
| 49 | (S)-4-(1-(3-(1-(Naphthalen-2-ylsulfonyl)pyrrolidin-2-yl)propylsulfonyl)piperidin-4-yloxy)pyridine |
| 50 | (S)-4-(1-(3-(1-(Naphthalen-1-ylsulfonyl)pyrrolidin-2-yl)propylsulfonyl)piperidin-4-yloxy)pyridine |
| 51 | (S)-4-(1-(3-(1-(2,4-Dichlorophenylsulfonyl)pyrrolidin-2-yl)propylsulfonyl)piperidin-4-yloxy)pyridine |
| 52 | (S)-4-(1-(3-(1-(2,3-Dichlorophenylsulfonyl)pyrrolidin-2-yl)propylsulfonyl)piperidin-4-yloxy)pyridine |
| 53 | (S)-4-(1-(3-(1-(4-Chloro-2,5-dimethylphenylsulfonyl)pyrrolidin-2-yl)propylsulfonyl)piperidin-4-yloxy)pyridine |
| 54 | (1R,3R,5S)-8-(3-((S)-1-(4-Methoxy-2,6-dimethylphenylsulfonyl)pyrrolidin-2-yl)propylsulfonyl)-3-(pyridin-4-yloxy)-8-azabicyclo[3.2.1]octane |
| 55 | (1R,3R,5S)-8-(3-((S)-1-(2-Chloro-6-methylphenylsulfonyl)pyrrolidin-2-yl)propylsulfonyl)-3-(pyridin-4-yloxy)-8-azabicyclo[3.2.1]octane |
| 56 | (1R,3R,5S)-3-(Pyridin-4-yloxy)-8-(3-((S)-1-(2-(trifluoromethyl)phenylsulfonyl)pyrrolidin-2-yl)propylsulfonyl)-8-azabicyclo[3.2.1]octane |
| 57 | (1R,3R,5S)-8-(3-((S)-1-(Naphthalen-2-ylsulfonyl)pyrrolidin-2-yl)propylsulfonyl)-3-(pyridin-4-yloxy)-8-azabicyclo[3.2.1]octane |
| 58 | (1R,3R,5S)-8-(3-((S)-1-(Naphthalen-1-ylsulfonyl)pyrrolidin-2-yl)propylsulfonyl)-3-(pyridin-4-yloxy)-8-azabicyclo[3.2.1]octane |
| 59 | (1R,3R,5S)-8-(3-((S)-1-(2,4-Dichlorophenylsulfonyl)pyrrolidin-2-yl)propylsulfonyl)-3-(pyridin-4-yloxy)-8-azabicyclo[3.2.1]octane |
| 60 | (1R,3R,5S)-8-(3-((S)-1-(2,3-Dichlorophenylsulfonyl)pyrrolidin-2-yl)propylsulfonyl)-3-(pyridin-4-yloxy)-8-azabicyclo[3.2.1]octane |
| 61 | (1R,3R,5S)-8-(3-((S)-1-(4-Chloro-2,5-dimethylphenylsulfonyl)pyrrolidin-2-yl)propylsulfonyl)-3-(pyridin-4-yloxy)-8-azabicyclo[3.2.1]octane |
| 62 | 3-(3-((S)-1-(2-Chloro-6-methylphenylsulfonyl)pyrrolidin-2-yl)propylsulfonyl)-9-(pyridin-4-yloxy)-3-azaspiro[5.5]undecane |
| 63 | 9-(3,3-Difluoroazetidin-1-yl)-3-(3-((S)-1-(4-methoxy-2,6-dimethylphenylsulfonyl)pyrrolidin-2-yl)propylsulfonyl)-3-azaspiro[5.5]undecane |
| 64 | 3-(3-((S)-1-(4-Methoxy-2,6-dimethylphenylsulfonyl)pyrrolidin-2-yl)propylsulfonyl)-9-(pyridin-4-yl)-3,9-diazaspiro[5.5]undecane |
| 65 | 3-(3-((S)-1-(2-Chloro-6-methylphenylsulfonyl)pyrrolidin-2-yl)propylsulfonyl)-9-(pyridin-4-yl)-3,9-diazaspiro[5.5]undecane |
| 66 | 3-(3-((S)-1-(4-Methoxy-2,6-dimethylphenylsulfonyl)pyrrolidin-2-yl)propylsulfonyl)-9-(pyridin-4-yloxy)-3-azaspiro[5.5]undecane hydrochloride |
| 67 | 3-(3-((S)-1-(Naphthalen-1-ylsulfonyl)pyrrolidin-2-yl)propylsulfonyl)-9-(pyridin-4-yl)-3,9-diazaspiro[5.5]undecane hydrochloride |
| 68 | 3-(Pyridin-4-yl)-9-(3-((S)-1-(2-(trifluoromethyl)phenylsulfonyl)pyrrolidin-2-yl)propylsulfonyl)-3,9-diazaspiro[5.5]undecane hydrochloride |
| 69 | (S)-4-(1-(3-(1-(2,2-Dimethylchroman-6-ylsulfonyl)pyrrolidin-2-yl)propylsulfonyl)piperidin-4-yloxy)pyridine |
| 70 | (S)-4-(1-(3-(1-(3-Chlorobenzylsulfonyl)pyrrolidin-2-yl)propylsulfonyl)piperidin-4-yloxy)pyridine |
| 71 | (S)-4-(1-(3-(1-(2-Chloro-4-(trifluoromethyl)phenylsulfonyl)pyrrolidin-2-yl)propylsulfonyl)piperidin-4-yloxy)pyridine |
| 72 | (S)-4-(1-(3-(1-(2,6-Dichloro-4-(Trifluoromethyl)phenylsulfonyl)pyrrolidin-2-yl)propylsulfonyl)piperidin-4-yloxy)pyridine |
| 73 | (S)-4-(1-(3-(1-(4-Fluoro-2,6-dimethylphenylsulfonyl)pyrrolidin-2-yl)propylsulfonyl)piperidin-4-yloxy)pyridine |
| 74 | 3-(3-(1-(4-Methoxy-2,6-dimethylphenylsulfonyl)piperidin-2-yl)propylsulfonyl)-9-(pyridin-4-yl)-3,9-diazaspiro[5.5]undecane |
| 75 | 3-(3-((S)-1-(4-Methylnaphthalen-1-ylsulfonyl)pyrrolidin-2-yl)propylsulfonyl)-9-(pyridin-4-yl)-3,9-diazaspiro[5.5]undecane |
| 76 | 3-(3-((S)-1-(5-Chloronaphthalen-1-ylsulfonyl)pyrrolidin-2-yl)propylsulfonyl)-9-(pyridin-4-yl)-3,9-diazaspiro[5.5]undecane |
| 77 | 3-(3-((S)-1-(4-Methoxynaphthalen-1-ylsulfonyl)pyrrolidin-2-yl)propylsulfonyl)-9-(pyridin-4-yl)-3,9-diazaspiro[5.5]undecane |
| 78 | 3-(3-((S)-1-(4-Fluoronaphthalen-1-ylsulfonyl)pyrrolidin-2-yl)propylsulfonyl)-9-(pyridin-4-yl)-3,9-diazaspiro[5.5]undecane |
| 79 | 3-(3-((S)-1-(4-Chloronaphthalen-1-ylsulfonyl)pyrrolidin-2-yl)propylsulfonyl)-9-(pyridin-4-yl)-3,9-diazaspiro[5.5]undecane |
| 80 | (1R,3s,5S)-8-(1-(3-((S)-1-(4-Methoxy-2,6-dimethylphenylsulfonyl)pyrrolidin-2-yl)propylsulfonyl)azetidin-3-yl)-3-(pyridin-4-yloxy)-8-azabicyclo[3.2.1]octane |
| 81 | (1R,3s,5S)-8-(1-(3-((S)-1-(2-Chloro-6-methylphenylsulfonyl)pyrrolidin-2-yl)propylsulfonyl)azetidin-3-yl)-3-(pyridin-4-yloxy)-8-azabicyclo[3.2.1]octane |
| 82 | 2-(3-((S)-1-(4-Methoxy-2,6-dimethylphenylsulfonyl)pyrrolidin-2-yl)propylsulfonyl)-7-(pyridin-4-yl)-2,7-diazaspiro[4.4]nonane |
| 83 | 2-(3-((S)-1-(2-Chloro-6-methylphenylsulfonyl)pyrrolidin-2-yl)propylsulfonyl)-7-(pyridin-4-yl)-2,7-diazaspiro[4.4]nonane |
| 84 | 2-(3-((S)-1-(4-Methoxy-2,5-dimethylphenylsulfonyl)pyrrolidin-2-yl)propylsulfonyl)-7-(pyridin-4-yl)-2,7-diazaspiro[4.4]nonane |
| 85 | (S)-2-(3-(1-(4-Methoxy-2,6-dimethylphenylsulfonyl)pyrrolidin-2-yl)propylsulfonyl)-8-(pyridin-4-yl)-2,8-diazaspiro[4.5]decane |
| 86 | 3-(3-(1-(2-Chloro-6-methylphenylsulfonyl)piperidin-2-yl)propylsulfonyl)-9-(pyridin-4-yl)-3,9-diazaspiro[5.5]undecane |
| 87 | 3-(3-(1-(4-Methoxy-2,6-dimethylphenylsulfonyl)piperidin-2-yl)propylsulfonyl)-9-(pyridin-3-yl)-9-(2-(pyrrolidin-1-yl)ethoxy)-3-azaspiro[5.5]undecane | and physiologically acceptable salts of any of the foregoing.

20. A pharmaceutical composition comprising a compound as claimed in claim 1 and at least one pharmaceutically acceptable carrier or auxiliary substance.

21. A method of treating a disorder or disease state selected from the group consisting of pain, migraine, diabetes, respiratory tract diseases, inflammatory intestinal diseases, neurological diseases, skin inflammations, rheumatic diseases, septic shock, reperfusion syndrome and obesity, or of inhibiting angiogenesis, in a subject in need thereof; said method comprising administering to said subject a pharmacologically effective amount of a compound as claimed in claim 1.

22. A method as claimed in claim 21, wherein said disorder is pain selected from the group consisting of acute pain, visceral pain, neuropathic pain, chronic pain and inflammation pain.

* * * * *